United States Patent [19]
Tsujihara et al.

[11] Patent Number: 5,837,673
[45] Date of Patent: Nov. 17, 1998

[54] CAMPTOTHECIN DERIVATIVES

[75] Inventors: Kenji Tsujihara, Urawa; Takayuki Kawaguchi, Toshima-ku; Satoshi Okuno, Misato; Toshiro Yano, Urawa, all of Japan

[73] Assignee: Tanabe Seiyaku Co., Ltd., Osaka, Japan

[21] Appl. No.: 689,018

[22] Filed: Jul. 30, 1996

[30] Foreign Application Priority Data

| Aug. 2, 1995 | [JP] | Japan | 7-197391 |
| Dec. 27, 1995 | [JP] | Japan | 7-340619 |
| Jul. 3, 1996 | [JP] | Japan | 8-173372 |

[51] Int. Cl.⁶ .......................... A61K 31/00; A61K 38/14; C07K 9/00
[52] U.S. Cl. .................. 814/2; 514/18; 514/19; 530/322; 530/330; 530/331; 544/346; 544/361
[58] Field of Search .......... 530/322, 330–331; 514/2, 18, 19; 544/346, 361

[56] References Cited

U.S. PATENT DOCUMENTS

| 5,140,010 | 8/1992 | Goldstein et al. ............ 514/17 |
| 5,463,022 | 10/1995 | Inoue et al. ................ 830/322 |

FOREIGN PATENT DOCUMENTS

| 2109259 | 4/1994 | Canada. |
| 0220601 | 5/1987 | European Pat. Off.. |
| 0296597 | 12/1988 | European Pat. Off.. |
| 0418099 | 5/1991 | European Pat. Off.. |
| 0540099 | 5/1993 | European Pat. Off.. |
| 0556585 | 8/1993 | European Pat. Off.. |
| 0640622 | 3/1995 | European Pat. Off.. |
| 1-279891 | 11/1989 | Japan. |
| 4-503505 | 6/1992 | Japan. |
| 5-502017 | 4/1993 | Japan. |
| 5-222048 | 8/1993 | Japan. |
| 0687746 | 3/1994 | Japan. |
| 6-228141 | 8/1994 | Japan. |
| 908479 | 10/1990 | South Africa. |
| 9003169 | 4/1990 | WIPO. |
| 90132098 | 4/1990 | WIPO. |
| WO9104260 | 4/1991 | WIPO. |
| 9316698 | 9/1993 | WIPO. |
| WO9510304 | 4/1995 | WIPO. |

OTHER PUBLICATIONS

*Cancer and Chemotherapy*, vol. 21, p. 709 (1994).
*Enhancement of Effects of Anticancer Agents and Targeting Therapy*, p. 227 (1987), published by Science Forum Ltd.
*Enhancement of Effects of Anticancer Agents and Targeting Therapy*, p. 278 (1987), published by Science Forum Ltd.
Takakura et al.—Cancer Research 44,2505–2510, Jun. 1984.
Zhao et al.—Bioorganic & Medicinal Chemistry Letters, vol. 5, No. 24, pp. 3063–3066, 1995.
Kawato et al.—J. Pharm. Pharmacol, 1993, 45: 444–448.
Pommier et al.—DNA Topoisomerase Cancer Pub. Oxford Univ. (1991).
Wani et al.—J. Med. Chem. 1980, 23, 554–560.
Wani et al.—J. Med. Chem. 1986, 29, 2358–2363.
Jaxel et al.—Cancer Research 49, 1465–1469, Mar. 15, 1989.
Kingsbury et al., J. Med. Chem., 34:98–107 (1991).

*Primary Examiner*—Cecilia J. Tsang
*Assistant Examiner*—Bennett Culsa
*Attorney, Agent, or Firm*—Birch, Stewart, Kolasch & Birch, LLP

[57] ABSTRACT

A camptothecin derivative comprising a compound of the formula [I]:

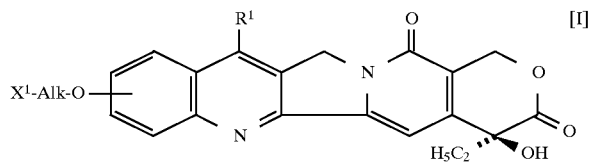

wherein $R^1$ is a substituted or unsubstituted lower alkyl group, $X^1$ is a group of the formula: —$NHR^2$ ($R^2$ is a hydrogen atom or a lower alkyl group) or a group of —OH, and Alk is a straight chain or branched chain alkylene group having optionally an oxygen atom in the chain thereof, bound to a polysaccharide having carboxyl groups via an amino acid or a peptide, or a pharmaceutically acceptable salt thereof. Said camptothecin derivatives show enhanced antitumor activities but few side effects unlike conventional anticancer agents, and hence, these compounds are extremely useful as a medicament.

47 Claims, No Drawings

CAMPTOTHECIN DERIVATIVES

TECHNICAL FIELD

The present invention relates to a novel camptothecin derivative having enhanced antitumor activities, and intermediates therefor. More particularly, the present invention relates to a novel camptothecin derivative which is prepared by combining an aminoalkoxy- or hydroxyalkoxy-camptothecin compound with a polysaccharide having carboxyl groups via an amino acid or a peptide, intermediates therefor, and a process for preparing the same. The camptothecin derivative of the present invention can be delivered into a target region of the patient selectively and in much amount, so that they can show desired pharmacological activities at the desired region of the patient. Thus, the antitumor activities of the camptothecin compounds are enormously enhanced and their side effects can be reduced, and hence, these compounds are extremely useful as a medicament.

PRIOR ART

Camptothecin is one of plant alkaloids, and has the following formula:

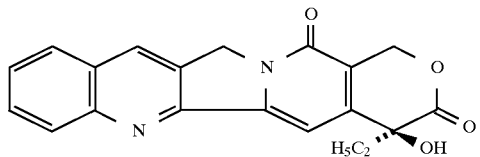

and it has been known to show antileukemic and antitumor activities, and one of campthothecin derivatives, irinothecan hydrochloride {CPT-11, 7-ethyl-10-[4-(piperidino)-1-piperidino]carbonyloxycamptothecin}, has already been put on the market. However, CPT-11 shows potent antitumor activities in clinical use but also shows severe toxicity like other antitumor agents, so that CPT-11 has been restricted in its therapeutic use [cf. Cancer and Chemotherapy, vol. 21, p. 709 (1994)].

On the other hand, in order to enhance the antitumor activity and also to reduce the side effects thereof as low as possible, these compounds having such severe side effects have been studied as to a kind of drug delivery system therefor, by which a necessary amount of a drug is selectively delivered into a target tissue. Especially, in the chemotherapy of cancers, it is a serious problem that there is no significant difference between tumor cells and normal cells in sensitivity against anticancer agents, and many studies on targeting-type drug delivery system for anticancer agents have been done in order to selectively deliver an anticancer agent into a cancer-bearing region, for example, doxorubicin-polysaccharide complex (WO 94/19376), doxorubicin-inclusive liposome (Enhancement of effects of anticancer agents and targeting therapy, p. 227 (1987), published by Science Forum Ltd.), dextran-binding mitomycin (Enhancement of effects of anticancer agents and targeting therapy, p. 278 (1987), published by Science Forum Ltd.).

As explained above, camptothecin compounds show excellent anti-tumor activities and are very useful as a medicament but they are strictly restricted in clinical use because of their severe side effects. Thus, it is desired to develop a new camptothecin derivative wherein the excellent pharmacological activities are duly retained but undesirable severe side effects are suppressed.

Under the above mentioned circumstances, the present inventors have intensively studied in order to obtain an excellent camptothecin derivative without the drawback of the conventional camptothecin compounds by utilizing the techniques of the above mentioned drug delivery system, and finally have found that a novel camptothecin derivative having desired pharmacological effects can be obtained by combining a camptothecin compound having a reactive group with a polysaccharide having carboxyl groups via an amino acid or a peptide, and have accomplished the present invention.

BRIEF DESCRIPTION OF INVENTION

An object of the present invention is to provide a novel camptothecin derivative comprising the camptothecin compound [I] bound to a polysaccharide having carboxyl groups via an amino acid or a peptide.

Another object of the present invention is to provide a novel intermediate which is selected from the camptothecin compound [I] and a camptothecin compound comprising the camptothecin compound [I] bound to an amino acid or a peptide.

Still further object of the present invention is to provide a process for preparing these camptothecin derivative and intermediates therefor.

DETAILED DESCRIPTION OF INVENTION

The compound of the present invention is a comptothecin derivative comprising a camptothecin compound having an aminoalkoxy group or a hydroxyalkoxy group, represented by the formula [I]:

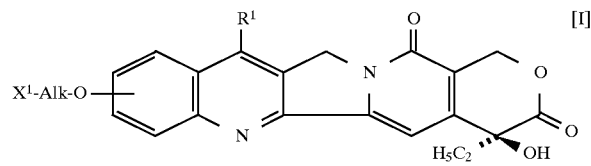

wherein $R^1$ is a substituted or unsubstituted lower alkyl group, $X^1$ is a group of the formula: —$NHR^2$ ($R^2$ is a hydrogen atom or a lower alkyl group) or a group of the formula: —OH, and Alk is a straight chain or branched chain alkylene group having optionally an oxygen atom in the chain thereof, bound to a polysaccharide having carboxyl groups via an amino acid or a peptide.

According to the studies by the present inventors, it has been found that the novel camptothecin compound of the above formula [I] and a compound which is prepared by combining the compound [I] with an amino acid or a peptide are both very useful as an intermediate for the desired camptothecin derivative of the present invention, and also that they per se have an excellent anti-tumor activity.

The camptothecin derivative of the present invention includes compounds which are prepared by combining the camptothecin compound [I] with a polysaccharide having carboxyl groups via an amino acid or a peptide, for example, ones which are prepared by combining a part or all of the carboxyl groups of an amino acid or a peptide with $X^1$ of the compound [I] through acid-amide or ester bonds, followed by combining a part or all of the carboxyl groups of a polysaccharide with an amino group of said amino acid or said peptide through acid-amide bonds. More particularly, the camptothecin derivative of the present invention includes compounds which are prepared by combining the C-terminal carboxyl group of an amino acid or a peptide with $X^1$ of the compound [I] through acid-amide or ester bonds, followed by combining a part or all of the carboxyl groups of the polysaccharide with the N-terminal amino group of said amino acid or said peptide through acid-amide bonds.

Each substituent of the compound of the formula [I] of the present invention is explained below.

The lower alkyl group for $R^1$ and $R^2$ when $X^1$ is a group of the formula: —NHR$^2$ includes alkyl groups having 1 to 4 carbon atoms, for example, methyl, ethyl, propyl, isopropyl, butyl, isobutyl, tert-butyl, etc. The substituent of the lower alkyl group for $R^1$ includes, for example, a protected or unprotected hydroxy, mercapto and amino group, and these groups may optionally be protected by an alkyl group or an acyl group, etc.

The straight chain or branched chain alkylene group having optionally an oxygen atom in the chain thereof for Alk includes a straight chain or branched chain alkylene group having 1 to 6 carbon atoms, for example, methylene, ethylene, trimethylene, propylene, tetramethylene, pentamethylene, hexamethylene, 1-methylethylene, 1-methylpropylene, 2-methylpropylene, etc., and a straight chain or branched chain alkylene group having 2 to 6 carbon atoms and having one or more oxygen atoms in the chain thereof, such as —CH$_2$CH$_2$—O—CH$_2$CH$_2$—, —CH$_2$CH$_2$CH$_2$—O—CH$_2$CH$_2$—, —CH$_2$CH(CH$_3$)—O—CH$_2$CH$_2$—, —CH$_2$CH$_2$—O—CH$_2$CH$_2$—O—CH$_2$CH$_2$—, etc.

Among the compounds [I] of the present invention, the compound of the formula [I] wherein $X^1$ is a group of the formula: —NHR$^2$, i.e. a compound of the formula [I']:

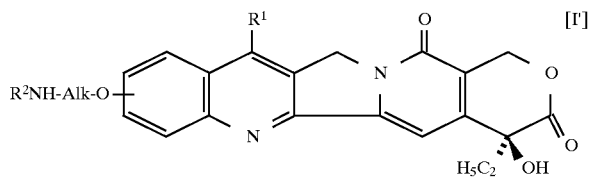

wherein $R^1$, $R^2$ and Alk are the same as defined above, is preferable, and more particularly, among the compounds [I], the compound of the formula [I'] wherein $R^1$ is an unsubstituted lower alkyl group, $R^2$ is a hydrogen atom, Alk is a straight chain or branched chain alkylene group having 2 to 4 carbon atoms having no oxygen atom in the chain thereof is more preferable.

Among the compounds [I], the compound of the formula [I] wherein $R^1$ is ethyl group, and $X^1$—Alk—O— is 3-aminopropyloxy group which is bonded at the 10-position of the camptothecin nucleus, is most preferable.

The polysaccharide having carboxyl groups includes the same as those as disclosed in the above mentioned WO 94/19376, and includes polysaccharides having originally carboxyl groups in the structure thereof (e.g. hyaluronic acid, pectic acid, alginic acid, chondroitin, heparin, etc.), and polysaccharide having originally no carboxyl group (e.g. pullulan, dextran, mannan, chitin, mannoglucan, chitosan, etc.) but being introduced thereto carboxyl groups. Among these polysaccharides, dextran is especially preferable, particularly dextran having an average molecular weight of 20,000 to 400,000 is more preferable, and particularly dextran having an average molecular weight of 50,000 to 150,000 is most preferable (said average molecular weight being determined by Gel permeation chromatography method, Shinseikagaku Jikken Koza, vol. 20, p. 7). The polysaccharides having originally no carboxyl group but being introduced thereto carboxyl groups mean ones which are prepared by substituting a part or all of hydrogen atoms of hydroxy groups of polysaccharides having originally no carboxyl group with a carboxy-C$_{1-4}$ alkyl group.

The "polysaccharide having carboxyl groups" of the present invention also includes ones which are prepared by treating a polysaccharide originally having no carboxyl group with a reducing agent, and then followed by substituting the hydrogen atoms of a part or all of hydroxyl groups of the product with a carboxy-C$_{1-4}$ alkyl group.

The alkyl moiety of the carboxy-C$_{1-4}$ alkyl group may be either a straight chain alkyl group or a branched chain alkyl group. Preferable carboxy-C$_{1-4}$ alkyl group is, for example, carboxymethyl group, 1-carboxyethyl group, 3-carboxypropyl group, 1-methyl-3-carboxypropyl group, 2-methyl-3-carboxypropyl group, 4-carboxybutyl group, etc., and carboxymethyl group and 1-carboxyethyl group are more preferable. In the present invention, the polysaccharide having carboxyl groups is preferably a carboxymethylated dextran or pullulan.

When introducing a carboxyalkyl group into polysaccharides, the degree of the introduction thereto is expressed by "degree of substitution" which is defined by a number of carboxyalkyl groups per a sugar residue, i.e. expressed by the following equation.

$$\text{Degree of Substitution} = \frac{\text{Number of carboxyalkyl groups in the molecule}}{\text{Total number of sugar residues in the molecule}}$$

When the carboxyalkyl group is carboxymethyl group, the degree of substitution is occasionally expressed by the degree of carboxymethylation (CM-degree).

When the polysaccharide is pullulan, dextran or mannoglucan, and all of the hydroxy groups thereof are substituted, the degree of substitution thereof is 3, and preferable degree of substitution is in the range of 0.3 to 0.8.

When the polysaccharide is chitin, and all of the hydroxy groups thereof are substituted, the degree of substitution thereof is 2, and preferable degree of substitution is in the range of 0.3 to 0.8.

Besides, it is essential that the polysaccharide of the present invention should have at least one carboxyalkyl group in the molecule except for polysaccharides having originally carboxyl groups. Thus, polysaccharides with the degree of substitution of 0 should be excluded from the polysaccharide of the present invention.

The polysaccharide having carboxyl groups may be prepared by the method disclosed in WO 94/19376.

The amino acid which intervenes between a camptothecin compound [I] and a polysaccharide having carboxyl groups includes both natural amino acids and synthetic amino acids (including D-amino acid, L-amino acid, a mixture thereof), and also includes either neutral amino acids, basic amino acids or acidic amino acids. Moreover, the amino acid of the present invention may be not only α-amino acids but also β-amino acids, γ-amino acids, ε-amino acids, etc., and includes, for example, glycine, α-alanine, β-alanine, valine, leucine, isoleucine, serine, threonine, cysteine, methionine, aspartic acid, glutamic acid, lysine, arginine, phenylalanine, tyrosine, histidine, tryptophan, proline, hydroxyproline, γ-aminobutyric acid, ε-aminocaproic acid, etc.

The peptide of the present invention includes peptides derived from the above amino acids, or peptides having compounds other than amino acids in the part of the chain thereof. For example, a dicarboxylic acid such as succinic acid, a diamine such as ethylenediamine, or a diol such as ethyleneglycol may exist in the middle of the peptide chain or the terminus of the peptide chain. Besides, the binding site of the peptide chain to the carboxyl groups of the polysaccharide usually starts from the N-terminus of the peptide chain through acid-amide bonds. When a basic amino acid (e.g. lysin) exists in the peptide chain, the binding site of the peptide chain may be reversed by binding the ε-amino group of basic amino acid with carboxyl groups of a polysaccharide, and binding an α-amino group with the C-terminus of the peptide chain.

Such peptides may be ones composed of more than one amino acid, i.e. ones having more than one amino acid, more preferably ones having 2 to 5 peptide chains. Suitable examples of peptide chain are -Gly-Gly-L- or D- Phe-Gly-, -L or D-Phe-Gly-, -L or D-Tyr-Gly-, -L or D-Leu-Gly-, -Gly-Gly-, -Gly-Gly-Gly-, -Gly-Gly-Gly-Gly- (SEQ ID No:1) or -Gly-Gly-Gly-Gly-Gly- (SEQ ID No: ) and peptide chains containing these sequences (the N-terminus of the these peptides or peptide chains containing these sequences is introduced onto the carboxyl groups of a polysaccharide). Among these peptides, -Gly-Gly-L or D-Phe-Gly-, -Gly-Gly-, -Gly-Gly-Gly-, -Gly-Gly-Gly-Gly- (SEQ ID No:1), -Gly-Gly-Gly- Gly-Gly- (SEQ ID No:2), -L or D-Phe-Gly- and -L or D-Leu-Gly- are more preferable.

Among them, -Gly-Gly-L-Phe-Gly, -Gly-Gly-, -Gly-Gly-Gly-, -Gly-Gly-Gly-Gly- (SEQ ID No:1), -L or D-Phe-Gly- are most preferable.

The camptothecin derivatives of the present invention may usually be prepared by combining the compound [I] with an amino acid or a peptide, followed by reacting the product with a polysaccharide having carboxyl groups.

When $X^1$ of the formula [I] is a group of the formula: —NHR$^2$, the compound [I] is combined with the C-terminal carboxyl group of an amino acid or a peptide through acid-amide bonds. When $X^1$ of the formula [I] is a group of the formula: —OH, the compound [I] is combined with the C-terminal carboxyl group of an amino acid or a peptide through ester bonds. In this case, it is preferable to protect other functional groups of the amino acid or the peptide which do not participate in said acid-amide bonds or ester bonds, for example, the N-terminal amino group or other carboxyl groups are protected in a conventional manner, prior to the reaction of the compound [I] and an amino acid or a peptide. The protecting group may be any protecting groups which are conventionally used for protection of amino acids, and the protecting group of amino group is, for example, t-butoxycarbonyl group, p-methoxybenzyloxycarbonyl group, etc., and the protecting group of carboxyl group is, for example, a lower alkyl group (e.g. t-butyl group), benzyl group, etc.

The production of the above mentioned acid-amide bonds or ester bonds between $X^1$ of the compound [I] and an amino acid or a peptide is carried out by a conventional method, for example, by reacting in the presence of a condensing agent in a suitable solvent. The solvent includes, for example, dimethylformamide, acetonitrile, chloroform, methylene chloride, etc., and the condensing agent includes, for example, dicyclohexylcarbodiimide, 1-(3-dimethylaminopropyl)-3-ethylcarbodiimide hydrochloride, etc.

The camptothecin compound prepared by combining the compound [I] with an amino acid or a peptide, after removing protecting groups of amino group therefrom when amino group thereof is protected, is reacted with a polysaccharide having carboxyl groups, to give the desired camptothecin derivatives of the present invention. In this reaction, a part or all of the carboxyl groups of the polysaccharide are combined with the N-terminal amino group of the amino acid or that of the peptide which is previously bonded to the camptothecin compound [I], through acid-amide bonds.

The reaction of the camptothecin compound which is produced by combining the compound [I] with an amino acid or a peptide, and a polysaccharide having carboxyl groups is carried out by a conventional method, for example, in the presence of a condensing agent in a suitable solvent. The solvent includes, for example, water, ethanol, dimethylformamide, or a mixture thereof, and the condensing agent includes, for example, 1-(3-dimethylaminopropyl) -3-ethylcarbodiimide hydrochloride, 2-ethyloxy-1-ethyloxycarbonyl-1,2-dihydroquinoline, etc.

In the camptothecin derivatives of the present invention, the ratio of the polysaccharide and the camptothecin compound [I] which is an active ingredient may be selected according to the kinds of the polysaccharide to be used, but the content of the camptothecin compound [I] in the camptothecin derivative is preferably in the range of 0.1 to 20% by weight, more preferably in the range of 2 to 10% by weight, when the polysaccharide is pullulan, dextran, chitin or mannoglucan.

When dextran is used as a polysaccharide in the present invention, the average molecular weight of the camptothecin derivative of the present invention is preferably in the range of 30,000 to 500,000, more preferably, in the range of 60,000 to 200,000, determined by the GPC analysis.

The camptothecin derivatives of the present invention thus obtained may be converted into a pharmaceutically acceptable salt thereof, if necessary. The pharmaceutically acceptable salt includes, for example, salts with an alkali metal or an alkaline earth metal (e.g. sodium salt, potassium salt, calcium salt, etc.), or salts with an amino acid (e.g. arginine salt, lysine salt, etc.).

The camptothecin compound of the formula [I] may be prepared by the following Reaction Scheme 1.

Reaction Scheme 1

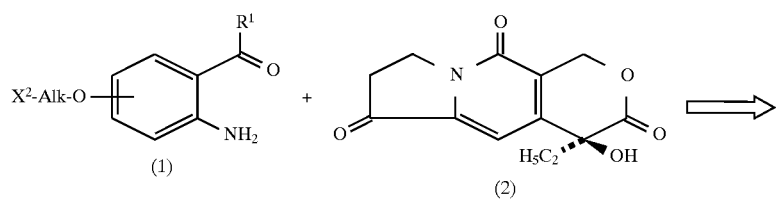

-continued
Reaction Scheme 1

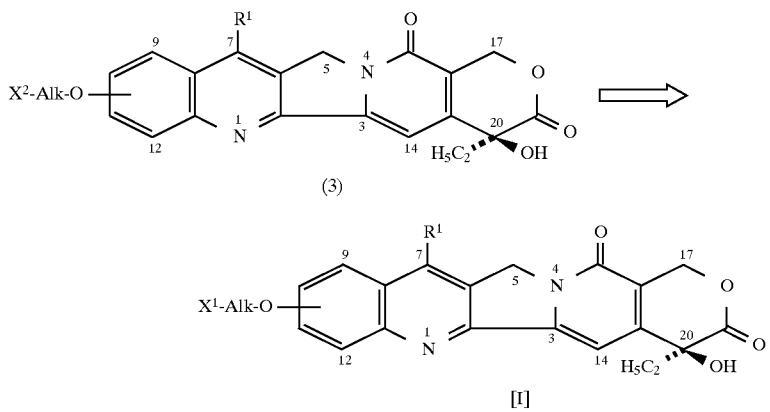

wherein $X^2$ is a protecting group—$N(R^2)$— or a protecting group —O—, and $R^1$, $X^1$ and Alk are the same as defined above.

That is, the aminocarbonyl compound (1) is condensed with a known pyranoindolidine (2) (cf. EP-0220601-A) by a method known as Friedländer condensation reaction (cf. Organic Reactions, 28, pp. 37–202, John Wiley & Sons, Inc., New York (1982)), followed by removing the protecting groups from the product to give the desired camptothecin compound [I].

In the above reaction scheme, $R^1$ may be introduced after said Friedländer condensation reaction.

Instead of the compound (1), a compound of the formula (1) wherein $R^1$ is a hydrogen atom is condensed with the compound (2) by Friedländer condensation reaction, and the resulting condensed product is subjected to radical reaction disclosed in Chem. Pharm. Bull., 39, 2574–2581 (1991) with a derivative of the formula: $R^1$—CO—X (X is a hydrogen atom or a reactive group) to give the desired compound [I].

Further, instead of the aminocarbonyl compound (1) in the above Reaction Scheme 1, when using a compound of the formula [II]:

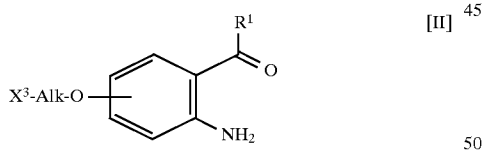

wherein $X^3$ is $R^3$—$N(R^2)$— or $R^3$—O—, $R^3$ is a group which is prepared by removing a hydroxy group from the carboxyl group of an amino acid or peptide having a protected amino group, and $R^1$, $R^2$ and Alk are the same as defined above, a camptothecin compound wherein the camptothecin compound [I] and an amino acid or a peptide are combined may be obtained.

The starting aminocarbonyl compound (1) wherein $X^2$ is a protecting group—$N(R^2)$— may be prepared by the following Reaction Scheme 2.

Reaction Scheme 2

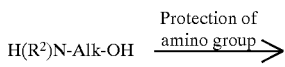

-continued
Reaction Scheme 2

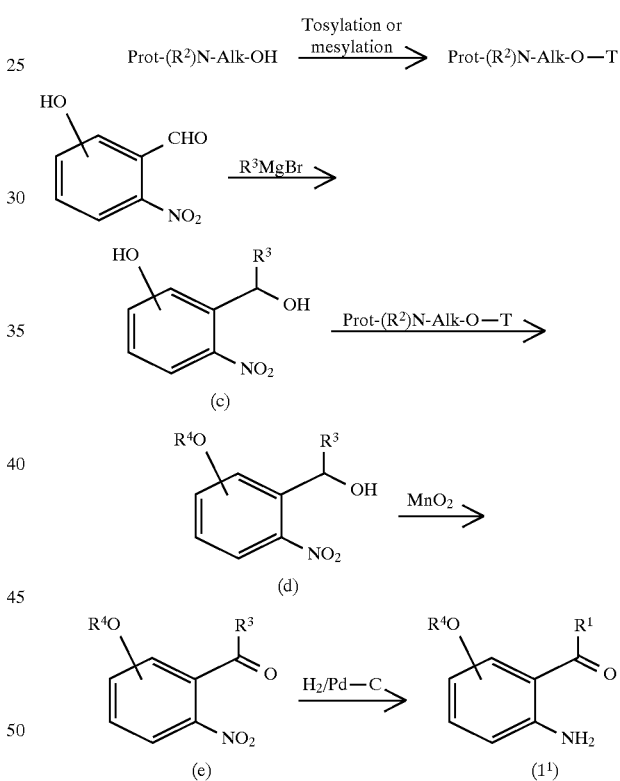

wherein $R^1$ and Alk are the same as defined above, $R^3$ is a substituted or unsubstituted lower alkenyl or alkyl group, $R^4$ is a protected aminoalkyl group, Prot is a protecting group and T is a tosyl group or a mesyl group.

A protecting group is introduced onto the aminoalkanol, $H(R^2)N$—Alk—OH, to give a protected aminoalkanol (a), which is tosylated or mesylated to give a compound (b) wherein the hydroxy group is activated. On the other hand, a Grignard reagent ($R^3MgBr$) is reacted with a hydroxy-substituted o-nitrobenzaldehyde, and the resulting compound (c) is reacted with the previously prepared compound (b) to give a compound (d) wherein the phenolic hydroxy group is alkylated. The compound (d) is treated with an oxidizing agent, for example, active manganese dioxide to give a ketone compound (e), followed by subjecting the compound (e) to catalytic reduction in the presence of a suitable catalyst such as Pd-C to give a compound ($1^1$). may be isolated from the reaction mixture but can be used in the condensation reaction with the compound (2) without purification or isolation.

In the above Reaction Scheme 2, a protecting group of amino group in $R^4$ of the ketone compound (e) is removed by a conventional manner, and the resulting product is reacted with an amino acid or a peptide having a protected amino group. The resulting product is subjected to catalytic reduction in the same manner as the reduction of the ketone compound (e) to give the aminocarbonyl compound (1) wherein the protecting group in $X^2$ is replaced by a group which is prepared by removing a hydroxy group from the carboxyl group of an amino acid or peptide having a protected amino group.

Among the starting aminocarbonyl compounds (1) in the above Reaction Scheme 1, the compound (1) wherein $X^2$ is a protecting group—O— is prepared by the following Reaction Scheme 3.

Reaction Scheme 3

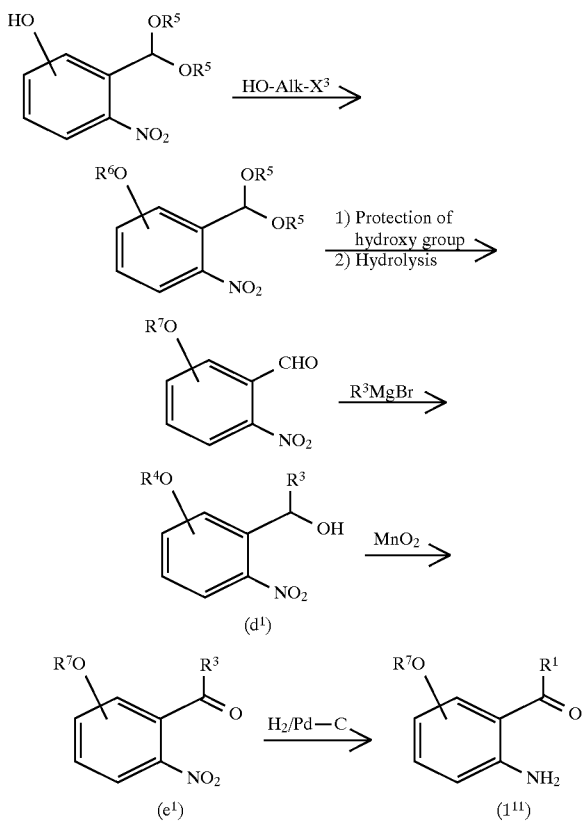

wherein Alk, $R^1$ and $R^3$ are the same as defined above, $R^5$ is a lower alkyl group, $X^3$ is a halogen atom, $R^6$ is a hydroxyalkyl group, and $R^7$ is a protected hydroxyalkyl group.

The hydroxy-substituted o-nitrobenzaldehyde dialkyl acetal is reacted with hydroxyalkyl halide to have the phenolic hydroxy group hydroxyalkylated. The hydroxy group of said hydroxyalkyl group is protected, for example, by t-butyldimethylsilyl group, etc. and the acetal product thus obtained is subjected to hydrolysis to give an alkoxy-substituted o-nitrobenzaldehyde derivative, which is reacted with a Grignard reagent in the same manner as in Reaction Scheme 2 to give a compound ($d^1$). The compound ($d^1$) is oxidized in the same manner as in Reaction Scheme 2, and the resulting compound ($e^1$) is further subjected to catalytic reduction to give the compound ($1^{11}$).

Besides, in the above Reaction Scheme 3, the protecting group of hydroxy group of the compound ($e^1$) is removed by a conventional method, and the product thus obtained is reacted and combined through an ester bond with an amino acid or a peptide having a protected amino group in the same manner as in the preparation of the compound [I], and then the resulting product is subjected to catalytic reduction in the same manner as in the reduction of the compound ($e^1$) to give a compound [II].

The camptothecin derivatives of the present invention and a pharmaceutically acceptable salt thereof show excellent antitumor activities against various tumors, especially they show excellent therapeutic effects on solid tumors such as pulmonary cancer, uterine cancer, ovarian cancer, breast cancer, gastrointestinal cancer (large bowel cancer, gastric cancer, etc.).

The camptothecin derivatives of the present invention and a pharmaceutically acceptable salt thereof are preferably administered parenterally (e.g. intravascular injection), and are usually used in the form of a liquid preparation (e.g. solution, suspension, emulsion, etc.).

The dosage of the desired compound of the present invention varies according to the administration method, ages, weights or conditions of the patients, but it is usually in the range of 0.02–50 mg/kg/day, more preferably in the range of 0.1–10 mg/kg/day, converted into the dose of the camptothecin compound [I] or the camptothecin compound [I] hydrochloride when $X^1$ is a group of the formula: —$NHR^2$.

The compounds of the present invention and a process for preparing thereof are illustrated in more detail by the following Examples, but should not be construed to be limited thereto.

EXAMPLE 1

Preparation of 10-(3'-aminopropyloxy)-7-ethyl-(20S)-camptothecin hydrochloride (1) Preparation of 3-t-butoxycarbonylaminopropanol 3-Aminopropanol (6.0 g) is dissolved in methylene chloride (50 ml), and thereto is added dropwise with stirring di-t-butyl dicarbonate (18.3 g) under ice-cooling. The mixture is stirred at room temperature for 2 hours, and concentrated, and the residue is purified by silica gel column chromatography to give 3-t-butoxycarbonylaminopropanol (13.98 g) as a colorless oil.

Yield: 99.9%

IR (Neat): $v_{max}^{cm-1}$=3380, 1790

Mass: m/z=176 (M+H$^+$)

NMR (300 MHz, CDCl$_3$): $\delta^{TMS}$=1.45 (9H, s), 1.62–1.72 (2H, m), 3.0 (1H, brs), 3.29 (2H, dd, J=12 Hz, 6 Hz), 3.66 (2H, dd, J=12 Hz, 6 Hz), 4.80 (1H, brs)

(2) Preparation of 3-t-butoxycarbonylaminopropyl tosylate 3-t-Butoxycarbonylaminopropanol (10.0 g) is dissolved in methylene chloride (100 ml), and thereto are added with stirring triethylamine (8.66 g) and tosyl chloride (16.3 g) under ice-cooling, and the mixture is stirred at room temperature overnight. The reaction mixture is concentrated, and the residue is dissolved in a mixture of water and ethyl acetate. The organic layer is separated, washed with a saturated sodium chloride solution, dried over sodium sulfate, and concentrated under reduced pressure. The residue is purified by silica gel column chromatography to give 3-t-butoxycarbonylaminopropyl tosylate (15.37 g) as a pale yellow oil.

Yield: 82%

IR (Neat): $\nu_{max}^{cm-1}$=3400, 3340, 1700, 1600

Mass: m/z=352 (M+Na$^+$)

NMR (300 MHz, CDCl$_3$): $\delta^{TMS}$=1.42 (9H, s), 1.78–1.90 (2H, m), 2.45 (3H, s), 3.11–3.22 (2H, m), 4.09 (2H, t, J=6 Hz), 4.5–4.65 (1H, m), 7.36 (2H, d, J=8 Hz), 7.77–7.83 (2H, m)

(3) Preparation of 1-(5'-hydroxy-2'-nitrophenyl)-2-propen-1-ol

5-Hydroxy-2-nitrobenzaldehyde (6.0 g) is dissolved in dry tetrahydrofuran (90 ml), and thereto is added dropwise with stirring vinylmagnesium bromide (2.3 equivalents) under −78° C. The mixture is gradually warmed, and after the reaction is completed, to the reaction mixture is added 1N hydrochloric acid. The mixture is extracted with ethyl acetate, and the organic layer is separated, washed with a saturated sodium chloride solution, dried over sodium sulfate, and concentrated under reduced pressure. The residue is purified by silica gel column chromatography to give 1-(5'-hydroxy-2'-nitrophenyl)-2-propen-1-ol (5.09 g) as a yellow brown powder.

Yield: 73%

M.p.: 126°–130° C.

IR (Nujol): $\nu_{max}^{cm-1}$=3440, 1600

Mass: m/z=195 (M$^+$)

NMR (300 MHz, CDCl$_3$): $\delta^{TMS}$=2.4 (1H, br), 5.19 (1H, dd, J=10.5 Hz, 1.5 Hz), 5.38 (1H, dd, J=17 Hz, 1.5 Hz), 5.89 (1H, m), 6.08 (1H, ddd, J=17 Hz, 10.5 Hz, 5 Hz), 6.80 (1H, dd, J=9 Hz, 3 Hz), 7.22 (1H, d, J=3 Hz), 7.97 (1H, d, J=9 Hz), 9.90 (1H, brs)

(4) Preparation of 1-[5'-(3"-t-butoxycarbonylaminopropyloxy)-2'-nitrophenyl]-2-propen-1-ol 1-(5'-Hydroxy-2'-nitrophenyl)-2-propen-1-ol (2.0 g) is dissolved in dry DMF (100 ml) and thereto are added sodium iodide (1 equivalent), potassium carbonate and 3-t-butoxycarbonylaminopropyl tosylate (1.5 equivalent). The mixture is stirred at 50° C. for 6 hours, and thereto is added ethyl acetate. The mixture is washed with a saturated sodium chloride solution and dried over sodium sulfate. The residue is purified by silica gel column chromatography to give 1-[5'-(3"-t-butoxycarbonylaminopropyloxy)-2'-nitrophenyl]-2-propen-1-ol (3.53 g) as a pale brown caramel.

Yield: 98%

IR (Neat): $\nu_{max}^{cm-1}$=3400, 1690, 1680

Mass: m/z=375 (M+Na$^+$)

NMR (300 MHz, CDCl$_3$): $\delta^{TMS}$=1.44 (9H, s), 1.96–2.06 (2H, m), 2.80 (1H, brs), 3.33 (2H, q, J=6.5 Hz), 4.11 (2H, t, J=6 Hz), 4.8 (1H, brs), 5.24 (1H, dd, J=10.5 Hz, 1.5 Hz), 5.42 (1H, dd, J=17 Hz, 1.5 Hz), 5.92 (1H, d, J=5 Hz), 6.08 (1H, ddd, J=17 Hz, 10.5 Hz, 5 Hz), 6.86 (1H, dd, J=9 Hz, 3 Hz), 7.25 (1H, d, J=3 Hz), 8.04 (1H, d, J=9 Hz)

(5) Preparation of 1-[5'-(3"-t-butoxycarbonylaminopropyloxy)-2'-nitrophenyl]-2-propen-1-one 1-(5'-(3"-t-Butoxycarbonylaminopropyloxy)-2'-nitrophenyl)-2-propen-1-ol (9.66 g) is dissolved in chloroform (300 ml), and thereto is added active manganese dioxide (72 g), and the mixture is refluxed. After the reaction is completed, the inorganic materials are removed by filtration through a pad of Celite, and the filtrate is concentrated, stirred at 50° C. for 6 hours, and thereto is added ethyl acetate. The mixture is washed with a saturated sodium chloride solution, and dried over sodium sulfate. The residue is purified by silica gel column chromatography to give 1-[5'-(3"-t-butoxycarbonylaminopropyloxy)-2'-nitrophenyl]-2-propen-1-one (6.01 g) as a yellow product.

M.p.: 65°–71° C.

Yield: 63%

IR (Neat): $\nu_{max}^{cm-1}$=3350, 1700

Mass: m/z=351 (M+H$^+$)

NMR (300 MHz, CDCl$_3$): $\delta^{TMS}$=1.44 (9H, s), 1.98–2.18 (2H, m), 3.28–3.37 (2H, q, J=6.5 Hz), 4.08–4.16 (2H, m), 4.67 (1H, brs), 5.85 (1H, d, J=17.5 Hz), 6.02 (1H, d, J=10.5 Hz), 6.62 (1H, dd, J=17.5 Hz, 10.5 Hz), 6.82 (1H, d, J=3 Hz), 7.03 (1H, dd, J=9 Hz, 3 Hz), 8.17 (1H, d, J=9 Hz)

(6) Preparation of 1-[5'-(3"-t-butoxycarbonylaminopropyloxy)-2'-aminophenyl]-propan-1-one 1-[5'-(3"-t-Butoxycarbonylaminopropyloxy)-2'-nitrophenyl]-2-propen-1-one (325 mg) is dissolved in ethanol (15 ml), and thereto is added 10% palladium-carbon (40 mg), and the mixture is stirred for 1.5 hour under hydrogen atmosphere. The catalyst is removed by filtration, and the filtrate is concentrated, and the residue is purified by silica gel column chromatography to give 1-[5'-(3"-t-butoxycarbonylaminopropyloxy)-2'-aminophenyl]-propan-1-one (248 mg) as a yellow powder.

M.p.: 112°–115° C.

Yield: 83%

IR (Nujol): $\nu_{max}^{cm-1}$=3450, 3400, 3340, 1700, 1650

Mass: m/z=323 (M+H$^+$)

NMR (300 MHz, CDCl$_3$): $\delta^{TMS}$=1.21 (3H, t, J=7 Hz), 1.45 (9H, s), 1.90– 2.01 (2H, m), 2.95 (2H, q, J=7.5 Hz), 3.33 (2H, q, J=6.5 Hz), 3.97 (2H, t, J=6.5 Hz), 4.48 (1H, brs), 5.96 (2H, brs), 6.62 (1H, d, J=9 Hz), 6.95 (1H, dd, J=9 Hz, 3 Hz), 7.24 (1H, d, J=3 Hz)

(7-1) Preparation of 10-(3'-t-butoxycarbonylaminopropyloxy)-7-ethyl-(20S)-camptothecin 1-[5'-(3"-t-Butoxycarbonylaminopropyloxy)-2'-aminophenyl]-propan-1-one (4.54 g) is dissolved in ethanol (200 ml), and thereto are added (4S)-7,8-dihydro-4-ethyl-4-hydroxy-1H-pyrano[3,4-f]indolidine-3,6,10(4H)-trione (1.85 g) and p-toluenesulfonic acid (134 mg), and the mixture is refluxed. After the reaction is completed, the mixture is concentrated under reduced pressure, and the residue is purified by silica gel column chromatography to give 10-(3'-t-butoxycarbonylaminopropyloxy)-7-ethyl-(20S)-camptothecin (2.47 g) as a pale yellow powder.

M.p.: 196°–201° C. (decomposed)

Yield: 64%

IR (Nujol): $\nu_{max}^{cm-1}$=3450, 3385, 1740, 1715, 1685, 1665, 1620

Mass: m/z=550 (M+H$^+$)

NMR (300 MHz, CDCl$_3$): $\delta^{TMS}$=1.03 (3H, t, J=7.5 Hz), 1.39 (3H, t, J=7.5 Hz), 1.46 (9H, s), 1.82–1.98 (2H, m), 2.04–2.16 (2H, m), 3.12 (2H, q, J=7.5 Hz), 3.41 (2H, q, J=6 Hz), 3.93 (1H, s), 4.20 (2H, t, J=6 Hz), 4.84 (1H, brs), 5.21 (2H, s), 5.29 (1H, d, J=16 Hz), 5.74 (1H, d, J=16 Hz), 7.28 (1H, d, J=3 Hz), 7.43 (1H, dd, J=9 Hz, 3 Hz), 7.60 (1H, s), 8.12 (1H, d, J=9 Hz)

(7-2) Preparation of 10-(3'-acetylaminopropyloxy)-7-ethyl-(20S)-camptothecin

The corresponding starting compounds are treated in the same manners as in the above (1) to (7-1) to give 10-(3'-acetylaminopropyloxy)-7-ethyl-(20S)-camptothecin.

M.p.: 240°–245° C. (decomposed)

IR (Nujol): $\nu_{max}{}^{cm-1}$=3405, 3330, 1730, 1680, 1655

Mass: m/z=492 (M+H$^+$)

NMR (300 MHz, d$_6$-DMSO): $\delta^{TMS}$=0.8$_8$ (3H, t, J=7.5 Hz), 1.31 (3H, t, J=7.5 Hz), 1.82 (3H, s), 1.80–2.0 (4H, m), 3.1–3.2 (2H, m), 3.26 (2H, dt, J=13 Hz, 6 Hz), 4.21 (2H, t, J=6 Hz), 5.26 (2H, s), 5.42 (2H, s), 6.51 (1H, s), 7.25 (1H, s), 7.45 (1H, d, J=3 Hz), 7.49 (1H, dd, J=9 Hz, 3 Hz), 7.98 (1H, t, J=5 Hz), 8.05 (1H, d, J=9 Hz)

(8-1) Preparation of 10-(3'-aminopropyloxy)-7-ethyl-(20S)-camptothecin hydrochloride 10-(3'-t-Butoxycarbonylaminopropyloxy)-7-ethyl-(20S)-camptothecin (641 mg) is dissolved in dioxane (10 ml), and thereto is added dropwise with stirring 18% hydrochloric acid in dioxane (11 ml) in an ice-bath. The mixture is stirred at room temperature, and after the reaction is completed, isopropyl ether (15 ml) is added to the reaction mixture. The mixture is stirred, and the precipitated powder is collected by filtration, washed with ether, and dried under reduced pressure. The resulting powder is dissolved in water, and lyophilized to give 10-(3'-aminopropyloxy)-7-ethyl-(20S)-camptothecin hydrochloride (563 mg) as a yellow powder.

M.p.: >218° C. (decomposed)

Yield: 99%

IR (Nujol): $\nu_{max}{}^{cm-1}$=3370, 1745, 1655

Mass: m/z=450 [(M–Cl$^-$)$^+$]

NMR (300 MHz, d$_6$-DMSO): $\delta^{TMS}$=0.88 (3H, t, J=7 Hz), 1.32 (3H, t, J=8 Hz), 1.78–1.95 (2H, m), 2.08–2.19 (2H, m), 3.0–3.1 (2H, m), 3.13–3.25 (2H, m), 4.32 (2H, t, J=6 Hz), 5.32 (2H, s), 5.43 (2H, s), 7.28 (1H, s), 7.5–7.56 (2H, m), 7.99 (3H, brs), 8.11 (1H, d, J=10 Hz)

(8-2) Preparation of 10-(3'-aminopropyloxy)-7-ethyl-(20S)-camptothecin hydrochloride The product obtained in the above (7-2) is treated with hydrochloric acid-methanol to give 10-(3'-aminopropyloxy)-7-ethyl-(20S)-camptothecin hydrochloride. The physical properties of the product are identical to those of the compound obtained in the above (8-1).

EXAMPLE 2

Preparation of 10-(2'-aminoethyloxy)-7-ethyl-(20S)-camptothecin hydrochloride 10-(2'-Aminoethyloxy)-7-ethyl-(20S)-camptothecin hydrochloride is obtained in the same manner as in Example 1 as a yellow powder.

M.p.: >249° C. (decomposed)

Yield: 97%

IR (Nujol): $\nu_{max}{}^{cm-1}$=3400, 1745, 1655, 1620

Mass: m/z=436 [(M–Cl$^-$)$^+$]

NMR (300 MHz, d$_6$-DMSO): $\delta^{TMS}$=0.88 (3H, t, J=7.5 Hz), 1.32 (3H, t, J=7.5 Hz), 1.80–1.94 (2H, m), 3.21 (2H, q, J=7 Hz), 3.27–3.37 (2H, m), 4.45 (2H, t, J=5 Hz), 5.31 (2H, s), 5.43 (2H, s), 7.28 (1H, s), 7.54–7.58 (2H, m), 8.13 (1H, d, J=10 Hz), 8.31 (3H, brs)

EXAMPLE 3

Preparation of 10-(5'-aminopentyloxy)-7-ethyl-(20S)-camptothecin hydrochloride 10-(5'-Aminopentyloxy)-7-ethyl-(20S)-camptothecin hydrochloride is obtained in the same manner as in Example 1 as a yellow powder.

M.p.: >179° C. (decomposed)

Yield: 98%

IR (KBr): $\nu_{max}{}^{cm-1}$=3420, 1745, 1660, 1615

Mass: m/z=478 [(M–Cl$^-$)$^+$]

NMR (300 MHz, d$_6$-DMSO): $\delta^{TMS}$=0.88 (3H, t, J=7.5 Hz), 1.31 (3H, t, J=7.5 Hz), 1.49–1.59 (2H, m), 1.63–1.73 (2H, m), 1.80–1.91 (4H, m), 2.77–2.88 (2H, m), 3.19 (2H, q, J=8 Hz), 4.21 (2H, t, J=6Hz), 5.29 (2H, s), 5.43 (2H, s), 7.28 (1H, s), 7.48–7.53 (2H, m), 7.98 (3H, brs), 8.08 (1H, d, J=9 Hz)

EXAMPLE 4

Preparation of 9-(3'-aminopropyloxy)-7-ethyl-(20S)-camptothecin hydrochloride 9-(3'-Aminopropyloxy)-7-ethyl-(20S)-camptothecin hydrochloride is obtained in the same manner as in Example 1.

EXAMPLE 5

Preparation of 11-(3'-aminopropyloxy)-7-ethyl-(20S)-camptothecin hydrochloride 11-(3'-Aminopropyloxy)-7-ethyl-(20S)-camptothecin hydrochloride is obtained in the same manner as in Example 1.

EXAMPLE 6

Preparation of 10-[2'-(2"-aminoethyloxy)ethyloxy]-7-ethyl-(20S)-camptothecin hydrochloride 10-[2'-(2"-Aminoethyloxy)ethyloxy]-7-ethyl-(20S)-camptothecin hydrochloride is obtained in the same manner as in Example 1 as a yellow powder.

M.p.: >135° C. (gradually decomposed)

IR (KBr): $\nu_{max}{}^{cm-1}$=3405, 1745, 1655, 1615

Mass: m/z=480 [(M–Cl$^-$)$^+$]

NMR (300 MHz, d$_6$-DMSO): $\delta^{TMS}$=0.88 (3H, t, J=7.5 Hz), 1.32 (3H, t, J=7.5 Hz), 1.80–1.94 (2H, m), 2.97–3.06 (2H, m), 3.20 (2H, q, J=7.5 Hz), 3.75 (2H, t, J=5.5 Hz), 3.89–3.92 (2H, m), 4.38–4.40 (2H, m), 5.30 (2H, s), 5.43 (2H, s), 7.29 (1H, s), 7.52–7.56 (2H, m), 8.10 (1H, d, J=9.5 Hz), 8.04–8.23 (3H, brs)

EXAMPLE 7

Preparation of 10-(3'-methylaminopropyloxy)-7-ethyl-(20S)-camptothecin hydrochloride 10-(3'-Methylaminopropyloxy)-7-ethyl-(20S)-camptothecin hydrochloride is obtained in the same manner as in Example 1 as a yellow powder.

M.p.: >180° C. (decomposed)

Yield: 97%

IR (KBr): $\nu_{max}{}^{cm-1}$=3410, 1745, 1660, 1615

Mass: m/z=464 [(M–Cl$^-$)$^+$]

NMR (300 MHz, d$_6$-DMSO): $\delta^{TMS}$=0.88 (3H, t, J=7.5 Hz), 1.32 (3H, t, J=7.5 Hz), 1.80–1.94 (2H, m), 2.15–2.24 (2H, m), 2.57–2.61 (3H, m), 3.17–3.24 (4H, m), 4.33 (2H, t, J=6 Hz), 5.31 (2H, s), 5.43 (2H, s), 7.28 (1H, s), 7.52–7.55 (2H, m), 8.10 (1H, d, J=10 Hz), 9.00 (2H, brs)

EXAMPLE 8

Preparation of 10-[3'-(L-tyrosylamino)propyloxy]-7-ethyl-(20S)-camptothecin hydrochloride (1) Preparation of 10-[3'-(t-butoxycarbonyl-L-tyrosylamino)propyloxy]-7-ethyl-(20S)-camptothecin 10-(3'-Aminopropyloxy)-7-ethyl-(20S)-camptothecin hydrochloride (200 mg) is dissolved in dry DMF (10 ml), and thereto are added with stirring successively t-butoxycarbonyl-L-tyrosine (139 mg), triethylamine (44 mg), N-hydroxysuccinimide (85 mg) and 1-(3-dimethylaminopropyl)-3-ethyl-carbodiimide hydrochloride (95 mg) under ice-cooling. A catalytic amount of 4-dimethylaminopyridine (DMAP) is added thereto, and the mixture is stirred at room temperature. After the reaction is completed, the mixture is concentrated under reduced pressure, and extracted with chloroform. The extract is purified by silica gel column chromatography to give 10-[3'-(t-butoxy-carbonyl-L-tyrosylamino)propyloxy]-7-ethyl-(20S)-camptothecin (181 mg) as a pale yellow powder.

Yield: 62%

IR (Nujol): $\nu_{max}^{cm-1}$=3280, 1750, 1710

Mass: m/z=735 (M+Na$^+$)

NMR (300 MHz, CDCl$_3$): $\delta^{TMS}$=0.92 (3H, t, J=7 Hz), 1.31 (3H, t, J=7.5 Hz), 1.41 (9H, s), 1.75–2.02 (4H, m), 2.86–3.10 (4H, m), 3.3–3.6 (2H, m), 3.8–4.0 (2H, m), 4.24–4.38 (1H, m), 4.78 (1H, brs), 5.00 (2H, s), 5.21 (1H, d, J=16.5 Hz), 5.26–5.37 (1H, m), 5.64 (1H, d, J=16.5 Hz), 6.56 (1H, br), 6.81 (2H, d, J=8.5 Hz), 7.06 (2H, d, J=8.5 Hz), 7.12 (1H, d, J=2.5 Hz), 7.22–7.31 (1H, m), 7.60 (1H, s), 8.16 (1H, d, J=9 Hz)

(2) Preparation of 10-[3'-(L-tyrosylamino) propyloxy]-7-ethyl-(20S)-camptothecin hydrochloride 10-[3'-(t-Butoxycarbonyl-L-tyrosylamino)propyloxy]-7-ethyl-(20S)-camptothecin (157 mg) is dissolved in dioxane (5 ml), and thereto is added dropwise with stirring 18% hydrochloric acid in dioxane (2 ml) in an ice-bath. The mixture is stirred at room temperature, and after the reaction is completed, to the mixture is added isopropyl ether (20 ml). The mixture is stirred, and the precipitated powder is collected by filtration, washed with ether, and concentrated under reduced pressure. The residue is dissolved in water, and lyophilized to give 10-[3'-(L-tyrosylamino)propyloxy]-7-ethyl-(20S)-camptothecin hydrochloride (120 mg) as a yellow powder.

M.p.: >190° C. (decomposed)

Yield: 84%

IR (Nujol): $\nu_{max}^{cm-1}$=3375, 3240, 1740

Mass: m/z=613 [(M–Cl$^-$)$^+$]

NMR (300 MHz, d$_6$-DMSO): $\delta^{TMS}$=0.88 (3H, t, J=7 Hz), 1.32 (3H, t, J=8 Hz), 1.75–1.98 (4H, m), 2.93 (2H, d, J=7 Hz), 3.14–3.43 (4H, m), 3.87 (1H, t, J=7 Hz), 4.05–4.23 (2H, m), 5.30 (2H, s), 5.43 (2H, s), 6.71 (2H, d, J=8.5 Hz), 7.03 (2H, d, J=8.5 Hz), 7.28 (1H, s), 7.43–7.54 (2H, m), 8.09 (1H, d, J=9 Hz), 8.3 (3H, m), 8.66 (1H, t, J=5 Hz)

EXAMPLE 9

Preparation of 10-[3'-(glycylamino)propyloxy]-7-ethyl-(20S)-camptothecin hydrochloride 10-[3'-(Glycylamino)propyloxy]-7-ethyl-(20S)-camptothecin hydrochloride is obtained in the same manner as in Example 8 as a yellow powder.

M.p.: >190° C. (decomposed)

Yield: 93%

IR (Nujol): $\nu_{max}^{cm-1}$=3355, 3225, 1745, 1655

Mass: m/z=507 [(M–Cl$^-$)$^+$]

NMR (300 MHz, d$_6$-DMSO): $\delta^{TMS}$=0.85 (3H, t, J=7.5 Hz), 1.32 (3H, t, J=8 Hz), 1.79–1.94 (2H, m), 1.94–2.06 (2H, m), 3.20 (2H, q), 3.37 (2H, q), 3.52–3.60 (2H, m), 4.28 (2H, t, J=6 Hz), 5.29 (2H, s), 5.43 (2H, s), 7.29 (1H, s), 7.47–7.56 (1H, m), 7.51 (1H, s), 8.09 (1H, d, J=9 Hz), 8.20 (3H, m), 8.71 (1H, t, J=5.5 Hz)

EXAMPLE 10

Preparation of 10-[3'-(L-serylamino)propyloxy]-7-ethyl-(20S)-camptothecin hydrochloride (1) Preparation of 10-[3'-(t-butoxycarbonyl-L-serylamino)propyloxy]-7-ethyl-(20S)-camptothecin 10-(3'-Aminopropyloxy)-7-ethyl-(20S)-camptothecin hydrochloride (320 mg) is treated in the same manner as in Example 8-(1) to give 10-[3'-(t-butoxy-carbonyl-L-serylamino)propyloxy]-7-ethyl-(20S)-camptothecin (351 mg) as a pale yellow powder.

M.p.: 123°–129° C.

Yield: 84%

IR (Nujol): $\nu_{max}^{cm-1}$=3305, 1750, 1705

Mass: m/z=637 (M+H$^+$)

NMR (300 MHz, CDCl$_3$): $\delta^{TMS}$=1.00 (3H, t, J=7 Hz), 1.35 (3H, t, J=8 Hz), 1.45 (9H, s), 1.7–1.95 (2H, m), 2.08–2.20 (2H, m), 2.94–3.15 (2H, m), 3.53–3.64 (2H, m), 3.66–3.77 (2H, m), 4.12 (1H, d, J=4 Hz), 4.18 (2H, t, J=6 Hz), 4.2–4.3 (1H, m), 5.05 (2H, s), 5.26 (1H, d, J=16 Hz), 5.70 (1H, d, J=16 Hz), 5.74 (1H, d, J=8.5 Hz), 7.13–7.24 (1H, m), 7.40 (1H, dd, J=9 Hz, 3 Hz), 7.56 (1H, s), 8.02 (1H, d, J=9 Hz)

(2) Preparation of 10-[3'-(L-serylamino)propyloxy]-7-ethyl-(20S)-camptothecin hydrochloride 10-[3'-(L-Serylamino)propyloxy]-7-ethyl-(20S)-camptothecin hydrochloride (262 mg) is obtained in the same manner as in Example 8-(2) as a yellow powder.

M.p.: 173°–177° C. (decomposed)

Yield: 88%

IR (Nujol): $\nu_{max}^{cm-1}$=3350, 3240, 1745

Mass: m/z=537 [(M–Cl$^-$)$^+$]

NMR (300 MHz, d$_6$-DMSO): $\delta^{TMS}$=0.86 (3H, t, J=7 Hz), 1.32 (3H, t, J=8 Hz), 1.77–1.95 (2H, m), 1.95–2.07 (2H, m), 3.13–3.26 (2H, m), 3.32–3.45 (2H, m), 3.68–3.78 (2H, m), 3.78–3.86 (1H, m), 4.27 (2H, t, J=6 Hz), 5.30 (2H, s), 5.43 (2H, s), 7.29 (1H, s), 7.48–7.56 (1H, m), 7.51 (1H, brs), 8.09 (1H, d, J=9 Hz), 8.17–8.28 (3H, m), 8.72 (1H, t, J=5 Hz)

EXAMPLE 11

Preparation of 10-[3'-(L-phenylalanyl-glycylamino) propyloxy]-7-ethyl-(20S)-camptothecin hydrochloride (1) Preparation of 10-[3'-(t-butoxycarbonyl-L-phenylalanyl-glycylamino)-propyloxy]-7-ethyl-(20S)-camptothecin 10-(3'-Aminopropyloxy)-7-ethyl-(20S)-camptothecin hydrochloride (200 mg) is dissolved in dry DMF (20 ml) and thereto are added successively with stirring t-butoxycarbonyl-L-phenylalanylglycine (199 mg), triethylamine (44 mg), N-hydroxybenzotriazole (28 mg) and 1-(3-dimethylaminopropyl)-3-ethylcarbodiimide hydrochloride (118 mg) under ice-cooling. A catalytic amount of 4-dimethylaminopyridine is added to the mixtures, and the mixture is stirred at room temperature. After the reaction is completed, the mixture is concentrated under reduced pressure, extracted with chloroform, and purified by silica gel column chromatography to give 10-[3'-(t-butoxycarbonyl-L-phenylalanyl-glycylamino)propyloxy]-7-ethyl-(20S)-camptothecin (228 mg) as a pale yellow powder.

Yield: 73%

IR (Nujol): $v_{max}^{cm-1}$ 3300, 1750, 1655, 1625

Mass: m/z=754 (M+H$^+$)

NMR (300 MHz, CDCl$_3$): $\delta^{TMS}$=1.02 (3H, t, J=7 Hz), 1.37 (3H, t, J=7 Hz), 1.38 (9H, s), 1.81–1.97 (2H, m), 2.06–2.17 (2H, m), 2.95 (1H, dd, J=14 Hz, 8 Hz), 3.01–3.16 (2H, m), 3.12 (1H, dd, J=14 Hz, 6 Hz), 3.39–3.62 (2H, m), 3.93 (2H, m), 4.12–4.27 (3H, m), 5.03 (1H, d, J=6.5 Hz), 5.13 (2H, s), 5.26 (1H, d, J=16.5 Hz), 5.71 (1H, d, J=16.5 Hz), 6.7 (1H, br), 6.9 (1H, br), 7.09–7.17 (1H, m), 7.18–7.33 (5H, m), 7.35–7.43 (1H, m), 7.55 (1H, s), 8.04 (1H, d, J=9 Hz)

(2) Preparation of 10-[3'-(L-phenylalanyl-glycylamino)propyloxy]-7-ethyl-(20S)-camptothecin hydrochloride 10-[3'-(t-Butoxycarbonyl-L-phenylalanyl-glycylamino)propyloxy]-7-ethyl-(20S)-camptothecin (197 mg) is dissolved in dixone (5 ml), thereto is added dropwise with stirring 18% hydrochloric acid in dioxane (2.5 ml) in an ice-bath. The mixture is stirred at room temperature, and after the reaction is completed, to the mixture is added isopropyl ether (30 ml). The mixture is stirred, and the precipitated powder is collected by filtration, washed with ether, concentrated under reduced pressure, and the resulting powder is dissolved in water and lyophilized to give 10-[3'-(L-phenylalanylglycylamino)-propyloxy]-7-ethyl-(20S)-camptothecin hydrochloride (152 mg) as a yellow powder.

M.p.: >190° C. (decomposed)

Yield: 84%

IR (Nujol): $v_{max}^{cm-1}$=3230, 1745

Mass: m/z=654 [(M–Cl$^-$)$^+$]

NMR (300 MHz, d$_6$-DMSO): $\delta^{TMS}$=0.88 (3H, t, J=7 Hz), 1.31 (3H, t, J=7 Hz), 1.78–1.93 (2H, m), 1.93–2.06 (2H, m), 2.98 (1H, dd, J=13.5 Hz, 7.5 Hz), 3.11 (1H, dd, J=13.5 Hz, 6 Hz), 3.1–3.25 (2H, m), 3.25–3.38 (2H, m), 3.6–3.71 (1H, m), 3.75–3.9 (1H, m), 4.09 (1H, m), 4.25 (2H, t, J=6 Hz), 5.29 (2H, s), 5.43 (2H, s), 7.2–7.35 (6H, m), 7.50 (1H, s), 7.47–7.55 (1H, m), 8.08 (1H, d, J=9 Hz), 8.20 (1H, m), 8.4 (3H, brs), 8.92 (1H, m)

The compounds of Examples 12–15 are obtained in the same manner as in Example 11.

EXAMPLE 12

Preparation of 10-[2'-(L-phenylalanyl-glycylamino)ethyloxy]-7-ethyl-(20S)-camptothecin hydrochloride

EXAMPLE 13

Preparation of 9-[3'-(L-phenylalanyl-glycylamino)propyloxy]-7-ethyl-(20S)-camptothecin hydrochloride

EXAMPLE 14

Preparation of 11-[3'-(L-phenylalanyl-glycylamino)propyloxy]-7-ethyl-(20S)-camptothecin hydrochloride

EXAMPLE 15

Preparation of 10-[3'-(L-tyrosyl-glycylamino)propyloxy]-7-ethyl-(20S)-camptothecin hydrochloride (SEQ ID No: 3)

EXAMPLE 16

Preparation of 10-[3'-(glycyl-glycyl-L-phenylalanyl-glycylamino)propyloxy]-7-ethyl-(20S)-camptothecin hydrochloride (1) Preparation of 10-[3'-(t-butoxycarbonyl-glycyl-glycyl-L-phenylalanyl-glycylamino)propyloxy]-7-ethyl-(20S)-camptothecin (SEQ ID No: 3)

10-(3'-Aminopropyloxy)-7-ethyl-(20S)-camptothecin hydrochloride (650 mg) is treated in the same manner as in Example 11-(1) to give 10-[3'-(t-butoxycarbonyl-glycyl-glycyl-L-phenylalanyl-glycylamino)propyloxy]-7-ethyl-(20S)-camptothecin (SEQ ID No: 3) (714 mg) as a pale yellow powder.

Yield: 62%

IR (Nujol): $v_{max}^{cm-1}$=3290, 1750, 1655, 1625

Mass: m/z=890 (M+Na$^+$)

NMR (300 MHz, CDCl$_3$-d$_6$-DMSO): $\delta^{TMS}$=1.02 (3H, t, J=7.5 Hz), 1.36 (3H, t, J=7.5 Hz), 1.43 (9H, s), 1.82–1.98 (2H, m), 2.12 (2H, m), 3.00 (1H, dd, J=14.5 Hz, 10 Hz), 3.05–3.15 (2H, m), 3.19–3.29 (1H, dd, J=14.5 Hz, 6 Hz), 3.49 (2H, m), 3.65–3.85 (4H, m), 3.90 (2H, m), 4.18 (2H, t, J=6 Hz), 4.43–4.54 (1H, m), 4.80 (1H, brs), 5.15 (2H, s), 5.28 (1H, d, J=16.5 Hz), 5.70 (1H, d, J=16.5 Hz), 5.85–5.95 (1 H, m), 7.08–7.3 (6H, m), 7.28 (1H, d, J=3 Hz), 7.42 (1H, dd, J=9 Hz, 3 Hz), 7.50 (1H, d, J=7 Hz), 7.56 (1H, s), 7.61 (1H, m), 7.66–7.78 (1H, m), 8.04 (1H, d, J=9 Hz)

(2) Preparation of 10-[3'-(glycyl-glycyl-L-phenylalanyl-glycylamino)propyloxy]-7-ethyl-(20S)-camptothecin hydrochloride (SEQ ID No: 3)

10-[3'-(t-Butoxycarbonyl-glycyl-glycyl-L-phenylalanyl-glycylamino)-propyloxy]- 7-ethyl-(20S)-camptothecin (SEQ ID No: 3) (680 mg) is treated in the same manner as in Example 8-(2) to give 10-[3'-(glycyl-glycyl-L-phenylalanyl-glycylamino)propyloxy]-7-ethyl-(20S)-camptothecin hydrochloride (SEQ ID No: 3) (556 mg) as a yellow powder.

M.p.: >185° C. (decomposed)

Yield: 88%

IR (Nujol): $v_{max}^{cm-1}$=3240, 1745

Mass: m/z=768 [(M–Cl$^-$)$^+$]

NMR (300 MHz, d$_6$-DMSO): $\delta^{TMS}$=0.88 (3H, t, J=7 Hz), 1.31 (3H, t, J=8 Hz), 1.79–1.93 (2H, m), 1.93–2.05 (2H, m), 2.83 (1H, dd, J=14 Hz, 10 Hz), 3.05 (1H, dd, J=14 Hz, 4 Hz), 3.1–3.25 (2H, m), 3.25–3.4 (2H, m), 3.53–3.61 (2H, m), 3.64 (1H, m), 3.69 (1H, m), 3.76 (1H, dd, J=16 Hz, 6 Hz), 3.85 (1H, dd, J=16 Hz, 6 Hz), 4.25 (2H, t, J=6 Hz), 4.52 (1H, m), 5.28 (2H, s), 5.43 (2H, s), 7.12–7.19 (1H, m), 7.19–7.27 (5H, m), 7.30 (1H, s), 7.48–7.57 (2H, m), 7.91 (1H, t, J=6 Hz), 8.09 (1H, d, J=9 Hz), 8.17 (3H, br), 8.36 (1H, t, J=6 Hz), 8.43 (1H, d, J=8.5 Hz), 8.65 (1H, t, J=5 Hz)

EXAMPLE 17

Preparation of 10-[5'-(glycyl-glycyl-L-phenylalanyl-glycylamino)pentyloxy]-7-ethyl-(20S)-camptothecin hydrochloride (SEQ ID No: 3)

10-[5'-(Glycyl-glycyl-L-phenylalanyl-glycylamino)pentyloxy]-7-ethyl-(20S)-camptothecin hydrochloride is obtained in the same manner as in Example 11-(1) and Example 8-(2) as a yellow powder.

M.p.: >185° C. (decomposed)

IR (Nujol): $v_{max}^{cm-1}$=3250, 1740, 1660

Mass: m/z=796 [(M–Cl$^-$)$^+$]

NMR (300 MHz, d$_6$-DMSO): $\delta^{TMS}$=0.88 (3H, t, J=7.5Hz), 1.31 (3H, t, J=7.5 Hz), 1.56–1.60 (4H, m), 1.77–1.94 (4H, m), 2.79–2.89 (1H, m), 3.02–3.23 (5H, m), 3.58–3.90 (6H, m), 4.20 (2H, t, J=6 Hz), 4.49–4.60 (1H, m), 5.29 (2H, s), 5.43 (2H, s), 7.14–7.27 (5H, m), 7.30 (1H, s), 7.47–7.54 (2H, m), 7.85 (1H, t, J=6 Hz), 8.08 (1H, d, J=9 Hz), 8.04–8.20 (3H, br), 8.33 (1 H, t, J=6 Hz), 8.42 (1H, d, J=8 Hz), 8.64 (1H, t, J=6 Hz)

EXAMPLE 18

Preparation of 10-[3'-(N-(glycyl-glycyl-L-phenylalanyl-glycyl)-N-methyl-amino)propyloxy]-7-ethyl-(20S)-camptothecin hydrochloride (SEQ ID No: 3)

10-[3'-(N-(Glycyl-glycyl-L-phenylalanyl-glycyl)-N-methylamino)propyloxy]-7-ethyl-(20S)-camptothecin hydrochloride (SEQ ID No: 3) is obtained in the same manner as in Example 11-(1) and Example 8-(2) as a yellow powder.

M.p.: 190° C. (decomposed)

IR (Nujol): $\nu_{max}^{cm-1}$=3230, 1745, 1665

Mass: m/z=782 [(M–Cl⁻)⁺]

NMR (300 MHz, d₆-DMSO): $\delta^{TMS}$=0.88 (3H, t, J=7.5 Hz), 1.29–1.34 (3H, m), 1.80–1.94 (2H, m), 2.00–2.15 (2H, m), 2.65–2.84 (1H, dd, J=14 Hz, 10 Hz), 3.01 (3H, s), 3.06 (1H, dd, J=14 Hz, 4 Hz), 3.14–3.25 (2H, m), 3.82–4.40 (8H, m), 4.20–4.30 (2H, m), 4.53–4.64 (1H, m), 5.28 (2H, s), 5.30 (2H, s), 7.13–7.27 (5H, m), 7.30 (1H, s), 7.49–7.57 (2H, m), 8.08 (1H, dd, J=9 Hz, 3.5 Hz), 8.10–8.18 (3H, m), 8.31–8.39 (1H, m), 8.47 (1H, t, J=5.5 Hz), 8.53–8.60 (1H, m)

EXAMPLE 19

Preparation of 10-[2'-(glycyl-glycyl-L-phenylalanyl-glycylamino)ethyloxy]-7-ethyl-(20S)-camptothecin hydrochloride (SEQ ID No: 3)

10-[2'-(Glycyl-glycyl-L-phenylalanyl-glycylamino) ethyloxy]-7-ethyl-(20S)-camptothecin hydrochloride (SEQ ID No: 3) is obtained in the same manner as in Example 11-(1) and Example 8-(2) as a yellow powder.

M.p.: >189° C. (decomposed)

IR (Nujol): $\nu_{max}^{cm-1}$=3210, 1745, 1655, 1615

Mass: m/z=754 [(M–Cl⁻)⁺]

NMR (300 MHz, d₆-DMSO): $\delta^{TMS}$=0.88 (3H, t, J=7.5Hz), 1.26–1.33 (3H, m), 1.80–1.93 (2H, m), 2.81 (1H, dd, =14 Hz, 10 Hz), 3.06 (1H, dd, J=14 Hz, 5Hz), 3.21 (2H, q, J=7.5 Hz), 3.54–3.90 (8H, m), 4.26 (2H, t, J=5.5 Hz), 4.52–4.60 (1H, m), 5.30 (2H, s), 5.43 (2H, s), 7.17–7.25 (5H, m), 7.29 (1H, s), 7.50–7.56 (2H, m), 8.09 (1H, d, J=9 Hz), 8.12 (3H, br), 8.21 (1H, t, J=6 Hz), 8.39 (1H, d, J=5.5 Hz), 8.40 (1H, t, J=5.5 Hz), 8.60 (1H, t, J=5.5 Hz)

EXAMPLE 20

Preparation of 10-[3'-(γ-aminobutyroylamino) propylbxy]-7-ethyl-(20S)-camptothecin hydrochloride 10-[3'-(γ-Aminobutyroylamino)propyloxy]-7-ethyl-(20S)-camptothecin hydrochloride is obtained in the same manner as in Example 8 as a yellow powder.

M.p.: >152° C. (decomposed)

IR (Nujol): $\nu_{max}^{cm-1}$=3255, 1745, 1655, 1615

Mass: m/z=535 [(M–Cl⁻)⁺]

NMR (300 MHz, d₆-DMSO): $\delta^{TMS}$=0.88 (3H, t, J=7 Hz), 1.32 (3H, t, J=7 Hz), 1.75–1.99 (6H, m), 2.23 (2H, t, J=7 Hz), 2.74–2.81 (2H, m), 3.18–3.40 (4H, m), 4.25 (2H, t, J=6 Hz), 5.30 (2H, s), 5.43 (2H, s), 7.29 (1H, s), 7.50–7.54 (2H, m), 8.02 (3H, br), 8.09 (1H, d, J=9 Hz), 8.18 (1H, t, J=6 Hz)

EXAMPLE 21

Preparation of 10-[3'-{(N-(γ-aminobutyroyl)-γ-aminobutyroyl)amino}-propyloxy]-7-ethyl-(20S)-camptothecin hydrochloride 10-[3'-{(N-(γ-Aminobutyroyl)-γ-aminobutyroyl) amino}propyloxy]-7-ethyl-(20S)-camptothecin hydrochloride is obtained in the same manner as in Example 11 as a yellow powder.

M.p.: >134° C. (decomposed)

IR (KBr): $\nu_{max}^{cm-1}$=1745, 1655

Mass: m/z=620 [(M–Cl⁻)⁺]

NMR (300 MHz, d₆-DMSO): $\delta^{TMS}$=0.88 (3H, t, J=7.5 Hz), 1.32 (3H, t, J=7.5 Hz), 1.58–1.70 (2H, m), 1.70–1.82 (2H, m), 1.82–2.02 (4H, m), 2.11 (2H, t, J=7.5 Hz), 2.18 (2H, t, J=7.5 Hz), 2.70–2.81 (2H, m), 2.99–3.08 (2H, q), 3.15–3.33 (4H, m), 4.24 (2H, t, J=6 Hz), 5.31 (2H, s), 5.43 (2H, s), 7.30 (1H, s), 7.49–7.55 (2H, m), 7.86–8.10 (5H, m), 8.09 (1H, d, J=9 Hz)

EXAMPLE 22

Preparation of the camptothecin derivative of the following formula (SEQ ID No: 3):

CM.Dextran.Na—Gly—Gly-L-Phe—Gly—NH—(CH₂)₃—O—[camptothecin derivative structure]

[CM.Dextran.Na: carboxymethyldextran sodium salt]

CM-Dextran sodium salt (CM-degree; 0.4) (1.5 g) is dissolved in water (150 ml), and thereto is added with stirring 10-[3'-(glycyl-glycyl-L-phenyl-alanyl-glycylamino) propyloxy]-7-ethyl-(20S)-camptothecin hydrochloride (SEQ ID No: ) (75 mg) which is obtained in Example 16-(2) at a temperature below 10° C. To the mixture is added an aqueous solution (about 4 ml) of 1-(3-dimethylaminopropyl)-3-ethylcarbodiimide hydrochloride (EDC, 3 g), during which the pH value of the mixture is kept at pH 7.0–6.5 with 0.1N hydrochloric acid. The mixture is stirred at a temperature below 10° C. for two hours, and the pH value thereof is adjusted to pH 9 with 0.1N sodium hydroxide. The mixture is filtered, and ethanol (750 ml) is added to the filtrate. The precipitates are collected by centrifugation, dissolved in water (50 ml), and passed through an ion-exchange resin, AGMP-50 (Na-type, manufactured by Bio-Rad, Laboratories, Inc.). The fractions containing the desired compound are combined, filtered, and to the filtrate is added ethanol. The precipitates are collected by centrifugation, washed with the solvent, and dried under reduced pressure to give the desired camptothecin derivative (1.17 g). The content of 10-(3'-aminopropyloxy)-7-ethyl-(20S)-camptothecin hydrochloride (the compound of Example 1-(8-1)) in the desired camptothecin derivative is 1.4% which is calculated on the basis of the absorbance at 380 nm. According to the analysis by gel permeation chromatography (GPC), the average molecular weight of the desired camptothecin derivative is 137,000, and the degree of distribution (Mw/Mn) is 2.3.

Conditions for GPC analysis: G4000PWXL, 0.2M phosphate buffer (pH 7.0): acetonitrile=80:20, or G4000SWXL (manufactured by Toso, Ltd), 0.2M phosphate buffer (pH 7.0)

EXAMPLE 23

Preparation of the camptothecin derivative of the following formula (SEQ ID No: 3):

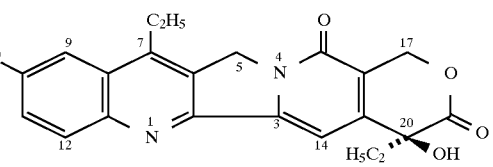

CM-Dextran sodium salt (CM-degree; 0.4) (1.0 g) is dissolved in water (100 ml), and thereto is added with stirring 10-[3'-(glycyl-glycyl-L-phenyl-alanyl-glycylamino) propyloxy]-7-ethyl-(20S)-camptothecin hydrochloride (SEQ ID No: 3) (120 mg) which is obtained in Example 16-(2) at a temperature below 10° C. To the mixture is added an aqueous solution (about 10 ml) of EDC (3 g), during which the pH value of the mixture is kept at pH 7.0–6.5 with 0.1N hydrochloric acid. The mixture is treated in the same manner as in Example 22 to give the desired camptothecin derivative (1.03 g). The content of 10-(3'-aminopropyloxy)-7-ethyl-(20S)-camptothecin hydrochloride (the compound of Example 1-(8-1)) in the desired camptothecin derivative is 4.6% which is calculated on the basis of the absorbance at 380 nm. According to the GPC analysis, the average molecular weight of the desired camptothecin derivative is 132,000, and the degree of distribution (Mw/Mn) is 2.3.

EXAMPLE 24

Preparation of the camptothecin derivative of the following formula:

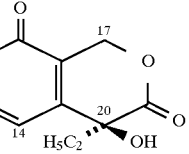

CM-Dextran sodium salt (CM-degree; 0.4) (1.2 g) and 10-[3'-(L-phenyl-alanyl-glycylamino)propyloxy]-7-ethyl-(20S)-camptothecin hydrochloride (130 mg) which is obtained in Example 11 are treated in the same manner as in Example 23 to give the desired camptothecin derivative (1.24 g). The content of 10-(3'-aminopropyloxy)-7-ethyl-(20S)-camptothecin hydrochloride (the compound of Example 1-(8-1)) in the desired camptothecin derivative is 5.7% which is calculated on the basis of the absorbance at 380 nm. According to the GPC analysis, the average molecular weight of the desired camptothecin derivative is 139,000, and the degree of distribution (Mw/Mn) is 2.2.

EXAMPLE 25

Preparation of the camptothecin derivative of the following formula (SEQ ID No: 3):

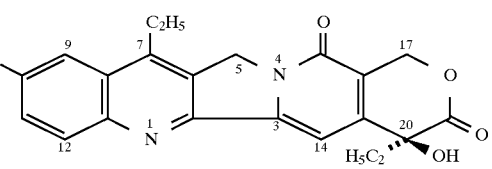

CM-Dextran sodium salt (CM-degree; 0.5) (500 mg) and 10-[2'-(glycyl-glycyl-L-phenylalanyl-glycylamino) ethyloxy]-7-ethyl-(20S)-camptothecin hydrochloride (SEQ ID No: 3) (50 mg) which is obtained in Example 19 are treated in the same manner as in Example 23 to give the desired camptothecin derivative (345 mg). The content of 10-(2'-aminoethyloxy)-7-ethyl-(20S)-camptothecin hydrochloride (the compound of Example 2) in the desired camptothecin derivative is 4.1% which is calculated on the basis of the absorbance at 380 nm. According to the GPC analysis, the average molecular weight of the desired camptothecin derivative is 169,000, and the degree of distribution (Mw/Mn) is 1.4.

EXAMPLE 26

Preparation of the camptothecin derivative of the following formula (SEQ ID No: 3):

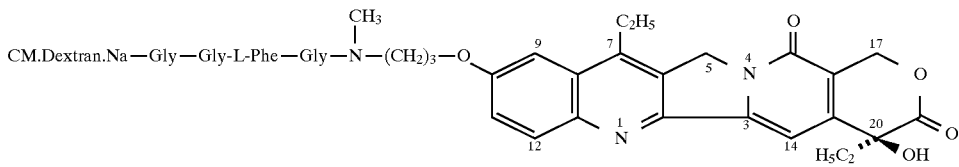

CM-Dextran sodium salt (CM-degree; 0.6) (1.0 g) and 10-[3'-N-(glycyl-glycyl-L-phenylalanyl-glycyl)-N-methylamino)propyloxy]-7-ethyl-(20S)-camptothecin hydrochloride (SEQ ID No: 3) (100 mg) which is obtained in Example 18 are treated in the same manner as in Example 23 to give the desired camptothecin derivative (943 mg). The content of 10-(3'-methylaminopropyloxy)-7-ethyl-(20S)-camptothecin hydrochloride (the compound of Example 7) in the desired camptothecin derivative is 3.3% which is calculated on the basis of the absorbance at 375 nm. According to the GPC analysis, the average molecular weight of the desired camptothecin derivative is 129,000, and the degree of distribution (Mw/Mn) is 2.4.

EXAMPLE 27

Preparation of the camptothecin derivative of the following formula (SEQ ID No: 1):

(20S)-camptothecin hydrochloride (150 mg) which is obtained in Example 20 are treated in the same manner as in Example 23 to give the desired camptothecin derivative (1100 mg) as a pale yellow powder. The content of 10-(3'-aminopropyloxy)-7-ethyl-(20S)-camptothecin hydrochloride (the compound of Example 1-(8-1)) in the desired camptothecin derivative is 2.9% which is calculated on the basis of the absorbance at 380 nm. According to the GPC analysis, the average molecular weight of the desired camptothecin derivative is 149,000, and the degree of distribution (Mw/Mn) is 1.53.

EXAMPLE 29

Preparation of the camptothecin derivative of the following formula:

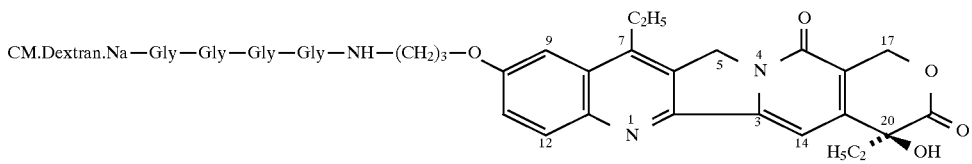

CM-Dextran sodium salt (CM-degree; 0.5) (1.2 g) and 10-(3'-(glycyl-glycyl-glycyl-glycylamino)propyloxy)-7-ethyl-(20S)-camptothecin hydrochloride (SEQ ID No: 1) (160 mg) which is obtained in following Example 43 are treated in the same manner as in Example 22 to give the desired camptothecin derivative (1125 mg) as a pale yellow powdery complex. The content of 10-(3'-aminopropyloxy)-7-ethyl-(20S)-camptothecin hydrochloride in the desired camptothecin derivative is 5.3% which is calculated on the basis of the absorbance at 380 nm. According to the GPC analysis, the average molecular weight of the desired camptothecin derivative is 155,000, and the degree of distribution (Mw/Mn) is 1.46.

EXAMPLE 28

Preparation of the camptothecin derivative of the following formula:

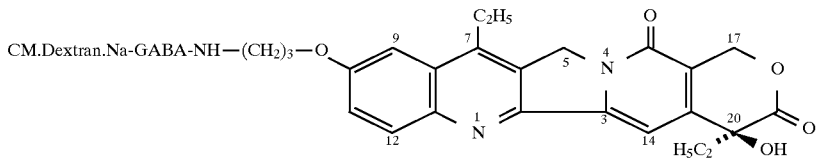

[GABA: γ-aminobutyric acid]

CM-Dextran sodium salt (CM-degree; 0.45) (1154 mg) and 10-[3'-(γ-aminobutyroylamino)propyloxy]-7-ethyl- CM.Dextran.Na-GABA-GABA-NH—(CH₂)₃—O 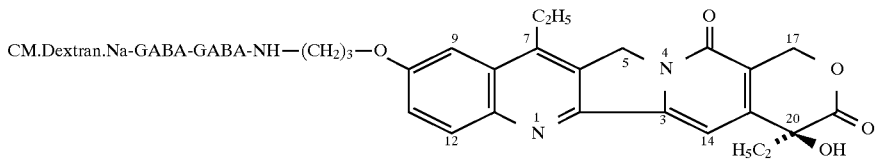

[GABA: γ-aminobutyric acid]

CM-Dextran sodium salt (CM-degree; 0.45) (1359 mg) is dissolved with stirring in water (80 ml), and thereto is added 10-[3'-{(N-(γ-aminobutyroyl)-γ-aminobutyroyl) amino}propyloxy]-7-ethyl-(20S)-camptothecin hydrochloride (135 mg) which is obtained in Example 21 under ice-cooling. To the mixture are added successively DMF (45 ml) and EEDQ (2-ethoxy-1-ethoxycarbonyl-1,2-dihydroquinoline) (2755 mg). The mixture is stirred at room temperature for 16 hours, and poured into ethanol (600 ml), and thereto is added 3M aqueous sodium chloride solution (3 ml). The precipitates are collected by centrifugation, dissolved in water (150 ml), and passed through a cation exchange column (AGMP-50, Na-type, manufactured by Bio-Rad, Laboratories, Ltd.). The main fractions are combined, filtered on a filter (0.22 μm), and purified by precipitation with using ethanol (4 times volume) and 3M aqueous sodium chloride solution. The precipitates are dissolved in water, and then the procedures of the filtration on a filter and the precipitation with ethanol are repeated. The precipitates thus obtained are washed successively with 90% ethanol, 99.5% ethanol, acetone, and ether, and dried under reduced pressure to give the desired camptothecin derivative (1254 mg) as a pale yellow powder. The content of 10-(3'-aminopropyloxy)-7-ethyl-(20S)-camptothecin hydrochloride (the compound of Example 1-(8-1)) in the desired camptothecin derivative is 4.9% which is calculated on the basis of the absorbance at 380 nm. According to the GPC analysis, the average molecular weight of the desired camptothecin derivative is 147,000, and the degree of distribution (Mw/Mn) is 1.63.

EXAMPLE 30

Preparation of the camptothecin derivative of the following formula:

CM.Pullulan.Na-L-Phe—Gly—NH—(CH₂)₃—O 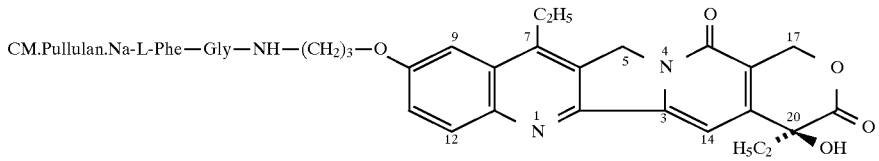

[CM.Pullulan.Na: carboxymethylpullulan sodium salt]

CM-Pullulan sodium salt (CM-degree; 0.5) (616 mg) and 10-[3'-(L-phenylalanyl-glycylamino)propyloxy]-7-ethyl-(20S)-camptothecin hydrochloride (63 mg) which is obtained in Example 11 are treated in the same manner as in Example 23 to give the desired camptothecin derivative (543 mg) as a pale yellow powder. The content of 10-(3'-aminopropyloxy)-7-ethyl-(20S)-camptothecin hydrochloride (the compound of Example 1-(8-1)) in the desired camptothecin derivative is 4.7% which is calculated on the basis of the absorbance at 380 nm. According to the GPC analysis, the average molecular weight of the desired camptothecin derivative is 190,000, and the degree of distribution (Mw/Mn) is 1.8.

EXAMPLE 31

Preparation of 10-(3'-hydroxypropyloxy)-7-ethyl-(20S)-camptothecin (1) Preparation of 5-[3'-(tert-butyldimethylsilyloxy) propyloxy]-2-nitrobenzaldehyde 5-Hydroxy-2-nitrobenzaldehyde dimethyl acetal (5.33 g) is dissolved in dry DMF (50 ml), and thereto are added potassium carbonate (6.91 g), sodium iodide (7.5 g) and 3-chloropropanol (4.73 g), and the mixture is stirred at 70° C. for 22 hours. To the mixture is added ethyl acetate, and the insoluble materials are removed by filtration. The filtrate is concentrated under reduced pressure, and the residue is purified by silica gel column chromatography to give 5-(3'-hydroxypropyloxy)-2-nitrobenzaldehyde dimethyl acetal (6.39 g) as a pale yellow oil.

Yield: 93%

NMR (300 MHz, CDCl₃): $\delta^{TMS}$=1.60 (1H, t, J=5 Hz), 2.08 (2H, quintet, J=6 Hz), 3.44 (6H, s), 3.87 (2H, q, J=6 Hz), 4.22 (2H, t, J=6 Hz), 6.01 (1H, s), 6.91 (1H, dd, J=9 Hz, 3 Hz), 7.31 (1H, d, J=3 Hz), 7.97 (1H, dd, J=9 Hz)

5-(3'-Hydroxypropyloxy)-2-nitrobenzaldehyde dimethyl acetal (6.35 g) is added to 70% acetic acid, and the mixture is stirred at 60° C. for 1.5 hour. The mixture is concentrated under reduced pressure, and the residue is washed with a saturated aqueous sodium hydrogen carbonate solution and a saturated sodium chloride solution, dried, and concentrated under reduced pressure. The residue is dissolved in dry DMF (50 ml), and thereto are added t-butyidimethylsilyl chloride (4.55 g) and imidazole (3.42 g), and the mixture is stirred at room temperature for two hours. The mixture is concentrated under reduced pressure, and the residue is purified by silica gel column chromatography to give 5-[3'-(t-butyidimethylsilyloxy)propyloxy]-2-nitrobenzaldehyde (5.82 g) as a pale yellow oil.

Yield: 73%

IR (Neat): $v_{max}^{cm-1}$=1700

Mass: m/z=340 (M+H⁺)

NMR (300 MHz, CDCl₃): $\delta^{TMS}$=0.04 (6H, s), 0.88 (9H, s), 2.03 (2H, quintet, J=6 Hz), 3.80 (2H, t, J=6 Hz), 4.22 (2H, t, J=6 Hz), 7.14 (1H, dd, J=9 Hz, 3 Hz), 7.33 (1H, d, J=3 Hz), 8.16 (1H, d, J=9 Hz), 10.49 (1H, s)

(2) Preparation of 1-{5'-[3"-(t-butyldimethylsilyloxy) propyloxy]-2'-nitrophenyl}-2-propen-1-one 5-[3'-(t-Butyidimethylsilyloxy)propyloxy]-2-nitrobenzaldehyde (5.80 g) is dissolved in dry THF (35 ml), and thereto is added with stirring vinyl-magnesium bromide (1.7 equivalent) in THF solution in a dry ice-acetone bath. The mixture is stirred for two hours, and thereto is added 5% hydrochloric acid (30 ml). The mixture is stirred at room temperature, extracted with ethyl acetate, and purified by silica gel column chromatography to give 1-{5'-[3"-(t-butyldimethylsilyloxy)propyloxy]-2'-nitrophenyl}-2-propen-1-ol (5.02 g).

Yield: 80%
IR (Nujol): $v_{max}^{cm-1}$=3420
Mass: m/z=390 (M+Na$^+$)
NMR (300 MHz, CDCl$_3$): $\delta^{TMS}$=0.04 (6H, s), 0.88 (9H, s), 2.00 (2H, quintet, J=6 Hz), 2.67 (1H, brs), 3.80 (2H, t, J=6 Hz), 4.16 (2H, t, J=6 Hz), 5.24 (1H, dd, J=10.5 Hz, 1.5 Hz), 5.41 (1H, dd, J=17 Hz, 1.5 Hz), 5.90 (1H, d, J=5 Hz), 6.08 (1H, ddd, J=17 Hz, 10.5 Hz, 1.5 Hz), 6.87 (1H, dd, J=9 Hz, 3 Hz), 7.24 (1H, d, J=3 Hz), 8.04 (1H, d, J=9 Hz)

1-{5'-[3"-(t-Butyldimethylsilyloxy)propyloxy]-2'-nitrophenyl}-2-propen-1-ol (4.98 g) is dissolved in chloroform (140 ml), and thereto is added active manganese dioxide (36 g), and the mixture is heated with stirring for six hours. The insoluble materials are removed by filtration, and the filtrate is concentrated, and the residue is purified by silica gel column chromatography to give 1-{5'-[3"-(t-butyidimethylsilyloxy)propyloxy]-2'-nitrophenyl}-2-propen-1-one (2.87 g).

Yield: 58%
IR (Nujol): $v_{max}^{cm-1}$=1680
Mass: m/z=364 (M+H$^+$)
NMR (300 MHz, d$_6$-DMSO): $\delta^{TMS}$=0.01 (6H, s), 0.84. (9H, s), 1.93 (2H, quintet, J=6 Hz), 3.75 (2H, t, J=6 Hz), 4.22 (2H, t, J=6 Hz), 5.85 (1H, d, J=17.5 Hz), 6.15 (1H, d, J=10.5 Hz), 6.65 (1H, dd, J=17.5 Hz, 10.5 Hz), 7.04 (1H, d, J=3 Hz), 7.25 (1H, dd, J=9 Hz, 3 Hz), 8.22 (1H, d, J=9 Hz)

(3) Preparation of 10-(3'-hydroxypropyloxy)-7-ethyl-(20S)-camptothecin

1-{5'-[3"-(t-Butyidimethylsilyloxy)propyloxy]-2'-nitrophenyl}-2-propen-1-one (765 mg) is dissolved in ethanol (10 ml), and thereto is added 10% palladium-carbon (156 mg), and the mixture is stirred at room temperature under atmospheric pressure of hydrogen gas. The catalyst is removed by filtration, and the filtrate is concentrated under reduced pressure. The residue is dissolved in ethanol (20 ml), and thereto are added (4S)-7,8-dihydro-4-ethyl-4-hydroxy-1H-pyrano[3,4-f]indolidin-3,6,10(4H)-trione (220 mg) and p-toluenesulfonic acid (32 mg), and the mixture is refluxed. After the reaction is completed, the mixture is concentrated under reduced pressure, and the residue is purified by silica gel column chromatography to give 7-ethyl-10-(3'-hydroxypropyloxy)-(20S)-camptothecin (343 mg) as a pale yellow powder.

M.p.: 233.5°–234.5° C.
Yield: 91%
IR (Nujol): $v_{max}^{cm-1}$=3380, 1750, 1645
Mass: m/z=451 (M+H$^+$)
NMR (300 MHz, d$_6$-DMSO): $\delta^{TMS}$=0.89 (3H, t, J=7.5Hz), 1.31 (3H, t, J=7.5 Hz), 1.76–1.95 (2H, m), 1.97 (1H, quintet, J=6.5 Hz), 3.17 (2H, q, J=7.5 Hz), 3.63 (2H, dt, J=6.5 Hz, 5 Hz), 4.26 (2H, t, J=6.5 Hz), 4.62 (1H, t, J=5 Hz), 5.25 (2H, s), 5.42 (2H, s), 6.49 (1H, s), 7.26 (1H, s), 7.45–7.51 (2H, m), 8.05 (1H, d, J=9.5 Hz)

EXAMPLE 32

Preparation of 10-(2'-hydroxyethyloxy)-7-ethyl-(20S)-camptothecin (1) Preparation of 1-{5'-[2"-(tert-butyidimethylsilyloxy)ethyloxy]-2'-nitrophenyl}-2-propen-1-one 1-{5'-[2"-(tert-Butyidimethylsilyloxy)ethyloxy]-2'-nitrophenyl}-2-propen-1-one is obtained in the same manner as in Example 31-(1) and (2).

IR (Nujol): $v_{max}^{cm-1}$=1680
Mass: m/z=352 (M+H+)
NMR(300 MHz, CDCl$_3$): $\delta^{TMS}$=0.09 (6H, s), 0.90 (9H, s), 3.99 (2H, t, J=5 Hz), 4.16 (2H, t, J=5 Hz), 5.84 (1H, d, J=17.5 Hz), 6.01 (1H, d, J=11 Hz), 6.62 (1H, dd, J=17.5 Hz, 11 Hz), 6.84 (1H, d, J=3 Hz), 7.06 (1H, dd, J=10 Hz, 3 Hz), 8.17 (1H, d, J=9 Hz)

(2) Preparation of 10-(2'-hydroxyethyloxy)-7-ethyl-(20S)-camptothecin 10-(2'-Hydroxyethyloxy)-7-ethyl-(20S)-camptothecin is obtained in the same manner as in Example 31-(3).

M.p.: 251°–254° C.
IR (Nujol): $v_{max}^{cm-1}$=3470, 1730, 1655
Mass: m/z=436 (M+H$^+$)
NMR (300 MHz, d6-DMSO): $\delta^{TMS}$=0.88 (3H, t, J=7.5 Hz), 1.31 (3H, t, J=7.5 Hz), 1.80–1.93 (2H, m), 3.17 (2H, q, J=7.5Hz), 3.83 (2H, q, J=5 Hz), 4.23 (2H, t, J=5 Hz), 4.96 (1H, t, J=5.5 Hz), 5.27 (2H, s), 5.42 (2H, s), 6.49 (1H, s), 7.26 (1H, s), 7.49–7.51 (2H, m), 8.06 (1 H, d, J=9 Hz)

EXAMPLE 33

Preparation of 10-[2'-(2"-hydroxyethyloxy) ethyloxy]-7-ethyl-(20S)-camptothecin (1) Preparation of 1-{5'-[2"-(2'"-(tert-butyidimethylsilyloxy)ethyloxy)ethyloxy]-2'-nitrophenyl}-2-propen-1-one 1-{5'-[2"-(2'"-(tert-Butyldimethylsilyloxy)ethyloxy)ethyloxy]-2'-nitrophenyl}-2-propen-1-one is obtained in the same manner as in Example 31-(1) and (2).

IR (Nujol): $v_{max}^{cm-1}$1680
Mass: m/z=396 (M+H$^+$)
NMR (300 MHz, CDCl$_3$): $\delta^{TMS}$=0.06 (6H, s), 0.89 (9H, s), 3.62 (2H, t, J=6 Hz), 3.75 (2H, t, J=6 Hz), 3.87–3.92 (2H, m), 4.20–4.25 (2H, m), 5.83 (1H, d, J=17.5 Hz), 6.01 (1H, d, J=10.5 Hz), 6.62 (1H, dd, J=17.5 Hz, 10.5 Hz), 6.84 (1H, d, J=3 Hz), 7.05 (1H, dd, J=9 Hz, 3 Hz), 8.17 (1H, d, J=9 Hz)

(2) Preparation of 10-[2'-(2"-hydroxyethyloxy)ethyloxy]-7-ethyl-(20S)-camptothecin 10-[2'-(2"-Hydroxyethyloxy)ethyloxy]-7-ethyl-(20S)-camptothecin is obtained in the same manner as in Example 31-(3) from 1-[5'-[2"-(2'"-(tert-butyldimethylsilyloxy)ethyloxy)ethyloxy]-2'-nitrophenyl)-2-propen-1-one.

M.p.: 230°–231.5° C. (decomposed)
IR (Nujol): $v_{max}^{cm-1}$=1735, 1655
Mass: m/z=481 (M+H$^+$)
NMR (300 MHz, d$_6$-DMSO): $\delta^{TMS}$=0.88 (3H, t, J=7.5 Hz), 1.31 (3H, t, J=7.5 Hz), 1.79–1.94 (2H, m), 3.18 (2H, q, J=7.5 Hz), 3.55 (4H, m), 3.86 (2H, m), 4.34 (2H, m), 4.63 (1H, brs), 5.27 (2H, s), 5.42 (2H, s), 6.48 (1H, s), 7.26 (1H, s), 7.48–7.54 (2H, m), 8.06 (1H, d, J=10 Hz)

EXAMPLE 34

Preparation of 10-[3'-(L-alanyloxy)propyloxy]-7-ethyl-(20S)-camptothecin hydrochloride (1) Preparation of 1-[5'-(3"-hydroxypropyloxy)-2'-nitrophenyl]-2-propen-1-one 1-(5'-[3"-(t-Butyldimethylsilyloxy)propyloxy]-2'-nitrophenyl]-2-propen-1-one (the compound of Example 31-(2)) (1.84 g) is mixed with THF (20 ml) and 50% aqueous acetic acid solution (30 ml), and the mixture is stirred at room temperature overnight. The reaction solution is concentrated under reduced pressure, and the residue is purified by silica gel column chromatography to give 1-[5'-(3"-hydroxypropyloxy)-2'-nitrophenyl]-2-propen-1-one (1.26 g).

Yield: 95%

IR (Neat): $\nu_{max}^{cm-1}$=3420, 1675

Mass: m/z=251 (M$^+$)

NMR (300 MHz, CDCl$_3$): $\delta^{TMS}$=2.08 (3H, m), 3.86 (2H, t, J=6 Hz), 4.23 (2H, t, J=6 Hz), 5.89 (1H, d, J=17.5 Hz), 6.02 (1H, d, J=10.5 Hz), 6.62 (1H, dd, J=17.5 Hz, 10.5 Hz), 6.84 (1H, d, J=3 Hz), 7.04 (1H, dd, J=9 Hz, 3 Hz), 8.17 (1H, d, J=9 Hz)

(2) Preparation of 1-[5'-(3"-t-butoxycarbonyl-L-alanyloxy-propyloxy)-2'-nitrophenyl]-2-propen-1-one 1-[5'-(3"-Hydroxypropyloxy)-2'-nitrophenyl]-2-propen-1-one (1.22 g) and t-butoxycarbonyl-L-alanine (2.76 g) are dissolved in THF (50 ml), and thereto is added with stirring DCC (3.01 g) under ice-cooling. The mixture is reacted at room temperature, and the reaction solution is filtered, concentrated under reduced pressure, and the residue is purified by silica gel column chromatography to give 1-[5'-(3"-t-butoxycarbonyl-L-alanyloxy-propyloxy)-2'-nitrophenyl]-2-propen-1-one (1.19 g).

Yield: 58%

IR (Neat): $\nu_{max}^{cm-1}$=3370, 1740, 1715

Mass: m/z=423 (M+H$^+$)

NMR (300 MHz, CDCl$_3$): $\delta^{TMS}$=1.38 (3H, d, J=7 Hz), 1.43 (9H, s), 2.19 (2H, quintet, J=6 Hz), 4.16 (2H, t, J=6 Hz), 4.27–4.42 (3H, m), 4.98 (1H, m), 5.85 (1H, d, J=1 7.5 Hz), 6.02 (1H, d, J=11 Hz), 6.62 (1H, dd, J=17.5 Hz, 11 Hz), 6.82 (1H, d, J=3 Hz), 7.04 (1H, dd, J=9 Hz, 3 Hz), 8.17 (1H, d, J=9 Hz)

(3) Preparation of 10-[3'-(t-butoxycarbonyl-L-alanyloxy)propyloxy]-7-ethyl-(20S)-camptothecin 1-{5'-[3"-(t-Butoxycarbonyl-L-alanyloxy)propyloxy]-2'-nitrophenyl}-2-propen-1-one (1.17 g) is dissolved in ethanol (30 ml), and thereto is added 10% palladium-carbon (206 mg), and the mixture is stirred at room temperature under atmospheric pressure of hydrogen gas. The catalyst is removed by filtration, and the filtrate is concentrated. The residue is dissolved in ethanol (30 ml), and thereto are added (4S)-7,8-dihydro-4-ethyl-4-hydroxy-1H-pyrano-[3,4-f]-indolidine-3,6,10(4H)-trione (290 mg) and p-toluenesulfonic acid (10 mg), and the mixture is refluxed. After the reaction is completed, the mixture is concentrated under reduced pressure, and the residue is purified by silica gel column chromatography to give 10-[3'-(t-butoxycarbonyl-L-alanyloxy)propyl-oxy]- 7-ethyl-(20S)-camptothecin (257 mg) as a pale yellow powder.

M.p.: >180° C. (decomposed)

Yield: 38%

IR (Nujol): $\nu_{max}^{cm-1}$=3280, 1760, 1715, 1660

Mass: m/z=622 (M+H$^+$)

NMR (300 MHz, d$_6$-DMSO): $\delta^{TMS}$=0.88 (3H, t, J=7.5 Hz), 1.25 (3H, t, J=7.5 Hz), 1.32 (3H, t, J=7.5 Hz), 1.35 (9H, s), 1.78–1.95 (2H, m), 2.08–2.20 (2H, m), 3.19 (2H, q, J=7.5 Hz), 3.28–3.34 (2H, m), 4.20–4.37 (3H, m), 5.30 (2H, s), 5.43 (2H, s), 6.50 (1H, s), 7.27 (1H, s), 7.30 (1H, d, J=7.5 Hz), 7.48–7.54 (2H, m), 8.08 (1H, d, J=9.5 Hz)

(4) Preparation of 10-[3'-(L-alanyloxy)propyloxy]-7-ethyl-(20S)-camptothecin hydrochloride 10-[3'-(t-Butoxycarbonyl-L-alanyloxy)propyloxy]-7-ethyl-(20S)-camptothecin (240 mg) is dissolved in dioxane (2 ml), and.thereto is added with stirring hydrochloric acid-dioxane (4 ml) under ice-cooling. After the reaction is completed, to the mixture is added diisopropyl ether (30 ml). The precipitates are collected by filtration to give 10-[3'-(L-alanyloxy)propyloxy]-7-ethyl-(20S)-camptothecin hydrochloride (183 mg) as a pale yellow powder.

Yield: 87%

IR (Nujol): $\nu_{max}^{cm-1}$=3375, 1750, 1660

Mass: m/z=522 [(M−Cl$^-$)$^+$]

NMR (300 MHz, d$_6$-DMSO): $\delta^{TMS}$=0.88 (3H, t, J=7.5 Hz), 1.32 (3H, t, J=7.5 Hz), 1.44 (3H, t, J=7 Hz), 1.76–1.94 (2H, m), 2.20 (1H, quintet, J=6 Hz), 3.20 (2H, q, J=7.5 Hz), 4.05–4.20 (1H, m), 4.34 (2H, t, J=6 Hz), 4.40 (2H, t, J=6 Hz), 5.29 (2H, s), 5.43 (2H, s), 7.28 (1H, s), 7.49–7.55 (2H, m), 8.08 (1H, d, J=10 Hz), 8.52–8.73 (3H, m)

EXAMPLE 35

Preparation of 10-[2'-(L-alanyloxy)ethyloxy]-7-ethyl-(20S)-camptothecin hydrochloride (1) Preparation of 1-{5'-[2"-(t-butoxycarbonyl-L-alanyloxy)ethyloxy]-2'-nitrophenyl}-2-propen-1-one 1-{5'-[2"-(t-Butoxycarbonyl-L-alanyloxy)ethyloxy]-2'-nitrophenyl}-2-propen-1-one is obtained in the same manner as in Example 34-(1) and (2).

IR (Nujol): $\nu_{max}^{cm-1}$=3370, 1750, 1715

Mass: m/z=409 (M+H$^+$)

NMR (300 MHz, CDCl$_3$): $\delta^{TMS}$=1.39 (3H, d, J=7.5 Hz), 1.43 (9H, s), 4.29–4.35 (3H, m), 4.53 (2H, brt), 5.00 (1H, br), 5.85 (1H, d, J=17 Hz), 6.03 (1H, d, J=10.5 Hz), 6.63 (1H, dd, J=17.5 Hz, 10.5 Hz), 6.84 (1H, d, J=3 Hz), 7.06 (1H, dd, J=9 Hz, 3 Hz), 8.18 (1H, d, J=9 Hz)

(2) Preparation of 10-[2'-(t-butoxycarbonyl-L-alanyloxy)ethyloxy]-7-ethyl-(20S)-camptothecin 10-[2'-(t-Butoxycarbonyl-L-alanyloxy)ethyloxy]-7-ethyl-(20S)-camptothecin is obtained in the same manner as in Example 34-(3).

M.p.: 114°–120° C.

IR (Nujol): $\nu_{max}^{cm-1}$=3320, 1750, 1710, 1660

Mass: m/z=608 (M+H$^+$)

NMR (300 MHz, d$_6$-DMSO): $\delta^{TMS}$=0.88 (3H, t, J=7.5Hz), 1.26 (3H, d, J=7.5 Hz), 1.31 (3H, t, J=7.5 Hz), 1.35 (9H, s), 1.80–1.94 (2H, m), 3.19 (2H, q, J=7.5 Hz), 3.99–4.10 (1H, m), 4.43–4.56 (4H, m), 5.29 (2H, s), 5.43 (2H, s), 6.49 (1H, s), 7.27 (1H, s), 7.32 (1H, d, J=7 Hz), 7.49–7.53 (2H, m), 8.08 (1H, d, J=10 Hz)

(3) Preparation of 10-[2'-(L-alanyloxy)ethyloxy]-7-ethyl (20S)-camptothecin hydrochloride 10-[2'-(L-Alanyloxy)ethyloxy]-7-ethyl-(20S)-camptothecin hydrochloride is obtained in the same manner as in Example 34-(4).

M.p.: >180° C. (decomposed)

IR (Nujol): $\nu_{max}^{cm-1}$=3680, 1750, 1655

Mass: m/z=508 [(M−Cl$^-$)$^+$]

NMR (300 MHz, d$_6$-DMSO): $\delta^{TMS}$=0.88 (3H, t, J=7.5 Hz), 1.32 (3H, t, J=7.5 Hz), 1.45 (3H, d, J=7 Hz), 1.80–1.94 (2H, m), 3.21 (2H, q, J=7.5 Hz), 4.10–4.19 (1H, m), 4.50 (2H, m), 4.60–4.65 (2H, m), 5.30 (2H, s), 5.43 (2H, s), 7.29 (1H, s), 7.51–7.55 (2H, m), 8.10 (1H, d, J=9.5 Hz), 8.56–8.68 (3H, m)

EXAMPLE 36

Preparation of 10-{2'-[2"-(L-alanyloxy)ethyloxy]ethyloxy}-7-ethyl-(20S)-camptothecin hydrochloride (1) Preparation of 10-{5'-[2"-(2'''-(t-butoxycarbonyl-L-alanyloxy)ethyloxy)-ethyloxy]-2'-nitrophenyl}-2-propen-1-one 10-{5'-[2"-(2'''-(t-Butoxycarbonyl-L-alanyloxy)ethyloxy)ethyloxy]-2'-nitrophenyl}-2-propen-1-one is obtained in the same manner as in Example 34-(1) and (2).

IR (Nujol): $v_{max}^{cm-1}$=3385, 1755, 1690

Mass: m/z=453 (M+H$^+$)

NMR (300 MHz, CDCl$_3$): $\delta^{TMS}$=1.38 (3H, d, J=7 Hz), 1.44 (9H, s), 3.74–3.79 (2H, m), 3.85–3.90 (2H, m), 4.21–4.25 (2H, m), 4.29–4.35 (3H, m), 5.03 (1H, br), 5.84 (1H, d, J=17 Hz), 6.02 (1H, d, J=11 Hz), 6.62 (1H, dd, J=17.5 Hz, 11 Hz), 6.85 (1H, d, J=3 Hz), 7.07 (1H, dd, J=9Hz, 3Hz), 8.17 (1H, d, J=9 Hz)

(2) Preparation of 10-{2'-[2"-(t-butoxycarbonyl-L-alanyloxy)ethyloxy]ethyloxy}-7-ethyl-(20S)-camptothecin 10-{2'-[2"-(t-Butoxycarbonyl-L-alanyloxy)ethyloxy]ethyloxy}-7-ethyl-(20S)-camptothecin is obtained in the same manner as in Example 34-(3).

M.p.: >164° C. (decomposed)

IR (Nujol): $v_{max}^{cm-1}$=3380, 1750, 1705, 1655

Mass: m/z=652 (M+H$^+$)

NMR (300 MHz, d$_6$-DMSO): $\delta^{TMS}$=0.88 (3H, t, J=7.5 Hz), 1.22 (3H, t, J=7.5 Hz), 1.31 (3H, t, J=7.5 Hz), 1.37 (9H, s), 1.75–1.94 (2H, m), 3.18 (2H, q, J=7.5 Hz), 3.73 (2H, t, J=7 Hz), 3.87 (2H, t, J=7 Hz), 3.94–4.05 (1H, m), 4.10–4.35 (4H, m), 5.29 (2H, s), 5.42 (2H, s), 6.48 (1 H, s), 7.27 (1H, s), 7.27 (1H, d, J=6 Hz), 7.47–7.54 (2H, m), 8.07 (1H, d, J=10 Hz)

(3) Preparation of 10-{2'-[2"-(L-alanyloxy)ethyloxy]ethyloxy}-7-ethyl-(20S)-camptothecin hydrochloride 10-{2'-[2"-(L-Alanyloxy]ethyloxylethyloxy}-7-ethyl-(20S)-camptothecin hydrochloride is obtained in the same manner as in Example 34-(4).

M.p.: >180° C. (decomposed)

IR (Nujol): $v_{max}^{cm-1}$=3380, 1760, 1740, 1660

Mass: m/z=552 [(M-Cl$^-$)$^+$]

NMR (300 MHz, d$_6$-DMSO): $\delta^{TMS}$=0.8$_8$ (3H, t, J=7.5 Hz), 1.31 (3H, t, J=7.5 Hz), 1.41 (3H, d, J=7 Hz), 1.79–1.94 (2H, m), 3.19 (2H, q, J=7.5 Hz), 3.78 (2H, t, J=7 Hz), 3.89 (2H, t, J=7 Hz), 4.00–4.15 (1H, m), 4.26–4.44 (4H, m), 5.29 (2H, s), 5.43 (2H, s), 7.28 (1H, s), 7.49–7.55 (2H, m), 8.08 (1H, d, J=10 Hz), 8.52–8.70 (3H, m)

EXAMPLE 37

Preparation of 10-[3'-(L-prolyloxy)propyloxy]-7-ethyl-(20S)-camptothecin hydrochloride (1) Preparation of 1-{5'-[3"-(t-butoxycarbonyl-L-prolyloxy)propyloxy]-2'-nitrophenyl}-2-propen-1-one 1-{5'-[3"-(t-Butoxycarbonyl-L-prolyloxy)propyloxy]-2'-nitrophenyl}-2-propen-1-one is obtained in the same manner as in Example 34-(1) and (2).

IR (Neat): $v_{max}^{cm-1}$=1750, 1700

Mass: m/z=471 (M+Na$^+$)

NMR (300 MHz, CDCl$_3$): $\delta^{TMS}$=1.44 (9H, s), 1.81–2.30 (6H, m), 3.37–3.54 (2H, m), 4.13–4.37 (5H, m), 5.85 (1H, d, J=17.5 Hz), 6.01 (1H, d, J=10.5 Hz), 6.62 (1H, dd, J=17.5 Hz, 10.5 Hz), 6.82 (1H, d, J=3 Hz), 7.05 (1H, dd, J=9 Hz, 3 Hz), 8.17 (1H, d, J=9 Hz)

(2) Preparation of 10-[3'-(t-butoxycarbonyl-L-prolyloxy)propyloxy]-7-ethyl-(20S)-camptothecin 10-[3'-(t-Butoxycarbonyl-L-prolyloxy)propyloxy]-7-ethyl-(20S)-camptothecin is obtained in the same manner as in Example 34-(3) from 1-{5'-[3"-(t-butoxycarbonyl-L-prolyloxy)propyloxy]-2'-nitrophenyl}-2-propen-1-one as a pale yellow powder.

M.p.: 136°–139° C.

IR (Nujol): $v_{max}^{cm-1}$=3280, 1755, 1700, 1660

Mass: m/z=648 (M+H$^+$)

NMR (300 MHz, d$_6$-DMSO): $\delta^{TMS}$=0.88 (3H, t, J=7.5 Hz), 1.31 (3H, t, J=7.5 Hz), 1.36 (9H, s), 1.74–1.94 (6H, m), 2.10–2.28 (2H, m), 3.18 (2H, q, J=7.5 Hz), 3.27–3.40 (2H, m), 4.15–4.22 (1H, m), 4.24–4.37 (4H, m), 5.28 (2H, s), 5.42 (2H, s), 6.48 (1H, s), 7.27 (1H, s), 7.48–7.53 (2H, m), 8.07 (1H, d, J=9 Hz)

(3) Preparation of 10-[3'-(L-prolyloxy)propyloxy]-7-ethyl-(20S)-camptothecin hydrochloride 10-[3'-(L-Prolyloxy)propyloxy]-7-ethyl-(20S)-camptothecin hydrochloride is obtained in the same manner as in Example 34-(4) from 10-[3'-(t-butoxycarbonyl-L-prolyloxy)propyloxy]-7-ethyl-(20S)-camptothecin as a pale yellow powder.

IR (Nujol): $v_{max}^{cm-1}$=3680, 1750, 1660, 1620

Mass: m/z=548 [(M-Cl$^-$)$^+$]

NMR (300 MHz, d$_6$-DMSO): $\delta^{TMS}$=0.88 (3H, t, J=7 Hz), 1.32 (3H, t, J=7.5 Hz), 1.81–2.06 (6H, m), 2.19–2.34 (2H, m), 3.17–3.24 (4H, m), 4.05–4.20 (1H, m), 4.34 (2H, t, J=6 Hz), 4.42 (2H, t, J=6 Hz), 5.29 (2H, s), 5.43 (2H, s), 7.28 (1H, s), 7.50–7.55 (2H, m), 8.09 (1H, d, J=10 Hz), 9.00–9.20 (1H, m)

EXAMPLE 38

Preparation of 10-[2'-(L-prolyloxy)ethyloxy]-7-ethyl-(20S)-camptothecin hydrochloride (1) Preparation of 1-{5'-[2"-(t-butoxycarbonyl-L-prolyloxy)ethyloxy]-2'-nitrophenyl}-2-propen-1-one 1-{5'-[2"-(t-Butoxycarbonyl-L-prolyloxy)ethyloxy]-2'-nitrophenyl}-2-propen-1-one is obtained in the same manner as in Example 34-(1) and (2).

IR (Neat): $v_{max}^{cm-1}$=1750, 1700

Mass: m/z=435 (M+H$^+$)

NMR (300 MHz, CDCl$_3$): $\delta^{TMS}$=1.44 (9H, s), 1.86–2.29 (4H, m), 3.37–3.57 (2H, m), 4.25–4.35 (3H, m), 4.48–4.53 (2H, m), 5.85 (1H, d, J=17.5 Hz), 6.02 (1H, d, J=10.5 Hz), 6.63 (1H, dd, J=17.5 Hz, 10.5 Hz), 6.83 (1H, d, J=3.5 Hz), 7.04 (1H, dd, J=9 Hz, 3 Hz), 8.18 (1H, d, J=9 Hz)

(2) Preparation of 10-[2'-(t-butoxycarbonyl-L-prolyloxy)ethyloxy]-7-ethyl-(20S)-camptothecin 10-[2'-(t-Butoxycarbonyl-L-prolyloxy)ethyloxy]-7-ethyl-(20S)-camptothecin is obtained in the same manner as in Example 34-(3).

M.p.: 203°–205° C. (decomposed)

IR (Nujol): $v_{max}^{cm-1}$=1755, 1735,1685, 1670, 1610

Mass: m/z=634 (M+H$^+$)

NMR (300 MHz, d$_6$-DMSO): $\delta^{TMS}$=0.88 (3H, t, J=7.5 Hz), 1.31 (3H, t, J=7.5 Hz), 1.37 (9H, s), 1.79–1.94 and 2.16–2.26 (6H, m), 3.19 (2H, q, J=7.5 Hz), 3.28–3.40 (2H, m), 4.20–4.24 (1H, m), 4.45–4.56 (4H, m), 5.29 (2H, s), 5.43 (2H, s), 6.48 (1H, s), 7.27 (1H, s), 7.46–7.53 (2H, m), 8.08 (1H, d, J=9.5 Hz)

(3) Preparation of 10-[2'-(L-prolyloxy)ethyloxy]-7-ethyl-(20S)-camptothecin hydrochloride 10-[2'-(L-Prolyloxy)ethyloxy]-7-ethyl-(20S)-camptothecin hydrochloride is obtained in the same manner as in Example 34-(4).

M.p.: >170° C. (decomposed)

IR (Nujol): $v_{max}^{cm-1}$=3680, 1750, 1655

Mass: m/z=534 [(M–Cl$^-$)$^+$]

NMR (300 MHz, d$_6$-DMSO): $\delta^{TMS}$=0.88 (3H, t, J=7.5 Hz), 1.32 (3H, t, J=7.5 Hz), 1.80–2.09 and 2.23–2.35 (6H, m), 3.17–3.29 (4H, m), 4.40–4.47 (1H, m), 4.52 (2H, m), 4.62–4.69 (2H, m), 5.30 (2H, s), 5.43 (2H, s), 7.29 (1H, s), 7.51–7.55 (2H, m), 8.10 (1H, d, J=9.5 Hz), 9.03–9.23 and 10.23–10.43 (2H, m)

EXAMPLE 39

Preparation of 10-{2'-[2''-(L-prolyloxy)ethyloxy]ethyloxy}-7-ethyl-(20S)-camptothecin hydrochloride (1) Preparation of 1-{5'-[2''-(2'''-(t-butoxycarbonyl-L-prolyloxy)ethyloxy)-ethyloxy]-2'-nitrophenyl}-2-propen-1-one 1-{5'-[2''-(2'''-(t-Butoxycarbonyl-L-prolyloxy)ethyloxy)ethyloxy]-2'-nitrophenyl}-2-propen-1-one is obtained in the same manner as in Example 34-(1) and (2).

IR (Neat): $v_{max}^{cm-1}$=1750, 1700

Mass: m/z=479 (M+H$^+$)

NMR (300 MHz, CDCl$_3$): $\delta^{TMS}$=1.45 (9H, s), 1.79–2.30 (4H, m), 3.33–3.59 (2H, m), 3.77 (2H, t, J=5 Hz), 3.87 (2H, t, J=5 Hz), 4.19–4.26 (2H, m), 4.26–4.36 (3H, m), 5.84 (1H, d, J=18 Hz), 6.01 (1H, d, J=11 Hz), 6.62 (1H, dd, J=18 Hz, 11 Hz), 6.85 (1H, d, J=3 Hz), 7.06 (1H, dd, J=9 Hz, 3 Hz), 8.17 (1H, d, J=9 Hz)

(2) Preparation of 10-{2'-[2''-(t-butoxycarbonyl-L-propyloxy)ethyloxy]-ethyloxy}-7-ethyl-(20S)-camptothecin 10-{2'-[2''-(t-Butoxycarbonyl-L-propyloxy)ethyloxy]ethyloxy}-7-ethyl-(20S)-camptothecin is obtained in the same manner as in Example 34-(3) as a pale yellow powder.

IR (Nujol): $v_{max}^{cm-1}$=3370, 1750, 1700, 1655

Mass: m/z=678 (M+H$^+$)

NMR (300 MHz, d$_6$-DMSO): $\delta^{TMS}$=0.88 (3H, t, J=7.5 Hz), 1.31 (3H, t, J=7.5 Hz), 1.37 (9H, s), 1.69–1.85 (4H, m), 1.79–1.94 (2H, m), 3.18 (2H, q, J=7.5 Hz), 3.24–3.39 (2H, m), 3.69–3.77 (2H, m), 3.83–3.91 (2H, m), 4.12–4.21 (1H, m), 4.21–4.28 (2H, m), 4.30–4.38 (2H, m), 5.29 (2H, s), 5.43 (2H, s), 7.27 (1H, s), 7.47–7.54 (2H, m), 8.07 (1H, d, J=10 Hz)

(3) Preparation of 10-{2'-[2''-(L-prolyloxy)ethyloxy]ethyloxy}-7-ethyl-(20S)-camptothecin hydrochloride 10-{2'-[2''-(L-Prolyloxy)ethyloxy]ethyloxy}-7-ethyl-(20S)-camptothecin hydrochloride is obtained in the same manner as in Example 34-(4).

M.p.: >170° C. (decomposed)

IR (Nujol): $v_{max}^{cm-1}$=3370, 1750, 1660

Mass: m/z=578 [(M–Cl$^-$)$^+$]

NMR (300 MHz, d$_6$-DMSO): $\delta^{TMS}$=0.88 (3H, t, J=7.5 Hz), 1.31 (3H, t, J=7.5 Hz), 1.79–2.32 (6H, m), 3.12–3.28 (4H, m), 3.79 (2H, m), 3.89 (2H, m), 4.28–4.46 (5H, m), 5.28 (2H, s), 5.43 (2H, s), 7.30 (1 H, s), 7.49–7.54 (2H, m), 8.09 (1H, d, J=9.5 Hz), 8.95–9.32 (2H, m)

EXAMPLE 40

Preparation of 10-[3'-(O-ethyl-L-β-aspartyloxy)propyloxy]-7-ethyl-(20S)-camptothecin (the camptothecin derivative of the following formula) hydrochloride

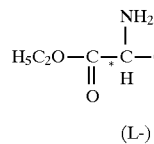 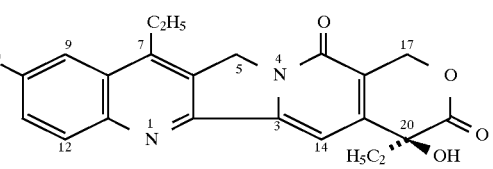

(1) Preparation of 1-{5'-[3''-(N-t-butoxycarbonyl-O-ethyl-L-β-aspartyloxy)-propyloxy]-2'-nitrophenyl}-2-propen-1-one 1-{5'-[3''- (N-t-Butoxycarbonyl-O-ethyl-L-β-aspartyloxy) propyloxy]-2'-nitrophenyl}-2-propen-1-one is obtained in the same manner as in Example 34-(1) and (2) as a pale yellow oil.

IR (Neat): $v_{max}^{cm-1}$=3370, 1740, 1715, 1680

NMR (300 MHz, CDCl$_3$): $\delta^{TMS}$=1.26 (3H, t, J=7 Hz), 1.44 (9H, s), 2.17 (2H, quintet, J=6 Hz), 2.84 (1H, dd, J=16.5 Hz, 5 Hz), 2.97 (1H, dd, J=16.5 Hz, 5 Hz), 4.15 (1H, t, J=5 Hz), 4.20 (4H, m), 4.29 (2H, t, J=6 Hz), 4.53–4.57 (1H, m), 5.43 (1H, d, J=8 Hz), 5.85 (1H, d, J=18 Hz), 6.02 (1H, d, J=11 Hz), 6.63 (1H, dd, J=18 Hz, 11 Hz), 6.83 (1H, d, J=3 Hz), 7.04 (1H, dd, J=9 Hz, 3 Hz), 8.18 (1H, d, J=9 Hz)

(2) Preparation of 10-[3'-(N-t-butoxycarbonyl-O-ethyl-L-β-aspartyloxy)-propyloxy]-7-ethyl-(20S)-camptothecin 10-[3'-(N-t-Butoxycarbonyl-O-ethyl-L-β-aspartyloxy) propyloxy]-7-ethyl-(20S)-camptothecin is obtained in the same manner as in Example 34-(3).

M.p.: 107°–110° C.

IR (Nujol): $v_{max}^{cm-1}$=3260, 1750, 1720, 1660, 1610

Mass: m/z=694 (M+H$^+$)

NMR (300 MHz, d$_6$-DMSO): $\delta^{TMS}$=0.88 (3H, t, J=7.5 Hz), 1.14 (3H, t, J=7 Hz), 1.32 (3H, t, J=7.5 Hz), 1.36 (9H, s), 1.80–1.94 (2H, m), 2.14 (2H, quintet, J=6 Hz), 2.68 (1H, dd, J=16 Hz, 8 Hz), 2.81 (1H, dd, J=16 Hz, 6 Hz), 3.19 (2H, q, J=7.5 Hz), 4.06 (2H, q, J=7 Hz), 4.23–4.33 (1 H, m), 4.37 (4H, m), 5.29 (2H, s), 5.43 (2H, s), 6.48 (1H, s), 7.27 (1H, s), 7.31 (1H, d, J=7 Hz), 7.50–7.53 (2H, m), 8.07 (1H, d, J=10 Hz)

(3) Preparation of 10-[3'-(O-ethyl-L-β-aspartyloxy)propyloxy]-7-ethyl-(20S)-camptothecin hydrochloride 10-[3'-(O-Ethyl-L-β-aspartyloxy)propyloxy]-7-ethyl-(20S)-camptothecin hydrochloride is obtained in the same manner as in Example 34-(4).

M.p.: >215° C. (decomposed)

IR (Nujol): $v_{max}^{cm-1}$=3690, 1750, 1660, 1620

Mass: m/z=594 [(M−Cl⁻)⁺]

NMR (300 MHz, d₆-DMSO): $\delta^{TMS}$=0.88 (3H, t, J=7.5 Hz), 1.18 (3H, t, J=7 Hz), 1.32 (3H, t, J=7.5 Hz), 1.80–1.94 (2H, m), 2.18 (2H, quintet, J=6 Hz), 3.00 (1H, dd, J=17.5 Hz, 6 Hz), 3.08 (1H, dd, J=17.5 Hz, 6 Hz), 3.20 (2H, q, J=7 Hz), 4.16 (1H, m), 4.30 (2H, t, J=6 Hz), 4.32 (2H, t, J=6 Hz), 5.30 (2H, s), 5.43 (2H, s), 7.28 (1H, s), 7.50–7.53 (2H, m), 8.09 (1H, d, J=10 Hz), 8.65–8.78 (3H, m)

EXAMPLE 41

Preparation of 10-[2'-(O-ethyl-L-β-aspartyloxy) ethyloxy]-7-ethyl-(20S)-camptothecin (the camptothecin derivative of the following formula) hydrochloride

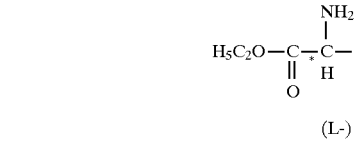
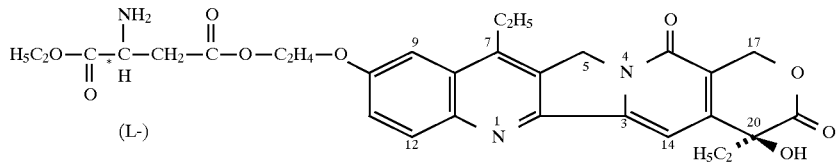

(1) Preparation of 1-{5'-[2''-(N-t-butoxycarbonyl-O-ethyl-L-β-aspartyloxy)-ethyloxy]-2'-nitrophenyl}-2-propen-1-one 1-{5'-[2''-(N-t-Butoxycarbonyl-O-ethyl-L-β-aspartyloxy)ethyloxy]-2'-nitrophenyl}-2-propen-1-one is obtained in the same manner as in Example 34-(1) and (2).

IR (Nujol): $v_{max}^{cm-1}$=3430, 1720, 1680

Mass: m/z=481 (M+H⁺)

NMR (300 MHz, CDCl₃): $\delta^{TMS}$=1.26 (3H, t, J=7 Hz), 1.44 (9H, s), 2.88 (1H, dd, J=17 Hz, 5 Hz), 3.02 (1H, dd, J=17 Hz, 5 Hz), 4.20 (2H, q, J=7 Hz), 4.27 (2H, m), 4.48 (2H, m), 4.55–4.61 (1H, m), 5.45 (1H, brd, J=8 Hz), 5.85 (1H, d, J=17.5 Hz), 6.02 (1H, d, J=10.5 Hz), 6.63 (1H, dd, J=17.5 Hz, 10.5 Hz), 6.85 (1H, d, J=3 Hz), 7.07 (1H, dd, J=9 Hz, 3 Hz), 8.19 (1H, d, J=9 Hz)

(2) Preparation of 10-[2'-(N-t-butoxycarbonyl-O-ethyl-L-p-aspartyloxy)ethyloxy]-7-ethyl-(20S)-camptothecin 10-[2'-(N-t-Butoxycarbonyl-O-ethyl-L-β-aspartyloxy)ethyloxy]-7-ethyl-(20S)-camptothecin is obtained in the same manner as in Example 34-(3).

M.p.: 111°–114° C. (decomposed)

IR (Nujol): $v_{max}^{cm-1}$=3310, 1745, 1720, 1655, 1605

Mass: m/z=680 (M+H⁺)

NMR (300 MHz, d₆-DMSO): $\delta^{TMS}$=0.88 (3H, t, J=7.5 Hz), 1.15 (3H, t, J=7 Hz), 1.31 (3H, t, J=7.5 Hz), 1.37 (9H, s), 1.80–1.94 (2H, m), 2.72 (1H, dd, J=16 Hz, 6 Hz), 2.84 (1H, dd, J=16 Hz, 6 Hz), 3.20 (2H, q, J=7.5 Hz), 4.07 (2H, q), 4.34–4.47 (5H, m), 5.29 (2H, s), 5.43 (2H, s), 6.48 (1H, s), 7.27 (1H, s), 7.29 (1H, d, J=9 Hz), 7.50–7.54 (2H, m), 8.08 (1H, d, J=10 Hz)

(3) Preparation of 10-[2'-(O-ethyl-L-β-aspartyloxy) ethyloxy]-7-ethyl-(20S)-camptothecin hydrochloride 10-[2'-(O-Ethyl-L-β-aspartyloxy)ethyloxy]-7-ethyl-(20S)-camptothecin hydrochloride is obtained in the same manner as in Example 34-(4).

M.p.: >160° C. (decomposed)

IR (Nujol): $v_{max}^{cm-1}$=3680, 1750, 1660, 1615

Mass: m/z=580 [(M−Cl⁻)⁺]

NMR (300 MHz, d₆-DMSO): $\delta^{TMS}$=0.88 (3H, t, J=7.5 Hz), 1.19 (3H, t, J=7 Hz), 1.32 (3H, t, J=7.5 Hz), 1.80–1.94 (2H, m), 3.03 (1H, dd, J=17.5 Hz, 6 Hz), 3.12 (1H, dd, J=17.5 Hz, 5.5 Hz), 3.21 (2H, q, J=7.5 Hz), 4.19 (2H, q, J=7.5 Hz), 4.36 (1H, brm), 4.47–4.53 (4H, m), 5.30 (2H, s), 5.43 (2H, s), 7.29 (1H, s), 7.51–7.54 (2H, m), 8.11 (1H, d, J=10 Hz), 8.67–8.80 (3H, m)

EXAMPLE 42

Preparation of 10-{2'-[2''-(O-ethyl-L-β-aspartyloxy) ethyloxy]ethyloxy}-7-ethyl-(20S)-camptothecin (the camptothecin derivative of the following formula) hydrochloride

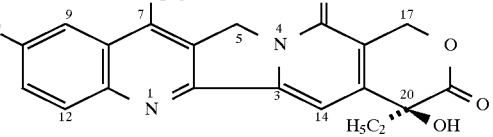

(1) Preparation of 1-{5'-[2''-(2'''-(N-t-butoxycarbonyl-O-ethyl-L-β-aspartyloxy)ethyloxy)ethyloxy]-2'-nitrophenyl}-2-propen-1-one 1-{5'-[2''-(2'''-(N-t-Butoxycarbonyl-O-ethyl-L-β-aspartyloxy)ethyloxy)-ethyloxy]-2'-nitrophenyl}-2-propen-1-one is obtained in the same manner as in Example 34-(1) and (2).

IR (Neat): $v_{max}^{cm-1}$=3370, 1740, 1720, 1680

Mass: m/z=525 (M+H⁺)

NMR (300 MHz, CDCl₃): $\delta^{TMS}$=1.26 (3H, t, J=7 Hz), 1.44 (9H, s), 2.85 (1H, dd, J=7 Hz, 5 Hz), 3.01 (1H, dd, J=7 Hz, 5 Hz), 3.75 (2H; m), 3.86–3.90 (2H, m), 4.22–4.31 (4H, m), 4.20 (2H, q, J=7 Hz), 4.50–4.62 (1H, m), 5.51 (1H, brd, J=8 Hz), 5.84 (1H, d, J=17.5 Hz), 6.01 (1H, d, J=10.5 Hz), 6.62 (1H, dd, J=17.5 Hz, 10.5 Hz), 6.86 (1H, d, J=3 Hz), 7.08 (1H, dd, J=9 Hz, 3 Hz), 8.17 (1H, d, J=9 Hz)

(2) Preparation of 10-[2'-(2''-(N-t-butoxycarbonyl-O-ethyl-L-β-aspartyloxy)ethyloxy)ethyloxy]-7-ethyl-(20S)-camptothecin 10-[2'-(2"-(N-t-Butoxycarbonyl-O-ethyl-L-β-aspartyloxy)ethyloxy)ethyloxy]- 7-ethyl-(20S)-camptothecin is obtained in the same manner as in Example 34-(3).

M.p.: >164° C. (decomposed)

IR (Nujol): $v_{max}^{cm-1}$=3365, 1750, 1655

Mass: m/z=724 (M+H$^+$)

NMR (300 MHz, d$_6$-DMSO): $\delta^{TMS}$=0.88 (3H, t, J=7.5Hz), 1.15 (3H, t, J=7 Hz), 1.31 (3H, t, J=7.5 Hz), 1.37 (9H, s), 1.79–1.94 (2H, m), 2.66 (1H, dd, J=16 Hz, 6 Hz), 2.78 (1H, dd, J=16 Hz, 6 Hz), 3.18 (2H, q, J=7.5 Hz), 3.73 (2H, t, J=5 Hz), 3.87 (2H, m), 4.07 (2H, q, J=7.0 Hz), 4.20 (2H, m), 4.30–4.39 (3H, m), 5.28 (2H, s), 5.42 (2H, s), 6.48 (1H, s), 7.26 (1H, d, J=6 Hz), 7.27 (1H, s), 7.49–7.54 (2H, m), 8.07 (1H, d, J=10 Hz)

(3) Preparation of 10-{2'-[2"-(O-ethyl-L-β-aspartyloxy)ethyloxy]ethyloxy)-7-ethyl-(20S)-camptothecin hydrochloride 10-{2'-[2"-(O-Ethyl-L-β-aspartyloxy)ethyloxy]ethyloxy}-7-ethyl-(20S)-camptothecin hydrochloride is obtained in the same manner as in Example 34-(4).

M.p.: >170° C. (decomposed)

IR (Nujol): $v_{max}^{cm-1}$=3375, 1750, 1660

Mass: m/z=624 [(M–Cl$^-$)$^+$]

NMR (300 MHz, d$_6$-DMSO): $\delta^{TMS}$=0.88 (3H, t, J=7.5 Hz), 1.19 (3H, t, J=7 Hz), 1.32 (3H, t, J=7.5 Hz), 1.79–1.94 (2H, m), 2.99 (1H, dd, J=17.5 Hz, 6 Hz), 3.08 (1H, dd, J=17.5 Hz, 6 Hz), 3.19 (2H, q, J=7.5 Hz), 3.75 (2H, m), 3.88 (2H, m), 4.19 (2H, q, J=7 Hz), 4.28–4.35 (5H, m), 5.29 (2H, s), 5.43 (2H, s), 7.29 (1H, s), 7.50–7.55 (2H, m), 8.08 (1H, d, J=10 Hz), 8.66–8.82 (3H, m)

EXAMPLE 43

Preparation of 7-ethyl-10-[3'-(glycyl-glycyl-glycyl-glycylamino)propyloxy]-(20S)-camptothecin hydrochloride (SEQ ID No: 1)

(1) Preparation of 7-ethyl-10-[3'-(t-butoxycarbonyl-glycyl-glycyl-glycyl-glycylamino)propyloxy]-(20S)-camptothecin (SEQ ID No: 1) 7-Ethyl-10-[3'-(t-butoxycarbonyl-glycyl-glycyl-glycyl-glycylamino)propyloxy]-(20S)-camptothecin (SEQ ID No: 1) (269 mg) is obtained in the same manner as in Example 8-(1) from 7-ethyl-10-(3'-aminopropyloxy)-(20S)-camptothecin hydrochloride (200 mg) and t-butoxycarbonyl-glycyl-glycyl-glycyl-glycine (SEQ ID No: 1) (2 equivalents) as a yellow powder.

Yield: 84%

IR (Nujol): $v_{max}^{cm-1}$3290, 1750, 1710, 1650, 1625

Mass: m/z=778 (M+H$^+$)

NMR (300 MHz, CDCl$_3$+d$_6$-DMSO): $\delta^{TMS}$=1.01 (3H, t, J=7 Hz), 1.40 (3H, t, J=7.5 Hz), 1.43 (9H, s), 1.93 (2H, dq, J=7.5 Hz, 3 Hz), 2.01–2.16 (2H, m), 3.18 (2H, t, J=7.5 Hz), 3.47 (2H, m), 3.74 (2H, d, J=5.5 Hz), 3.83–3.89 (6H, m), 4.22 (2H, t, J=6 Hz), 5.24 (2H, s), 5.29 (1H, d, J=16 Hz), 5.64 (1H, d, J=16 Hz), 5.88 (1H, s), 6.55 (1H, m), 7.38 (1H, d, J=3 Hz), 7.47 (1H, dd, J=9 Hz, 3 Hz), 7.56 (1H, s), 7.85 (1H, t), 8.07 (1H, d, J=9 Hz), 8.07–8.17 (3H, m)

(2) Preparation of 7-ethyl-10-[3'-(glycyl-glycyl-glycyl-glycylamino)propyloxy]-(20S)-camptothecin hydrochloride (SEQ ID No. 1)

7-Ethyl-10-[3'-(glycyl-glycyl-glycyl-glycylamino)propyloxy]-(20S)-camptothecin hydrochloride (SEQ ID No: 1) (237 mg) is obtained in the same manner as in Example 8-(2) from 7-ethyl-10-[3'-(t-butoxycarbonyl-glycyl-glycyl-glycyl-glycylamino)propyloxy]-(20S)-camptothecin (SEQ ID No: 1) (261 mg) as a yellow powder.

Yield: 99%

M.p.: >190° C. (decomposed)

IR (Nujol): $v_{max}^{cm-}$=3195, 1750, 1655, 1615

Mass: m/z=678 [(M–Cl$^-$)$^+$]

NMR (300 MHz, d$_6$-DMSO): $\delta^{TMS}$=0.88 (3H, t, J=7.5 Hz), 1.32 (3H, t, J=7.5 Hz), 1.80–2.02 (4H, m), 3.20 (2H, q, J=8Hz), 3.31 (2H, q, J=7 Hz), 3.61 (2H, q, J=6 Hz), 3.70 (2H, q, J=6 Hz), 3.76 (2H, q, J=6 Hz), 3.84 (2H, q, J=6 Hz), 4.24 (2H, t, J=6 Hz), 5.31 (2H, s), 5.43 (2H, s), 7.29 (1H, s), 7.51–7.55 (2H, m), 8.01 (1H, t, J=5.5 Hz), 8.09 (1H, d, J=9.5 Hz), 8.14 (3H, br), 8.18 (1H, t, J=6 Hz), 8.40 (1H, t, J=6 Hz), 8.74 (1H, t, J=5.5 Hz)

EXAMPLE 44

Preparation of 7-ethyl-10-{2'-[2"-(glycyl-glycyl-L-phenylalanyl-glycyl-amino)ethyloxy]ethyloxy}-(20S)-camptothecin hydrochloride (SEQ ID No: 3)

(1) Preparation of 7-ethyl-10-{2'-[2"-(t-butoxycarbonyl-glycyl-glycyl-L-phenylalanyl-glycylamino)ethyloxy]ethyloxy}-(20S)-camptothecin (SEQ ID No: 3)
7-Ethyl-10-{2'-[2"-(t-butoxycarbonyl-glycyl-glycyl-L-phenylalanyl-glycylamino)ethyloxy]ethyloxy}-(20S)-camptothecin (SEQ ID No: 3) (550 mg) is obtained in the same manner as in Example 8-(1) from 7-ethyl-10-(2'-(2"-aminoethyloxy)-ethyloxy)-(20S)-camptothecin hydrochloride (400 mg) and t-butoxycarbonyl-glycyl-glycyl-L-phenylalanylglycine (SEQ ID No: 3) (2 equivalents) as a yellow powder.

Yield: 79%

M.p.: >160° C. (decomposed)

IR (Nujol): $v_{max}^{cm-1}$3300, 1750, 1655

Mass: m/z=898 (M+H$^+$)

NMR (300 MHz, d$_6$-DMSO): $\delta^{TMS}$=0.88 (3H, t, J=7Hz), 1.27 (3H, t, J=7 Hz), 1.36 (9H, s), 1.83–1.89 (2H, m), 2.78 (1H, dd, J=14 Hz, 10 Hz), 3.04 (1H, dd, J=14 Hz, 4.5 Hz), 3.18 (2H, q, J=7.5 Hz), 3.11–3.80 (8H, m), 3.29 (2H, q, J=6 Hz), 3.84–3.87 (2H, m), 4.34–4.36 (2H, m), 4.45–4.53 (1H, m), 5.30 (2H, s), 5.43 (2H, s), 6.51 (1H, s), 7.00 (1H, t, J=5.5 Hz), 7.14–7.25 (5H, m), 7.27 (1H, s), 7.52–7.55 (2H, m), 7.83 (1H, t, J=5.5 Hz), 7.93 (1H, t, J=5Hz), 8.08 (1H, d, J=9.5 Hz), 8.17 (1H, d, J=8 Hz), 8.29 (1H, t, J=5.5 Hz)

(2) Preparation of 7-ethyl-10-(2'-[2"-(glycyl-glycyl-L-phenylalanyl-glycyl-amino)ethyloxy]ethyloxy}-(20S)-camptothecin hydrochloride (SEQ ID No: 3)
7-Ethyl-10-{2'-[2"-(glycyl-glycyl-L-phenylalanyl-glycylamino)ethyloxy]-ethyloxy}-(20S)-camptothecin hydrochloride (SEQ ID No: 3) (334 mg) is obtained in the same manner as in Example 8-(2) as a yellow powder from 7-ethyl-10-{2'-[2"-(t-butoxycarbonyl-glycyl-glycyl-L-phenylalanyl-glycylamino)ethyloxy]ethyloxy}-(20S)-camptothecin (SEQ ID No: 3) (550 mg).

Yield: 65%

M.p.: >165° C. (decomposed)

IR (Nujol): $v_{max}^{cm-1}$=3225, 1750, 1655

Mass: m/z=798 [(M–Cl$^-$)$^+$]

NMR (300 MHz, d$_6$-DMSO): $\delta^{TMS}$=0.88 (3H, t, J=7.5 Hz), 1.26–1.34 (3H, m), 1.80–1.94 (2H, m), 2.82 (1H, dd, J=14 Hz, 10 Hz), 3.06 (1H, dd, J=14 Hz, 5.5 Hz), 3.20 (2H, q, J=7.5 Hz), 3.29 (2H, q, J=6 Hz), 3.55 (2H, t, J=6 Hz), 3.62–3.80 (6H, m), 3.82–3.89 (2H, m), 4.33–4.37 (2H, m), 4.51–4.58 (1H, m), 5.30 (2H, s), 5.43 (2H, s), 7.14–7.25 (5H, m), 7.30 (1H, s), 7.53–7.56 (2H, m), 7.94 (1H, t, J=5.5 Hz), 8.09 (1H, d, J=9.5 Hz), 8.14 (3H, br), 8.32 (1H, t, J=6 Hz), 8.38 (1H, d, J=8.5 Hz), 8.60 (1H, t, J=5.5 Hz)

EXAMPLE 45

Preparation of the camptothecin derivative of the following formula (SEQ ID No: 3):

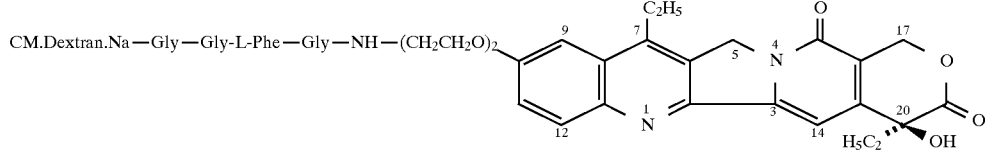

CM-Dextran sodium salt (CM-degree; 0.5) (2.3 g) and 7-ethyl-10-{2'-[2"-(glycyl-glycyl-L-phenylalanylglycylamino)ethyloxy]ethyloxy}-(20S)-camptothecin hydrochloride (SEQ ID No: 3) (310 mg) which is obtained in Example 44 are treated in the same manner as in Example 22 to give the desired camptothecin derivative (1.83 g) as a pale yellow powdery complex. The content of 7-ethyl-10-(2'-aminoethyloxy-ethyloxy)-(20S)-camptothecin hydrochloride in the desired camptothecin derivative is 1.6% which is calculated on the basis of the absorbance at 380 nm. According to the GPC analysis, the average molecular weight of the desired camptothecin derivative is 200,000, and the degree of distribution (Mw/Mn) is 1.38.

EXAMPLE 46

Preparation of 7-ethyl-10-[3'-(glycyl-glycyl-L-phenylalanyl-glycyloxy)-propyloxy]-(20S)-camptothecin hydrochloride (SEQ ID No: 3)

(1) Preparation of 7-ethyl-10-[3'-(t-butoxycarbonyl-glycyl-glycyl-L-phenylalanyl-glycyloxy)propyloxy]-(20S)-camptothecin (SEQ ID No: 3)

7-Ethyl-10-(3'-hydroxypropyloxy)-(20S)-camptothecin (50 mg), t-butoxycarbonyl-glycyl-glycyl-L-phenylalanyl-glycine (SEQ ID No: 3) (2 equivalents) and a catalytic amount of 4-dimethylaminopyridine are mixed in dry dimethylformamide (2.5 ml), and thereto is added N,N'-dicyclohexylcarbodiimide (3 equivalents). The mixture is reacted at room temperature overnight, and treated in the same manner as in Example 8-(1) to give 7-ethyl-10-[3'-(t-butoxycarbonyl-glycyl-glycyl-L-phenylalanyl-glycyloxy)propyloxy]-(20S)-camptothecin (SEQ ID No: 3) (71 mg) as a yellow powder.

Yield: 74%

IR (Nujol): $\nu_{max}^{cm-1}$=3300, 1750, 1660

Mass: m/z=869 (M+H$^+$)

NMR (300 MHz, d$_6$-DMSO): $\delta^{TMS}$=0.88 (3H, t, J=7.5 Hz), 1.31 (3H, t, J=7.5 Hz), 1.37 (9H, s), 1.80–1.94 (2H, m), 2.11–2.20 (2H, m), 2.72 (1H, dd, J=14 Hz, 10 Hz), 3.02 (1H, dd, J=14 Hz, 5 Hz), 3.18 (2H, q, J=7 Hz), 3.52–3.79 (4H, m), 3.88 (2H, dd, J=6 Hz, 2 Hz), 4.30 (4H, t, J=6 Hz), 4.50 (1H, m), 5.29 (2H, s), 5.43 (2H, s), 6.50 (1H, s), 6.98 (1H, t, J=6 Hz), 7.12–7.25 (5H, m), 7.27 (1H, s), 7.51–7.55 (2H, m), 7.88 (1H, t, J=5 Hz), 8.08 (1H, d, J=9.5 Hz), 8.32 (1H, t, J=5 Hz)

(2) Preparation of 7-ethyl-10-[3'-(glycyl-glycyl-L-phenylalanyl-glycyloxy)-propyloxy]-(20S)-camptothecin hydrochloride (SEQ ID No: 3)

7-Ethyl-10-[3'-(glycyl-glycyl-L-phenylalanyl-glycyloxy)propyloxy]-(20S)-camptothecin hydrochloride (SEQ ID No: 3) (39 mg) is obtained in the same manner as in Example 8-(2) from 7-ethyl-10-[3'-(t-butoxycarbonyl-glycyl-glycyl-L-phenylalanyl-glycyloxy)propyloxy]-(20S)-camptothecin (SEQ ID No: 3) (SEQ ID No: 3) (58 mg) as a yellow powder.

Yield: 72%

M.p.: >167° C. (decomposed)

IR (Nujol): $\nu_{max}^{cm-1}$=3285, 1745, 1655

Mass: m/z=769 [(M–Cl$^-$)$^+$]

NMR (300 MHz, d$_6$-DMSO): $\delta^{TMS}$=0.88 (3H, t, J=7 Hz), 1.31 (3H, t, J=7.5 Hz), 1.80–1.93 (2H, m), 2.12–2.20 (2H, m), 2.72 (1H, dd, J=14 Hz, 10 Hz), 3.02 (1H, dd, J=14 Hz, 4.5 Hz), 3.18 (2H, q, J=7.5 Hz), 3.54–3.92 (6H, m), 4.31 (4H, t, J=6 Hz), 4.51–4.59 (1H, m), 5.29 (2H, s), 5.43 (2H, s), 7.13–7.22 (5H, m), 7.27 (1H, s), 7.51–7.56 (2H, m), 8.03 (3H, br), 8.09 (1H, d, J=9.5Hz), 8.35 (1H, d, J=9 Hz), 8.51 (1H, t, J=5.5 Hz), 8.60 (1H, t, J=6 Hz)

EXAMPLE 47

Preparation of the camptothecin derivative of the following formula (SEQ ID No: 3):

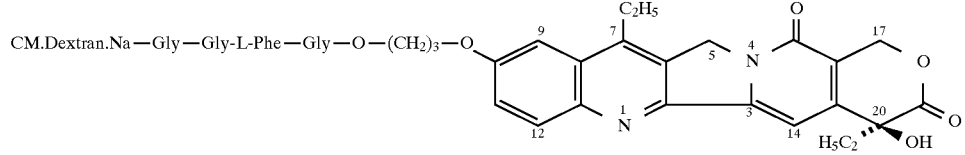

CM-Dextran sodium salt (CM-degree; 0.5) (250 mg) and 7-ethyl-10-[3'-(glycyl-glycyl-L-phenylalanyl-glycyloxy)propyloxy]-(20S)-camptothecin hydrochloride (SEQ ID No: 3) (33 mg) which is obtained in Example 46 are treated in the same manner as in Example 22 to give the desired camptothecin derivative (196 mg) as a pale yellow powdery complex. The content of 7-ethyl-10-(3'-hydroxypropyloxy)

-(20S)-camptothecin in the desired camptothecin derivative is 3.6% which is calculated on the basis of the absorbance at 380 nm. According to the GPC analysis, the average molecular weight of the desired camptothecin derivative is 182,000, and the degree of distribution (Mw/Mn) is 1.48.

EXAMPLE 48

Preparation of 10-(4'-aminobutyloxy)-7-ethyl-(20S)-camptothecin hydrochloride 10-(4'-Aminobutyloxy)-7-ethyl-(20S)-camptothecin hydrochloride is obtained in the same manner as in Example 1 as a yellow powder.

M.p.: >200° C. (decomposed)
IR (Nujol): $v_{max}^{cm-1}$=3410, 1745, 1655, 1615
Mass: m/z=464 [(M–Cl$^-$)$^+$]
NMR (300 MHz, d$_6$-DMSO): $\delta^{TMS}$=0.88 (3H, t, J=7.5 Hz), 1.32 (3H, t, J=7.5 Hz), 1.77–1.93 (6H, m), 2.90 (2H, t, J=7 Hz), 3.20 (2H, q, J=7.5 Hz), 4.24 (2H, t, J=6 Hz), 5.31 (2H, s), 5.43 (2H, s), 7.28 (1H, s), 7.50–7.53 (2H, m), 8.00 (3H, br), 8.09 (1H, d, J=10 Hz)

EXAMPLE 49

Preparation of 10-[4'-(glycyl-glycyl-L-phenylalanyl-glycylamino)butyloxy]-7-ethyl-(20S)-camptothecin hydrochloride (SEQ ID No: 3)

10-[4'-(Glycyl-glycyl-L-phenylalanyl-glycylamino) butyloxy]-7-ethyl-(20S)-camptothecin hydrochloride (SEQ ID No: 3) is obtained in the same manner as in Example 11-(1) and Example 80(2) as a yellow powder.

M.p.: >156° C. (decomposed)
IR (Nujol): $v_{max}^{cm-1}$=3270, 1745, 1655, 1615
Mass: m/z=782 [(M–Cl$^-$)$^+$]
NMR (300 MHz, d$_6$-DMSO): $\delta^{TMS}$=0.88 (3H, t, J=7.5 Hz), 1.31 (3H, t, J=7.5 Hz), 1.60–1.94 (6H, m), 2.79–2.87 (1H, m), 3.07 (1H, dd, J=14 Hz, 5 Hz), 3.15–3.23 (4H, m), 3.73–3.90 (6H, m), 4.22 (2H, t, J=6 Hz), 4.50–4.58 (1H, m), 5.30 (2H, s), 5.43 (2H, s), 7.17–7.27 (5H, m), 7.28 (1H, s), 7.50–7.53 (2H, m), 7.87 (1H, t, J=6 Hz), 8.07–8.12 (4H, br), 8.39 (1H, t, J=6 Hz), 8.40 (1H, d, J=8 Hz), 8.60 (1H, t, J=6 Hz)

EXAMPLE 50

Preparation of 10-{3'-[N-(glycyl-L-phenylalanyl-glycyl-glycyl)-N-methyl-amino]propyloxy}-7-ethyl-(20S)-camptothecin hydrochloride (SEQ ID No: 3)

10-{3'-[N-(Glycyl-L-phenylalanyl-glycyl-glycyl)-N-methylamino]-propyloxy}- 7-ethyl-(20S)-camptothecin hydrochloride is obtained in the same manner as in Example 8.

EXAMPLE 51

Preparation of the camptothecin derivative of the following formula:

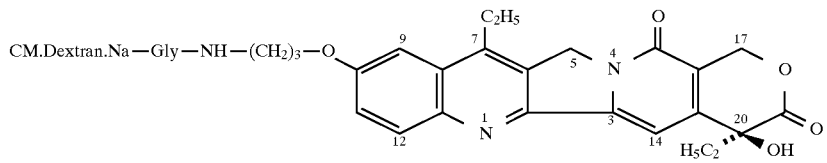

CM-Dextran sodium salt (CM-degree; 0.45) (1116 mg) and 7-ethyl-10-[3'-(glycylamino)propyloxy]-(20S)-camptothecin hydrochloride (95 mg) which is obtained in Example 9 are treated in the same manner as in Example 23 to give the desired camptothecin derivative (1117 mg) as a pale yellow powder. The content of 10-(3'-aminopropyloxy)-7-ethyl-(20S)-camptothecin hydrochloride (the compound of Example 1-(8-1)) in the desired camptothecin derivative is 4.8% which is calculated on the basis of the absorbance at 380 nm. According to the GPC analysis, the average molecular weight of the desired camptothecin derivative is 143,000, and the degree of distribution (Mw/Mn) is 1.53.

EXAMPLE 52

Preparation of the camptothecin derivative of the following formula (SEQ ID No: 3):

CM.Dextran.Na—Gly—Gly-L-Phe—Gly—NH—(CH$_2$)$_5$—O...

CM-Dextran sodium salt (CM-degree; 0.64) (1400 mg) and 10-[5'-(glycyl-glycyl-L-phenylalanyl-glycylamino) pentyloxy]-7-ethyl-(20S)-camptothecin hydrochloride (SEQ ID No: 3) (182 mg) which is obtained in Example 17 are treated in the same manner as in Example 23 to give the desired camptothecin derivative (1330 mg) as a pale yellow powder. The content of 10-(5'-aminopentyloxy)-7-ethyl-(20S)-camptothecin hydrochloride (the compound of Example 3) in the desired camptothecin derivative is 3.4% which is calculated on the basis of the absorbance at 377 nm. According to the GPC analysis, the average molecular weight of the desired camptothecin derivative is 193,000, and the degree of distribution (Mw/Mn) is 1.56.

EXAMPLE 53

Preparation of the camptothecin derivative of the following formula (SEQ ID No: 3):

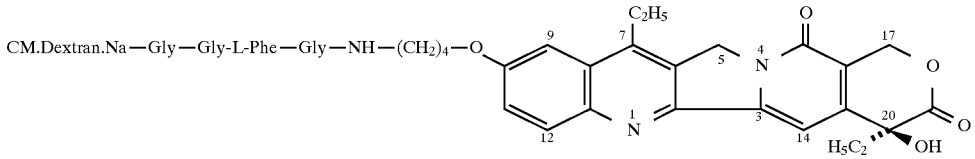

CM-Dextran sodium salt (CM-degree; 0.64) (1400 mg) and 10-[4'-(glycyl-glycyl-L-phenylalanyl-glycylamino) butyloxy]-7-ethyl-(20S)-camptothecin hydrochloride (SEQ ID No: 3) (182 mg) which is obtained in Example 49 are treated in the same manner as in Example 23 to give the desired camptothecin derivative (1390 mg) as a pale yellow powder. The content of 10-(4'-aminobutyloxy)-7-ethyl-(20S)-camptothecin hydrochloride (the compound of Example 48) in the desired camptothecin derivative is 3.8% which is calculated on the basis of the absorbance at 377 nm. According to the GPC analysis, the average molecular weight of the desired camptothecin derivative is 181,000, and the degree of distribution (Mw/Mn) is 1.76.

EXAMPLES 54–69

The camptothecin derivatives as listed on Table 1 are obtained from the corresponding starting compounds as listed in Table 1 in the same manner as in Example 23 or 23.

IR (Nujol): $v_{max}^{cm-1}$=3300, 1750, 1660, 1615

Mass: m/z=564 [(M–Cl$^-$)$^+$]

NMR (300 MHz, d$_6$-DMSO): $\delta^{TMS}$=0.88 (3H, t, J=7.5 Hz), 1.32 (3H, t, J=7.5 Hz), 1.80–1.93 (2H, m), 1.93–2.03 (2H, m), 3.15–3.26 (2H, m), 3.27–3.36 (2H, m), 3.57–3.64 (2H, m), 3.79 (2H, d, J=5.5 Hz), 4.25 (2H, brt), 5.31 (2H, s), 5.43 (2H, s), 7.28 (1H, s), 7.49–7.55 (2H, m), 8.09 (1H, d, J=9 Hz), 8.05–8.25 (3H, br), 8.21 (1H, brt), 8.71 (1H, brd)

EXAMPLE 71

Preparation of 7-ethyl-10-[3'-(D-phenylalanyl-glycylamino)propyloxy]-(20S)-camptothecin hydrochloride 7-Ethyl-10-[3'-(D-phenylaianyl-glycylamino)propyloxy]-(20S)-camptothecin hydrochloride is obtained in the same manner as in Example 11 as a yellow powder.

M.p.: >180° C. (decomposed)

IR (Nujol): $v_{max}^{cm-1}$=3250, 1745, 1655, 1610

TABLE 1

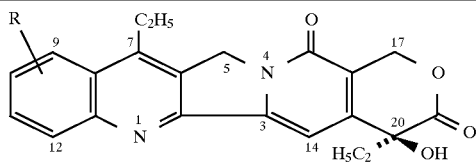

| Ex. No. | Ex. No. of starting compound | R |
|---|---|---|
| 54 | 8  | 10-CM.Dextran.Na-L-Tyr—NH—(CH$_2$)$_3$—O— |
| 55 | 10 | 10-CM.Dextran.Na-L-Ser—NH—(CH$_2$)$_3$—O— |
| 56 | 12 | 10-CM.Dextran.Na-L-Phe—Gly—NH—(CH$_2$)$_2$—O— |
| 57 | 13 | 9-CM.Dextran.Na-L-Phe—Gly—NH—(CH$_2$)$_3$—O— |
| 58 | 14 | 11-CM.Dextran.Na-L-Phe—Gly—NH—(CH$_2$)$_3$—O— |
| 59 | 15 | 10-CM.Dextran.Na-L-Tyr—Gly—NH—(CH$_2$)$_3$—O— |
| 60 | 34 | 10-CM.Dextran.Na-L-Ala—O—(CH$_2$)$_3$—O— |
| 61 | 35 | 10-CM.Dextran.Na-L-Ala—O—(CH$_2$)$_2$—O— |
| 62 | 36 | 10-CM.Dextran.Na-L-Ala—O—(CH$_2$)$_2$—O—(CH$_2$)$_2$—O— |
| 63 | 37 | 10-CM.Dextran.Na-L-Pro—O—(CH$_2$)$_3$—O— |
| 64 | 38 | 10-CM.Dextran.Na-L-Pro—O—(CH$_2$)$_2$—O— |
| 65 | 39 | 10-CM.Dextran.Na-L-Pro—O—(CH$_2$)$_3$—O—(CH$_2$)$_2$—O— |
| 66 | 40 | 10-CM.Dextran.Na-L-β-Asp(O(C$_2$H$_5$)—O—(CH$_2$)$_3$—O— |
| 67 | 41 | 10-CM.Dextran.Na-L-β-Asp(O(C$_2$H$_5$)—O—(CH$_2$)$_2$—O— |
| 68 | 42 | 10-CM.Dextran.Na-L-β-Asp(O(C$_2$H$_5$)—O—(CH$_2$)$_2$—O—(CH$_2$)$_2$—O— |
| 69 | 50 | 10-CM.Dextran.Na—Gly-L-Phe—Gly—Gly—N(CH$_3$)—(CH$_2$)$_3$—O— (SEQ ID NO:3) |

EXAMPLE 70

Preparation of 7-ethyl-10-[3'-(glycyl-glycylamino) propyloxy]-(20S)-camptothecin hydrochloride 7-Ethyl-10-[3'-(glycyl-glycylamino)propyloxy]-(20S)-camptothecin hydrochloride is obtained in the same manner as in Example 11 as a yellow powder.

M.p.: >181° C. (decomposed)

Mass: m/z=654 [(M–Cl$^-$)$^+$]

NMR (300 MHz, d$_6$-DMSO): $\delta^{TMS}$=0.88 (3H, t, J=7.5 Hz), 1.32 (3H, t, J=7.5 Hz), 1.80–1.91 (2H, m), 1.91–2.02 (2H, m), 2.97 (1H, dd, J=14 Hz, 7.5 Hz), 3.10 (1H, dd, J=14 Hz, 6 Hz), 3.15–3.29 (2H, m), 3.28–3.36 (2H, m), 3.69 (1H, dd, J=16 Hz, 6 Hz), 3.80 (1H, dd, J=16 Hz, 6 Hz), 4.09 (1H, m), 4.25 (2H, t, J=7 Hz), 5.30 (2H, s), 5.43 (2H, s), 7.22–7.35 (6H, m), 7.47–7.55 (2H, m), 8.08 (1H, d, J=9.5 Hz), 8.19 (1H, brt), 8.25–8.42 (3H, br)

EXAMPLE 72

Preparation of 7-ethyl-10-[3'-(glycyl-glycyl-glycylamino)propyloxy]-(20S)-camptothecin hydrochloride 7-Ethyl-10-[3'-(glycyl-glycyl-glycylamino)propyloxy]-(20S)-camptothecin hydrochloride is obtained in the same manner as in Example 11 as a yellow powder.

M.p.: >158° C. (decomposed)

IR (Nujol): $v_{max}^{cm-1}$=3250, 1750, 1655, 1615

Mass: m/z=621 [(M–Cl⁻)⁺]

NMR (300 MHz, d$_6$-DMSO): $\delta^{TMS}$=0.88 (3H, t, J=7 Hz), 1.32 (3H, t, J=7 Hz), 1.80–2.20 (4H, m), 3.20 (2H, q, J=7 Hz), 3.31 (2H, q, J=7 Hz), 3.61 (2H, q, J=6 Hz), 3.71 (2H, d, J=5.5 Hz), 3.84 (2H, d, J=6 Hz), 4.24 (2H, t, J=6 Hz), 5.30 (2H, s), 5.43 (2H, s), 6.56 (1H, s), 7.29 (1H, s), 7.51 (1H, s), 7.52 (1H, d, J=9 Hz), 8.06 (1H, t, J=6 Hz), 8.19 (1H, d, J=9 Hz), 8.19 (3H, br), 8.36 (1H, t, J=6 Hz), 8.80 (1H, t, J=5.5 Hz)

EXAMPLE 73

Preparation of 7-ethyl-10-[3'-(glycyl-glycyl-glycyl-glycyl-glycylamino)-propyloxy]-(20S)-camptothecin hydrochloride (SEQ ID No: 2)

7-Ethyl-10-[3'-(glycyl-glycyl-glycyl-glycyl-glycylamino)propyloxy]-(20S)-camptothecin hydrochloride (SEQ ID No: 2) is obtained in the same manner as in Example 11-(1) and Example 8-(2) as a yellow powder.

M.p.: >186° C. (decomposed)

IR (Nujol): $v_{max}^{cm-1}$=3220, 1745, 1655, 1615

Mass: m/z=735 [(M–Cl⁻)⁺]

NMR (300 MHz, d$_6$-DMSO): $\delta^{TMS}$=0.88 (3H, t, J=7.5 Hz), 1.32 (3H, t, J=7.5 Hz), 1.83–1.91 (2H, m), 1.94–2.02 (2H, m), 3.16–3.34 (2H, mt), 3.30 (2H, q, J=6 Hz), 3.69 (2H, d, J=5.5 Hz), 3.74–3.78 (4H, m), 3.85 (2H, d, J=5.5 Hz), 4.24 (2H, t, J=6 Hz), 5.31 (2H, s), 5.43 (2H, s), 7.30 (1H, s), 7.51–7.55 (2H, m), 8.00 (1H, t, J=6 Hz), 8.10 (1H, d, J=9.5 Hz), 8.18 (3H, br), 8.23 (1H, t, J=6 Hz), 8.28 (1H, t, J=5.5 Hz ), 8.43 (1H, t, J=5.5 Hz), 8.82 (1H, t, J=5.5 Hz)

EXAMPLE 74

Preparation of 7-ethyl-10-[3'-(glycyl-glycyl-D-phenylalanyl-glycylamino)-propyloxy]-(20S)-camptothecin hydrochloride (SEQ ID No: 3)

7-Ethyl-10-[3'-(glycyl-glycyl-D-phenylalanyl-glycylamino)propyloxy]-(20S)-camptothecin hydrochloride (SEQ ID No: 3) is obtained in the same manner as in Example 11-(1) and Example 8-(2) as a yellow powder.

M.p.: >136° C. (decomposed)

IR (Nujol): $v_{max}^{cm-1}$=3220, 1745, 1655

Mass: m/z=768 [(M–Cl⁻)⁺]

NMR (300 MHz, d$_6$-DMSO): $\delta^{TMS}$=0.88 (3H, t, J=7.5 Hz), 1.31 (3H, t, J=7.5 Hz), 1.80–1.93 (2H, m), 1.92–2.04 (2H, m), 2.80 (1H, dd, J=14 Hz, 10 Hz), 3.04 (1H, dd, J=14 Hz, 4.5 Hz), 3.14–3.24 (2H, m), 3.28–3.35 (2H, m), 3.54–4.20 (6H, m), 4.25 (2H, brt), 4.48–4.58 (1H, m), 5.29 (2H, s), 5.43 (2H, s), 7.13–7.27 (5H, m), 7.28 (1H, s), 7.51 (1H, m), 7.50–7.56 (1H, m), 7.95 (1H, brt), 8.09 (1H, d, J=9 Hz), 8.04–8.17 (3H, br), 8.35 (1H, brt), 8.39 (1H, brd), 8.59 (1H, brt)

EXAMPLES 75–78

The compounds as listed in Table 2 are obtained from the compound obtained in Example 1 in the same manner as in Example 8 or 11.

TABLE 2

| Ex. No. | R |
|---|---|
| 75 | HCl.10-L-Leu—Gly—NH—(CH$_2$)$_3$—O— |
| 76 | HCl.10-L-Tyr—Gly—NH—(CH$_2$)$_3$—O— |
| 77 | HCl.10-L-Val—Gly—NH—(CH$_2$)$_3$—O— |
| 78 | HCl.10-Gly-L-Phe—NH—(CH$_2$)$_3$—O— |

EXAMPLES 79–80

The compounds as listed in Table 3 are obtained from the compound obtained in Example 4 or 5 in the same manner as in Example 8 or 11.

TABLE 3

| Ex. No. | R | |
|---|---|---|
| 79 | HCl.9-GLy—Gly-L-Phe—Gly—NH—(CH$_2$)$_3$—O— | (SEQ ID NO:3) |
| 80 | HCl.11-GLy—Gly-L-Phe—Gly—NH—(CH$_2$)$_3$—O— | (SEQ ID NO:3) |

EXAMPLE 81

Preparation of the camptothecin derivative of the following formula:

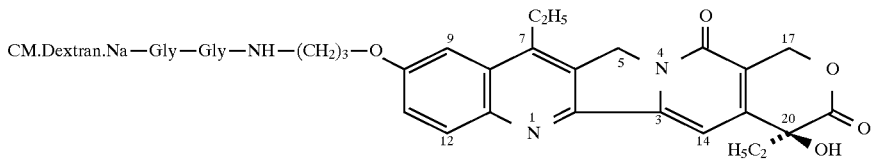

CM-Dextran sodium salt (CM-degree; 0.65) (2220 mg) and 7-ethyl-10-[3'-(glycyl-glycylamino)propyloxy]-(20S)-camptothecin hydrochloride (222 mg) which is obtained in Example 70 are treated in the same manner as in Example 23 to give the desired camptothecin derivative (2310 mg) as a pale yellow powder. The content of 10-(3'-aminopropyloxy)-7-ethyl-(20S)-camptothecin hydrochloride (the compound of Example 1-(8-1)) in the desired camptothecin derivative is 5.2% which is calculated on the basis of the absorbance at 380 nm. According to the GPC analysis, the average molecular weight of the desired camptothecin derivative is 166,000, and the degree of distribution (Mw/Mn) is 1.55.

EXAMPLE 82

Preparation of the camptothecin derivative of the following formula:

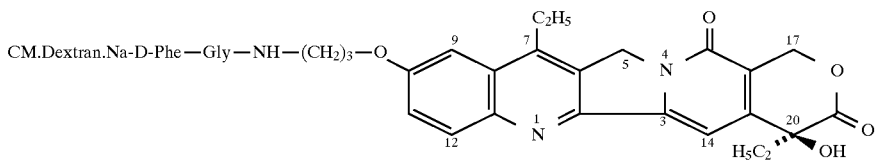

CM-Dextran sodium salt (CM-degree; 0.55) (2320 mg) and 7-ethyl-10-[$^{3'}$-(D-phenylalanyl-glycylamino)propyloxy]-(20S)-camptothecin hydrochloride (291 mg) which is obtained in Example 71 are treated in the same manner as in Example 23 to give the desired camptothecin derivative (1964 mg) as a pale yellow powder. The content of 10-(3'-aminopropyloxy)-7-ethyl-(20S)-camptothecin hydrochloride (the compound of Example 1-(8-1)) in the desired camptothecin derivative is 6.7% which is calculated on the basis of the absorbance at 380 nm. According to the GPC analysis, the average molecular weight of the desired camptothecin derivative is 184,000, and the degree of distribution (Mw/Mn) is 1.57.

EXAMPLE 83

Preparation of the camptothecin derivative of the following formula (SEQ ID No: 3):

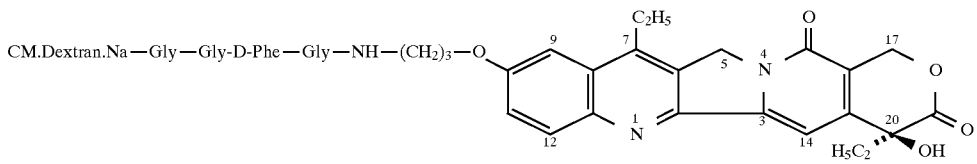

CM-Dextran sodium salt (CM-degree; 0.55) (2240 mg) and 7-ethyl-10-[3'-(glycyl-glycyl-D-phenylalanyl-glycylamino)propyloxy]-(20S)-camptothecin hydrochloride (SEQ ID No: 2) (291 mg) which is obtained in Example 74 are treated in the same manner as in Example 23 to give the desired camptothecin derivative (2005 mg) as a pale yellow powder. The content of 10-(3'-aminopropyloxy)-7-ethyl-(20S)-camptothecin hydrochloride (the compound of Example 1-(8-1)) in the desired camptothecin derivative is 5.5% which is calculated on the basis of the absorbance at 380 nm. According to the GPC analysis, the average molecular weight of the desired camptothecin derivative is 148,000, and the degree of distribution (Mw/Mn) is 1.84.

EXAMPLE 84

Preparation of the camptothecin derivative of the following formula:

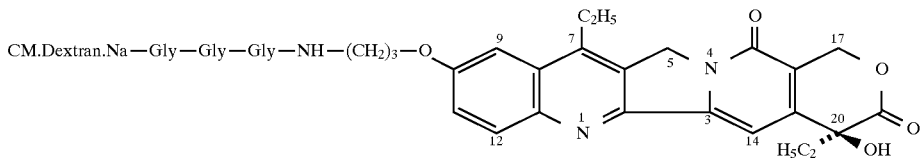

CM-Dextran sodium salt (CM-degree; 0.45) (2000 mg) and 7-ethyl-10-[3'-(glycyl-glycyl-glycylamino)propyloxy]-(20S)-camptothecin hydrochloride (260 mg) which is obtained in Example 72 are treated in the same manner as in Example 23 to give the desired camptothecin derivative (1901 mg) as a pale yellow powder. The content of 10-(3'-aminopropyloxy)-7-ethyl-(20S)-camptothecin hydrochloride (the compound of Example 1-(8-1)) in the desired camptothecin derivative is 5.3% which is calculated on the basis of the absorbance at 380 nm. According to the GPC analysis, the average molecular weight of the desired camptothecin derivative is 138,000, and the degree of distribution (Mw/Mn) is 1.51.

EXAMPLE 85

Preparation of the camptothecin derivative of the following formula (SEQ ID No: 2):

20S)-camptothecin hydrochloride (the compound of Example 1-(8-1)) in the desired camptothecin derivative is 4.7% which is calculated on the basis of the absorbance at 380 nm. According to the GPC analysis, the average molecular weight of the desired camptothecin derivative is 149,000, and the degree of distribution (Mw/Mn) is 1.50.

EXAMPLES 86–92

The compounds as listed in Table 4 are obtained in the same manner as in Example 22 or 23 from the corresponding starting compounds as listed in Table 4.

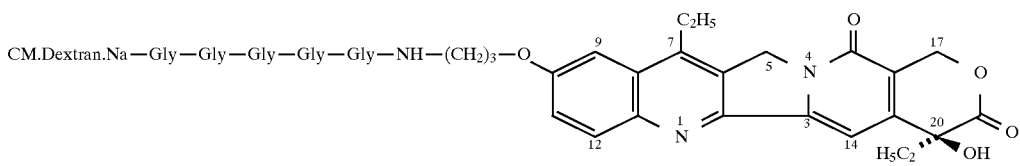

TABLE 4

| Ex. No. | Ex. No. of starting compounds | R | |
|---|---|---|---|
| 86 | 77 | 10-CM.Dextran.Na-L-Val—Gly—NH—(CH$_2$)$_3$—O— | |
| 87 | 75 | 10-CM.Dextran.Na-L-Leu—Gly—NH—(CH$_2$)$_3$—O— | |
| 88 | 76 | 10-CM.Dextran.Na-L-Tyr—Gly—NH—(CH$_2$)$_3$—O— | |
| 89 | 78 | 10-CM.Dextran.Na—Gly-L-Phe—NH—(CH$_2$)$_3$—O— | |
| 90 | 16 | 10-CM.Pullulan.Na—Gly—Gly-L-Phe—Gly—NH—(CH$_2$)$_3$—O— | (SEQ ID NO:3) |
| 91 | 79 | 9-CM.Dextran.Na—Gly—Gly-L-Phe—Gly—NH—(CH$_2$)$_3$—O— | (SEQ ID NO:3) |
| 92 | 80 | 11-CM.Dextran.Na—Gly—Gly-L-Phe—Gly—NH—(CH$_2$)$_3$—O— | (SEQ ID NO:3) |

[CM.Pullulan.Na: carboxymethylpullulan sodium salt]

CM-Dextran sodium salt (CM-degree; 0.45) (1640 mg) and 7-ethyl-10-[3'-(glycyl-glycyl-glycyl-glycyl-glycylamino)propyloxy]-(20S)-camptothecin hydrochloride (SEQ ID No: 2) (230 mg) which is obtained in Example 73 are treated in the same manner as in Example 23 to give the desired camptothecin derivative (1700 mg) as a pale yellow powder. The content of 10-(3'-aminopropyloxy)-7-ethyl-(

EXAMPLES 93–113

The compounds as listed in Table 5 are obtained in the same manner as in Example 11 from the corresponding starting compounds as listed in Table 5.

TABLE 5

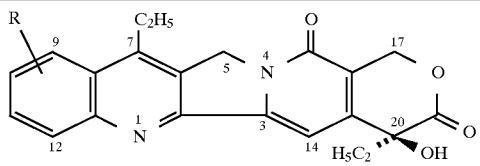

| Ex. No. | Ex. No. of starting compounds | R |
|---|---|---|
| 93 | 7 | HCl.10-Gly—Gly—N(CH₃)CH₂CH₂CH₂O— |
| 94 | 7 | HCl.10-Gly—Gly—Gly—N(CH₃)CH₂CH₂CH₂O— |
| 95 | 7 | HCl.10-Gly—Gly—Gly—Gly—N(CH₃)CH₂CH₂CH₂O—  (SEQ ID NO:1) |
| 96 | 2 | HCl.10-Gly—Gly—NHCH₂CH₂O— |
| 97 | 2 | HCl.10-Gly—Gly—Gly—NHCH₂CH₂O— |
| 98 | 2 | HCl.10-Gly—Gly—Gly—Gly—NHCH₂CH₂O—  (SEQ ID NO:1) |
| 99 | 3 | HCl.10-Gly—Gly—NHCH₂CH₂CH₂CH₂O— |
| 100 | 3 | HCl.10-Gly—Gly—Gly—NHCH₂CH₂CH₂CH₂O— |
| 101 | 3 | HCl.10-Gly—Gly—Gly—Gly—NHCH₂CH₂CH₂CH₂O—  (SEQ ID NO:1) |
| 102 | 4 | HCl.9-Gly—Gly—NHCH₂CH₂O— |
| 103 | 4 | HCl.9-Gly—Gly—Gly—NHCH₂CH₂O— |
| 104 | 4 | HCl.9-Gly—Gly—Gly—Gly—NHCH₂CH₂O—  (SEQ ID NO:1) |
| 105 | 5 | HCl.11-Gly—Gly—NHCH₂CH₂O— |
| 106 | 5 | HCl.11-Gly—Gly—Gly—NHCH₂CH₂CH₂O— |
| 107 | 5 | HCl.11-Gly—Gly—Gly—Gly—NHCH₂CH₂CH₂O—  (SEQ ID NO:1) |
| 108 | 6 | HCl.10-Gly—Gly—NHCH₂CH₂O—CH₂CH₂O— |
| 109 | 6 | HCl.10-Gly—Gly—Gly—NHCH₂CH₂O—CH₂CH₂O— |
| 110 | 6 | HCl.10-Gly—Gly—Gly—Gly—NHCH₂CH₂O—CH₂CH₂O—  (SEQ ID NO:1) |
| 111 | 48 | HCl.10-Gly—Gly—NHCH₂CH₂CH₂O— |
| 112 | 48 | HCl.10-Gly—Gly—Gly—NHCH₂CH₂CH₂O— |
| 113 | 48 | HCl.10-Gly—Gly—Gly—Gly—NHCH₂CH₂CH₂O—  (SEQ ID NO:1) |

EXAMPLES 114–158

The compounds as listed in Tables 6–8 are obtained in the same manner as in Example 22 or 23 from the corresponding starting compounds as listed in Table 6–8.

TABLE 6

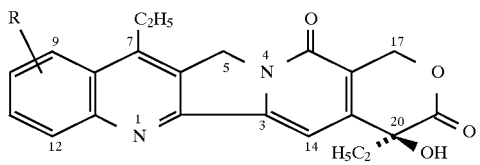

| Ex. No. | Ex. No. of starting compounds | R |
|---|---|---|
| 114 | 70 | 10-CM.Pullulan.Na—Gly—Gly—NHCH₂CH₂CH₂O— |
| 115 | 72 | 10-CM.Pullulan.Na—Gly—Gly—Gly—NHCH₂CH₂CH₂O— |
| 116 | 43 | 10-CM.Pullulan.Na—Gly—Gly—Gly—Gly—NHCH₂CH₂CH₂O—  (SEQ ID NO:1) |
| 117 | 93 | 10-CM.Dextran.Na—Gly—Gly—N(CH₃)CH₂CH₂CH₂O— |
| 118 | 93 | 10-CM.Pullulan.Na—Gly—Gly—N(CH₃)CH₂CH₂CH₂O— |
| 119 | 94 | 10-CM.Dextran.Na—Gly—Gly—Gly—N(CH₃)—CH₂CH₂CH₂O— |
| 120 | 94 | 10-CM.Pullulan.Na—Gly—Gly—Gly—N(CH₃)—CH₂CH₂CH₂O— |
| 121 | 95 | 10-CM.Dextran.Na—Gly—Gly—Gly—Gly—N(CH₃)—CH₂CH₂CH₂O—  (SEQ ID NO:1) |
| 122 | 95 | 10-CM.Pullulan.Na—Gly—Gly—Gly—Gly—N(CH₃)—CH₂CH₂CH₂O— |
| 123 | 96 | 10-CM.Dextran.Na—Gly—Gly—NHCH₂CH₂O— |
| 124 | 97 | 10-CM.Pullulan.Na—Gly—Gly—NHCH₂CH₂O— |
| 125 | 97 | 10-CM.Dextran.Na—Gly—Gly—Gly—NHCH₂CH₂O— |
| 126 | 97 | 10-CM.Pullulan.Na—Gly—Gly—Gly—NHCH₂CH₂O— |
| 127 | 98 | 10-CM.Dextran.Na—Gly—Gly—Gly—Gly—NHCH₂CH₂O—  (SEQ ID NO:1) |
| 128 | 98 | 10-CM.Pullulan.Na—Gly—Gly—Gly—Gly—NHCH₂CH₂O—  (SEQ ID NO:1) |

TABLE 7

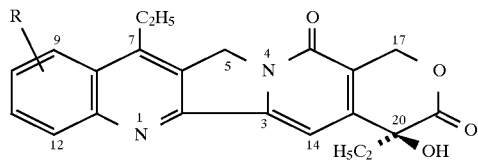

| Ex. No. | Ex. No. of starting compounds | R |
|---|---|---|
| 129 | 99 | 10-CM.Dextran.Na—Gly—Gly—NHCH$_2$CH$_2$—CH$_2$CH$_2$CH$_2$O— |
| 130 | 99 | 10-CM.Pullulan.Na—Gly—Gly—NHCH$_2$CH$_2$—CH$_2$CH$_2$CH$_2$O— |
| 131 | 100 | 10-CM.Dextran.Na—Gly—Gly—Gly—NHCH$_2$CH$_2$—CH$_2$CH$_2$CH$_2$O— |
| 132 | 100 | 10-CM.Pullulan.Na—Gly—Gly—Gly—NHCH$_2$CH$_2$—CH$_2$CH$_2$CH$_2$O— |
| 133 | 101 | 10-CM.Dextran.Na—Gly—Gly—Gly—Gly—NHCH$_2$CH$_2$—CH$_2$CH$_2$CH$_2$O— (SEQ ID NO:1) |
| 134 | 101 | 10-CM.Pullulan.Na—Gly—Gly—Gly—Gly—NHCH$_2$CH$_2$—CH$_2$CH$_2$CH$_2$O— (SEQ ID NO:1) |
| 135 | 102 | 9-CM.Dextran.Na—Gly—Gly—NHCH$_2$CH$_2$CH$_2$O— |
| 136 | 102 | 9-CM.Pullulan.Na—Gly—Gly—NHCH$_2$CH$_2$CH$_2$O— |
| 137 | 103 | 9-CM.Dextran.Na—Gly—Gly—Gly—NHCH$_2$CH$_2$CH$_2$O— |
| 138 | 103 | 9-CM.Pullulan.Na—Gly—Gly—Gly—NHCH$_2$CH$_2$CH$_2$O— |
| 139 | 104 | 9-CM.Dextran.Na—Gly—Gly—Gly—Gly—NHCH$_2$CH$_2$CH$_2$O— (SEQ ID NO:1) |
| 140 | 104 | 9-CM.Pullulan.Na—Gly—Gly—Gly—Gly—NHCH$_2$CH$_2$CH$_2$O— (SEQ ID NO:1) |
| 141 | 105 | 11-CM.Dextran.Na—Gly—Gly—NHCH$_2$CH$_2$CH$_2$O— |
| 142 | 105 | 11-CM.Pullulan.Na—Gly—Gly—NHCH$_2$CH$_2$CH$_2$O— |
| 143 | 106 | 11-CM.Dextran.Na—Gly—Gly—Gly—NHCH$_2$CH$_2$CH$_2$O— |
| 144 | 106 | 11-CM.Pullulan.Na—Gly—Gly—Gly—NHCH$_2$CH$_2$CH$_2$O— |

TABLE 8

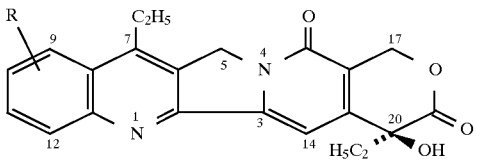

| Ex. No. | Ex. No. of starting compounds | R |
|---|---|---|
| 145 | 107 | 11-CM.Dextran.Na—Gly—Gly—Gly—Gly—NHCH$_2$CH$_2$—CH$_2$O— (SEQ ID NO:1) |
| 146 | 107 | 11-CM.Pullulan.Na—Gly—Gly—Gly—Gly—NHCH$_2$CH$_2$—CH$_2$O— (SEQ ID NO:1) |
| 147 | 108 | 10-CM.Dextran.Na—Gly—Gly—NHCH$_2$CH$_2$O—CH$_2$CH$_2$O— |
| 148 | 108 | 10-CM.Pullulan.Na—Gly—Gly—NHCH$_2$CH$_2$O—CH$_2$CH$_2$O— |
| 149 | 109 | 10-CM.Dextran.Na—Gly—Gly—Gly—NHCH$_2$CH$_2$O—CH$_2$CH$_2$O— |
| 150 | 109 | 10-CM.Pullulan.Na—Gly—Gly—Gly—NHCH$_2$CH$_2$O—CH$_2$CH$_2$O— |
| 151 | 110 | 10-CM.Dextran.Na—Gly—Gly—Gly—Gly—NHCH$_2$CH$_2$O—CH$_2$CH$_2$O— (SEQ ID NO:1) |
| 152 | 110 | 10-CM.Pullulan.Na—Gly—Gly—Gly—Gly—NHCH$_2$CH$_2$O—CH$_2$CH$_2$O— (SEQ ID NO:1) |
| 153 | 111 | 10-CM.Dextran.Na—Gly—Gly—NHCH$_2$CH$_2$—CH$_2$CH$_2$O— |
| 154 | 111 | 10-CM.Pullulan.Na—Gly—Gly—NHCH$_2$CH$_2$—CH$_2$CH$_2$O— |
| 155 | 112 | 10-CM.Dextran.Na—Gly—Gly—Gly—NHCH$_2$CH$_2$—CH$_2$CH$_2$O— |
| 156 | 112 | 10-CM.Pullulan.Na—Gly—Gly—Gly—NHCH$_2$CH$_2$—CH$_2$CH$_2$O— |
| 157 | 113 | 10-CM.Dextran.Na—Gly—Gly—Gly—Gly—NHCH$_2$CH$_2$—CH$_2$CH$_2$O— |
| 158 | 113 | 10-CM.Pullulan.Na—Gly—Gly—Gly—Gly—NHCH$_2$CH$_2$—CH$_2$CH$_2$O— (SEQ ID NO:1) |

Reference Example 1

(1) Dextran (Dextran T-110, average molecular weight; 1000,000 (by the GPC analysis), manufactured by Pharmacia Biotech AB) (29 g) is dissolved in water (290 ml). To the solution is added sodium borohydride (1.45 g) at 0°–5° C., and the mixture is stirred at 5° C. overnight. The pH value of the reaction mixture is adjusted to pH 5 with acetic acid, and the mixture is further stirred at room temperature for 3 hours. The pH value of the mixture is adjusted to pH 7 with 2N sodium hydroxide, and thereto is added ethanol (1.2 L) with vigorously stirring. The mixture is allowed to stand, and the insoluble materials are precipitated. The supernatant of the mixture is removed by decantation, and the residue is centrifuged. The residue is dissolved in water (0.5 L) and the mixture is lyophilized to give a white powder (26.3 g).

(2) The white powder thus obtained (100 g) is dissolved in water (1000 ml), and thereto is added sodium hydroxide (400 g) under ice-cooling. The mixture is stirred for 30 minutes, and warmed to room temperature. To the mixture is added dropwise an aqueous solution (660 ml) of monochloroacetic acid (220 g), and the mixture is stirred at 40° C. for 18 hours. The reaction mixture is cooled to a temperature below 10° C., and the pH value of the mixture is adjusted to pH 8-9 with acetic acid. Methanol (8 L) is added to the reaction mixture with vigorously stirring, and the insoluble materials are precipitated. The insoluble materials are collected by filtration, and dissolved in pure water (5 L). The solution is desalted by ultrafiltration. The residual solution is concentrated under reduced pressure, and filtered. Ethanol is added to the filtrate and precipitated material is collected by filtration, washed with aqueous ethanol and acetone, and dried under reduced pressure at room temperature and dried under reduced pressure at 50° C. to give carboxymethyldextran (CM-dextran) sodium salt (the degree of carboxymethylation by neutralization titration method; 0.45) (101 g).

Reference Examples 2–7

CM-Dextran sodium salts as listed in Table 9 are obtained in the same manner as in Reference Example 1 except for the amount of monochloroacetic acid is changed.

TABLE 9

| Reference Example No. | Degree of carboxymethylation of CM-dextran sodium salt (neutralization titration method) |
| --- | --- |
| 2 | 0.4 |
| 3 | 0.5 |
| 4 | 0.6 |
| 5 | 0.55 |
| 6 | 0.64 |
| 7 | 0.65 |

Reference Example 8

Pullulan (average molecular weight; 150,000 by the GPC analysis, manufactured by Hayashibara Biochemical Laboratories, Inc.) is treated in the same manner as in Reference Example 1 to give carboxymethylpullulan (CM-pullulan) sodium salt (the degree of carboxymethylation by neutralization titration method; 0.5).

What is claimed is:

1. A camptothecin-polysaccharide complex comprising (A) a camptothecin compound of the formula

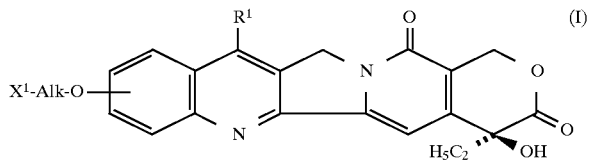

wherein $R^1$ is a lower alkyl group, which may optionally be substituted by groups selected from the group consisting of a protected or unprotected hydroxy, mercapto and amino group, $X^1$ is a group of the formula: —$NHR^2$ ($R^2$ is a hydrogen atom or a lower alkyl group) or a group of the formula: —OH, and Alk is a straight chain or branched chain alkylene group having optionally an oxygen atom in the chain thereof, (B) a polysaccharide having carboxyl groups bonded to (C) an amino acid or a peptide, said amino acid or peptide being bonded to $X^1$ of the camptothecin compound (I), or a pharmaceutically acceptable salt thereof.

2. The complex according to claim 1, wherein a part or all the carboxyl groups of the polysaccharide are bonded to an amino group of the amino acid or the peptide through acid-amide bonds, and a part or all of the carboxyl groups of said amino acid or said peptide are bonded to $X^1$ of the compound [I] through acid-amide or ester bonds, or a pharmaceutically acceptable salt thereof.

3. The complex according to claim 2, wherein a part or all of the carboxyl groups of the polysaccharide are bonded to the N-terminal amino group of the amino acid or the peptide through an acid-amide bond, and the C-terminal carboxyl group of the amino acid or the peptide is bonded to $X^1$ of the compound [I] through an acid-amide or ester bond, or a pharmaceutically acceptable salt thereof.

4. The complex according to claim 3, wherein $X^1$ of the compound [I] is a group of the formula: —$NHR^2$ ($R^2$ is the same as defined in claim 1), and the polysaccharide having carboxyl groups is a carboxymethylated dextran or pullulan, and the compound [I] and the polysaccharide are combined via a peptide, or a pharmaceutically acceptable salt thereof.

5. The complex according to claim 4, wherein $R^1$ of the compound [I] is an unsubstituted lower alkyl group, $X^1$ is an amino group, Alk is a straight chain alkylene group having no oxygen atom in the chain thereof, and the polysaccharide is a carboxymethylated dextran, or a pharmaceutically acceptable salt thereof.

6. The complex according to claim 5, wherein the peptide is a member selected from the group consisting of glycyl-glycyl-L or D-phenylalanyl-glycine, glycyl-glycine, glycyl-glycyl-glycine, glycyl-glycyl-glycyl-glycine, glycyl-glycyl-glycyl-glycyl-glycine, L or D-phenylalanyl-glycine and L or D-leucyl-glycine, or a pharmaceutically acceptable salt thereof.

7. The complex according to claim 6, wherein the peptide is glycyl-glycyl-L-phenylalanyl-glycine, $R^1$ of the compound [I] is ethyl group, and $X^1$—Alk—O— of the compound [I] is 3-aminopropyloxy group which is bonded to the 10-position of the camptothecin nucleus, or a pharmaceutically acceptable salt thereof.

8. The complex according to claim 6, wherein the peptide is glycyl-glycine, $R^1$ of the compound [I] is ethyl group, and $X^1$—Alk—O— of the compound [I] is 3-aminopropyloxy group which is bonded to the 10-position of the camptothecin nucleus, or a pharmaceutically acceptable salt thereof.

9. The complex according to claim 6, wherein the peptide is glycyl-glycyl-glycine, $R^1$ of the compound [I] is ethyl group, and $X^1$—Alk—O— of the compound [I] is 3-aminopropyloxy group which is bonded to the 10-position of the camptothecin nucleus, or a pharmaceutically acceptable salt thereof.

10. The complex according to claim 6, wherein the peptide is glycyl-glycyl-glycyl-glycine, $R^1$ of the compound [I] is ethyl group, and $X^1$—Alk—O— of the compound [I] is 3-aminopropyloxy group which is bonded to the 10-position of the camptothecin nucleus, or a pharmaceutically acceptable salt thereof.

11. The complex according to claim 6, wherein the peptide is L- or D-phenylalanyl-glycine, $R^1$ of the compound [I] is ethyl group, and $X^1$—Alk—O— of the compound [I] is 3-aminopropyloxy group which is bonded to the 10-position of the camptothecin nucleus, or a pharmaceutically acceptable salt thereof.

12. The complex according to any one of claims 7, 8, 9, 10 and 11, wherein the degree of carboxymethylation of the polysaccharide is in the range of 0.3 to 0.8, or a pharmaceutically acceptable salt thereof.

13. A camptothecin compound of the formula (I):

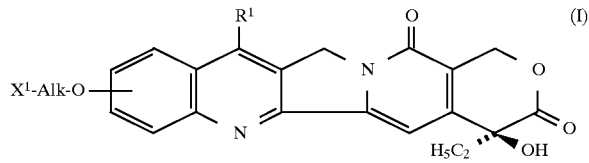

wherein $R^1$ is a lower alkyl group, which may optionally be substituted by groups selected from the group consisting of a protected or unprotected hydroxy, mercapto and amino group, $X^1$ is a group of the formula: —$NHR^2$ ($R^2$ is a hydrogen atom or a lower alkyl group) or a group of the formula: —OH, Alk is a straight chain or branched chain alkylene group having optionally an oxygen atom in the chain thereof, or a salt thereof.

14. The compound according to claim 13, wherein $R^1$ is an unsubstituted lower alkyl group, $X^1$ is an amino group, and Alk is a straight chain alkylene group having no oxygen atom in the chain thereof, or a salt thereof.

15. The compound according to claim 14, wherein $R^1$ is ethyl group, and $X^1$—Alk—O— is 3-aminopropyloxy group which is bonded to the 10-position of the camptothecin nucleus, or a salt thereof.

16. A camptothecin derivative comprising (A) a camptothecin compound of the formula (I):

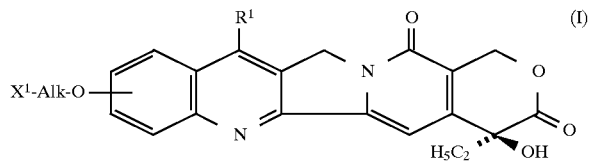

wherein $R^1$ is a lower alkyl group, which may optionally be substituted by groups selected from the group consisting of a protected or unprotected hydroxy, mercapto and amino group, $X^1$ is a group of the formula: —NHR$^2$ (R$^2$ is a hydrogen atom or a lower alkyl group) or a group of the formula: —OH, and Alk is a straight chain or branched chain alkylene group having optionally an oxygen atom in the chain thereof, bonded to (C) an amino acid or a peptide at $X^1$ of the camptothecin compound (I), or a salt thereof.

17. The derivative according to claim 16, wherein a part or all of the carboxyl groups of the amino acid or the peptide are bonded to $X^1$ of the compound [I] through acid-amide or ester bonds, or a salt thereof.

18. The derivative according to claim 17, wherein the C-terminal carboxyl group of the amino acid or the peptide is bonded to $X^1$ of the compound [I] through acid-amide or ester bonds, or a salt thereof.

19. The derivative according to claim 18, wherein $X^1$ of the compound [I] is a group of the formula: —NHR$^2$ (R$^2$ is a hydrogen atom or a lower alkyl group), or a salt thereof.

20. The derivative according to claim 19, wherein the peptide is a member selected from the group consisting of glycyl-glycyl-L or D-phenylalanyl-glycine, glycyl-glycine, glycyl-glycyl-glycine, glycyl-glycyl-glycyl-glycine, glycyl-glycyl-glycyl-glycyl-glycine, L or D-phenylalanyl-glycine and L or D-leucyl-glycine, or a salt thereof.

21. The derivative according to claim 20, wherein R$^1$ is an unsubstituted lower alkyl group, $X^1$ is an amino group, and Alk is a straight chain alkylene group having no oxygen atom in the chain thereof, or a salt thereof.

22. The derivative according to claim 21, wherein the peptide is glycyl-glycyl-L-phenylalanyl-glycine, R$^1$ of the compound [I] is ethyl group, and $X^1$—Alk—O— of the compound [I] is 3-aminopropyloxyl group which is bonded to the 10-position of the camptothecin nucleus, or a salt thereof.

23. The derivative according to claim 21, wherein the peptide is glycyl-glycine, R$^1$ of the compound [I] is ethyl group, and $X^1$—Alk—O— of the compound [I] is 3-aminopropyloxyl group which is bonded to the 10-position of the camptothecin nucleus, or a salt thereof.

24. The derivative according to claim 21, wherein the peptide is glycyl-glycyl-glycine, R$^1$ of the compound [I] is ethyl group, and $X^1$—Alk—O— of the compound [I] is 3-aminopropyloxyl group which is bonded to the 10-position of the camptothecin nucleus, or a salt thereof.

25. The derivative according to claim 21, wherein the peptide is glycyl-glycyl-glycyl-glycine, R$^1$ of the compound [I] is ethyl group, and $X^1$—Alk—O— of the compound [I] is 3-aminopropyloxyl group which is bonded to the 10-position of the camptothecin nucleus, or a salt thereof.

26. The derivative according to claim 21, wherein the peptide is L- or D-phenylalanyl-glycine, R$^1$ of the compound [I] is ethyl group, and $X^1$-Alk- O— of the compound [I] is 3-aminopropyloxyl group which is bonded to the 10-position of the camptothecin nucleus, or a salt thereof.

27. The complex according to claim 4, wherein
R$^1$ of the compound (I) is an unsubstituted lower alkyl group,
$X^1$ is an amino group,
Alk is a straight chain or branched chain lower alkylene group having no oxygen atom in the chain thereof,
and the polysaccharide is a carboxymethylated dextran, or a pharmaceutically acceptable salt thereof.

28. The compound according to claim 13, wherein
R$^1$ is an unsubstituted lower alkyl group,
$X^1$ is an amino group,
and Alk is a straight chain or branched chain lower alkylene group having no oxygen atom in the chain thereof,
or a salt thereof.

29. The derivative according to claim 20, wherein
R$^1$ is an unsubstituted lower alkyl group,
$X^1$ is an amino group,
and Alk is a straight chain or branched chain lower alkylene group having no oxygen atom in the chain thereof,
or a salt thereof.

30. A process for preparing a camptothecin-polysaccharide complex comprising (A) a camptothecin compound represented by the formula (I):

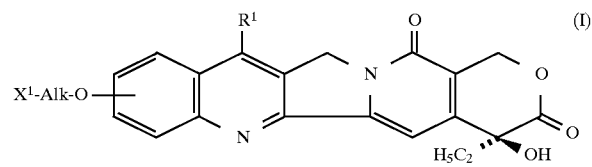

wherein R' is a lower alkyl group, which may optionally be substituted by groups selected from the group consisting of a protected or unprotected hydroxy, mercapto and amino group, $X^1$ is a group of the formula: —NHR$^2$ (R$^2$ is a hydrogen atom or a lower alkyl group) or a group of the formula: —OH, and Alk is a straight chain or branched chain alkylene group having optionally an oxygen atom in the chain thereof, (B) a polysaccharide having carboxyl groups bonded to (C) an amino acid or a peptide said amino acid or peptide being bonded to $X^1$ of the compound (I), or a pharmaceutically acceptable salt thereof, which process comprises reacting the camptothecin derivative prepared by combining the compound with an amino acid or a peptide, after removing the protecting group of an amino group therefrom when an amino group thereof is protected, with a polysaccharide having carboxyl groups, and then, if required, converting the resulting compound into a pharmaceutically acceptable salt thereof.

31. A process for preparing a camptothecin derivative comprising (A) a camptothecin compound represented by the formula (I):

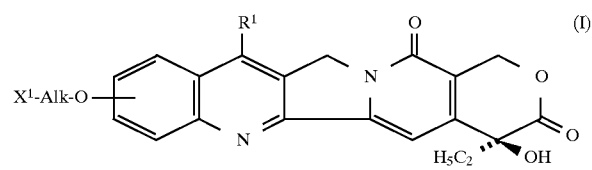

wherein R$^1$ is a lower alkyl group, which may optionally be substituted by groups selected from the group consisting of a protected or unprotected hydroxy, mercapto and amino group, $X^1$ is a group of the formula: —NHR$^2$ (R$^2$ is a hydrogen atom or a lower alkyl group) or a group of the formula: —OH, and Alk is a straight chain or branched chain alkylene group having optionally an oxygen atom in the chain thereof, and (C) an amino acid or a peptide bonded to $X^1$ of the compound (I), or a salt thereof, which comprises reacting the compound (I) with an amino acid or a peptide, removing the protecting group of an amino group or a carboxyl group therefrom when an amino group or a carboxyl group thereof is protected, and then, if required, converting the resulting compound into a salt thereof.

32. A process for preparing a camptothecin compound derivative comprising (A) a camptothecin represented by the formula (I):

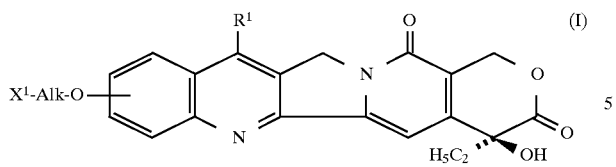

wherein $R^1$ is a lower alkyl group, which may optionally be substituted by groups selected from the group consisting of a protected or unprotected hydroxy, mercapto and amino group, $X^1$ is a group of the formula: —$NHR^2$ ($R^2$ is a hydrogen atom or a lower alkyl group) or a group of the formula: —OH, and Alk is a straight chain or branched chain alkylene group having optionally an oxygen atom in the chain thereof, bonded to (C) an amino acid or a peptide at $X^1$ of the compound (I), or a salt thereof, which process comprises reacting an aminocarbonyl compound represented by the formula (II):

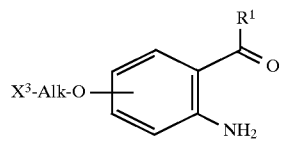

wherein $X^3$ is $R^3$—$N(R^2)$— or $R^3$—O—, $R^3$ is a group which is prepared by removing a hydroxy group from the carboxyl group of an amino acid or peptide having a protected amino group, and $R^1$, $R^2$ and Alk are the same as defined above, with a pyranoindolidine represented by the formula (2):

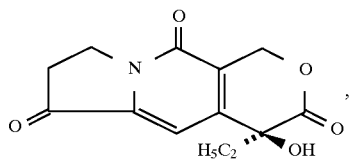

removing the protecting group of an amino group from the resulting compound, and then, if required, converting the resulting compound into a salt thereof.

33. A process for preparing a camptothecin compound represented by the formula (I):

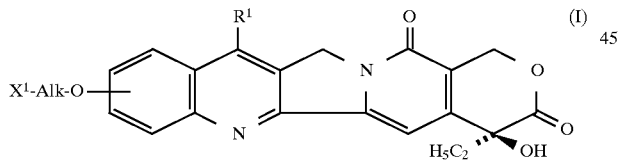

wherein $R^1$ is a lower alkyl group, which may optionally be substituted by groups selected from the group consisting of a protected or unprotected hydroxy, mercapto and amino group, $X^1$ is a group of the formula: —$NHR^2$ ($R^2$ is a hydrogen atom or a lower alkyl group) or a group of the formula: —OH, and Alk is a straight chain or branched chain alkylene group having optionally an oxygen atom in the chain thereof, or a salt thereof, which comprises reacting an aminocarbonyl compound represented by the formula (1):

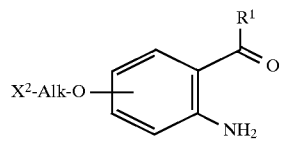

wherein $X^2$ is a protecting group —$N(R^2)$— or a protecting group —O—, and $R^1$, $R^2$ and Alk are the same as defined above, with a pyranoindolidine represented by the formula (2):

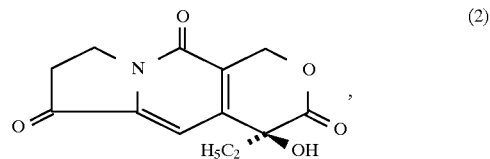

removing the protecting group from the resulting compound, and then, if required, converting the resulting compound into a salt thereof.

34. A process for preparing a camptothecin-polysaccharide complex comprising (A) a camptothecin compound represented by the formula (I):

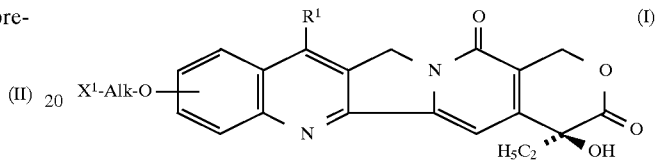

wherein $R^1$ is a lower alkyl group, which may optionally be substituted by groups selected from the group consisting of a protected or unprotected hydroxy, mercapto and amino group, $X^1$ is a group of the formula: —$NHR^2$ ($R^2$ is a hydrogen atom or a lower alkyl group) or a group of the formula: —OH, and Alk is a straight chain or branched chain alkylene group having optionally an oxygen atom in the chain thereof, (B) a polysaccharide having carboxyl groups bonded to (C) an amino acid or a peptide, said amino acid or peptide being bonded to $X^1$ of the compound (I), or a pharmaceutically acceptable salt thereof, which process comprises:

(1) reacting an aminocarbonyl compound represented by the formula (1):

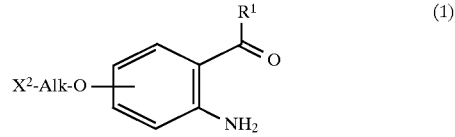

wherein $x^2$ is a protecting group —$N(R^2)$— or a protecting group —O—, and $R^1$, $R^2$ and Alk are the same as defined above, with a pyranoindolidine represented by the formula (2):

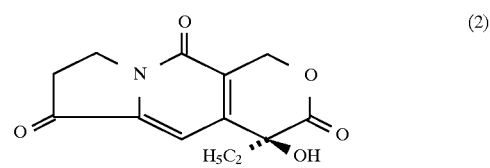

removing the protecting group therefrom:

(2) reacting the resulting compound (I) with an amino acid or a peptide, removing the protecting group of an amino group or a carboxyl group from the resulting compound when an amino group or a carboxyl group thereof is protected; and (3) reacting the resulting compound having an amino acid or a peptide with a polysaccharide having carboxyl groups, and then, if required, converting the resulting compound into a pharmaceutically acceptable salt thereof.

35. A process for preparing a camptothecin: polysaccharide complex comprising (A) a camptothecin compound represented by the formula (I):

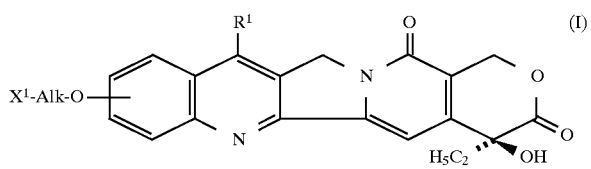

wherein $R^1$ is a lower alkyl group, which may optionally be substituted by groups selected from the group consisting of a protected or unprotected hydroxy, mercapto and amino group, $X^1$ is a group of the formula: —$NHR^2$ ($R^2$ is a hydrogen atom or a lower alkyl group) or a group of the formula: —OH, and Alk is a straight chain or branched chain alkylene group having optionally an oxygen atom in the chain thereof, (B) a polysaccharide having carboxyl groups bonded to (C) an amino acid or a peptide, said amino acid or peptide being bonded to $X^1$ of the compound (I), or a pharmaceutically acceptable salt thereof, which comprises (1) reacting an aminocarbonyl compound represented by the formula (II)

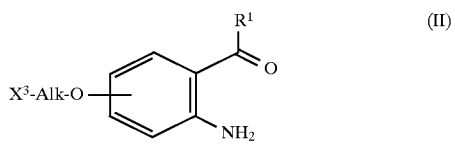

wherein $X^3$ is $R^3$—$N(R^2)$— or $R^3$—O—, $R^3$ is a group which is prepared by removing a hydroxy group from the carboxyl group of an amino acid or peptide having a protected amino group, and $R^1$, $R^2$ and Alk are the same as defined above, with a pyranoindolidine represented by the formula (2):

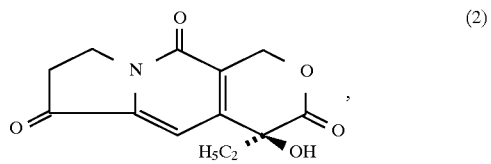

removing the protecting group of an amino group from the resulting compound;

(2) reacting the resulting compound having an amino acid or a peptide with a polysaccharide having carboxyl groups, and then, if required, converting the resulting compound into a pharmaceutically acceptable salt thereof.

36. A pharmaceutical composition which comprises a therapeutically effective amount of a camptothecin-polysacchride complex as set forth in either one of claims 1–6 and 17 in an admixture of a conventional pharmaceutically acceptable carrier or diluent.

37. A pharmaceutical composition which comprises a therapeutically effective amount of a camptothecin-polysaccharide complex as set forth in claim 7 in an admixture of a conventional pharmaceutically acceptable carrier or diluent.

38. A pharmaceutical composition which comprises a therapeutically effective amount of a camptothecin-polysacchride complex as set forth in claim 8 in an admixture of a conventional pharmaceutically acceptable carrier or diluent.

39. A pharmaceutical composition which comprises a therapeutically effective amount of a camptothecin-polysaccharide complex as set forth in claim 9 in an admixture of a conventional pharmaceutically acceptable carrier or diluent.

40. A pharmaceutical composition which comprises a therapeutically effective amount of a camptothecin-polysacchride complex as set forth in claim 10 in an admixture of a conventional pharmaceutically acceptable carrier or diluent.

41. A pharmaceutical composition which comprises a therapeutically effective amount of a camptothecin-polysacchride complex as set forth in claim 11 in an admixture of a conventional pharmaceutically acceptable carrier or diluent.

42. A method for the treatment of a tumor in a patient, which comprises administering to said patient a therapeutically effective amount of a camptothecin-polysaccharide complex as set forth in either one of claims 1–6 and 27.

43. A method for the treatment of a tumor in a patient, which comprises administering to said patient a therapeutically effective amount of a camptothecin-polysaccharide complex as set forth in claim 7.

44. A method for the treatment of a tumor in a patient, which comprises administering to said patient a therapeutically effective amount of a camptothecin-polysaccharide complex as set forth in claim 8.

45. A method for the treatment of a tumor in a patient, which comprises administering to said patient a therapeutically effective amount of a camptothecin-polysaccharide complex as set forth in claim 9.

46. A method for the treatment of a tumor in a patient, which comprises administering to said patient a therapeutically effective amount of a camptothecin-polysaccharide complex as set forth in claim 10.

47. A method for the treatment of a tumor in a patient, which comprises administering to said patient a therapeutically effective amount of a camptothecin-polysaccharide complex as set forth in claim 11.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Gly  Gly  Gly  Gly
    1

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:2:

Gly  Gly  Gly  Gly  Gly
    1                        5

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:3:

-continued

Gly Gly Phe Gly
1